(12) United States Patent
Zhang et al.

(10) Patent No.: US 8,088,811 B2
(45) Date of Patent: Jan. 3, 2012

(54) HETEROCYCLE DERIVATIVES USEFUL AS SELECTIVE ANDROGEN RECEPTOR MODULATORS (SARMS)

(75) Inventors: Xuqing Zhang, Raritan, NJ (US); Xiaojie Li, Raritan, NJ (US); Zhihua Sui, Raritan, NJ (US)

(73) Assignee: Janssen Pharmaceutica N.V., Beerse (BE)

( * ) Notice: Subject to any disclaimer, the term of this patent is extended or adjusted under 35 U.S.C. 154(b) by 50 days.

(21) Appl. No.: 12/830,733

(22) Filed: Jul. 6, 2010

(65) Prior Publication Data

US 2010/0267670 A1 Oct. 21, 2010

Related U.S. Application Data

(62) Division of application No. 12/127,388, filed on May 27, 2008, now Pat. No. 7,781,473, which is a division of application No. 11/258,448, filed on Oct. 25, 2005, now Pat. No. 7,465,809.

(60) Provisional application No. 60/628,337, filed on Nov. 16, 2004.

(51) Int. Cl.
*A61K 31/4155* (2006.01)
*A61K 31/4166* (2006.01)
*A61K 31/4178* (2006.01)
*A61K 31/42* (2006.01)
*A61K 31/422* (2006.01)

(52) U.S. Cl. ....................................... 514/403
(58) Field of Classification Search ........... 514/403
See application file for complete search history.

(56) References Cited

U.S. PATENT DOCUMENTS 6,906,070 B2 6/2005 Lam et al.
2003/0162787 A1* 8/2003 Bigge et al. ............ 514/252.03
2004/0019059 A1 1/2004 Freyne et al.
2006/0063819 A1 3/2006 Lanter et al.

FOREIGN PATENT DOCUMENTS

| WO | WO 98/22432 A1 | 5/1998 |
|---|---|---|
| WO | WO 02/00651 A2 | 1/2002 |
| WO | WO 2004/113309 A1 | 12/2004 |
| WO | WO 2006/031715 A2 | 3/2006 |

OTHER PUBLICATIONS

Prostate cancer [online], retrieved on Jun. 6, 2009 from the internet {URL: http://www.healthline.com/adamcontent/prostate-cancer.*
Basaria, S. et al.: "Anabolic-Androgenic Steroid Therapy in the Treatment of Chronic Diseases"; The J. of Clin. Endocrinology & Metabolism (2001) 86(11): 5108-5117.
Bianchi, G. et al.: "Ricerche sulle 2-isossazoline.—Nota II. Su alcune reazioni delle 5-acil-2-isos-sazoline. (*) (**)"; Gazzetta Chimica Italiana (1968) 98(3): 331-343. (English language abstract).
De Nardo, M.: "Nota XIV(*)—Analoghi dell'aspartame(**).";
Farmaco, Edizione Scientifica (1977) 32(7): 522-530. (English language abstract).
Newling, D.W.W.: "Anti-androgens in the treatment of prostate cancer"; British J. of Urology (1996) 77: 776-784.
Sayed, G.H. et al.: "Some Reactions of 3,4-Dichloro-β-Benzoyl-N-Tolylacrylamide"; Revie roumaine de Chimie (1983) 28(5): 493-498.
Shahidi, N.T.: "A Review of the Chemistry, Biological Action, and Clinical Applications of Anabolic-Androgenic Steroids"; Clin Therapeutics (2001) 23(9): 1355-1390.
PCT International Search Report for International Appln. No. PCT/US2005/038292 dated Dec. 8, 2006.
PCT Search Report, PCT/US2005/038292, Dec. 8, 2006.

* cited by examiner

*Primary Examiner* — Shawquia Young

(57) ABSTRACT

The present invention is directed to novel heterocycle derivatives, pharmaceutical compositions containing them and their use in the treatment of disorders and conditions modulated by the androgen receptor.

10 Claims, No Drawings

HETEROCYCLE DERIVATIVES USEFUL AS SELECTIVE ANDROGEN RECEPTOR MODULATORS (SARMS)

CROSS REFERENCE TO RELATED APPLICATIONS

This application is a divisional application of U.S. application Ser. No. 12/127,388, filed on May 27, 2008, issued as U.S. Pat. No. 7,781,473, which is a divisional of U.S. application Ser. No. 11/258,448, filed on Oct. 25, 2005, issued as U.S. Pat. No. 7,465,809 and claims the benefit of U.S. Provisional Application 60/628,337, filed on Nov. 16, 2004, abandoned.

FIELD OF THE INVENTION

The present invention is directed to novel heterocycle derivatives, pharmaceutical compositions containing them and their use in the treatment of disorders mediated by one or more androgen receptors and processes for their preparation. The compounds of the present invention are selective androgen receptor modulators (SARMs).

BACKGROUND OF THE INVENTION

Androgens are the anabolic steroid hormones of animals, controlling muscle and skeletal mass, the maturation of the reproductive system, the development of secondary sexual characteristics and the maintenance of fertility in the male. In women, testosterone is converted to estrogen in most target tissues, but androgens themselves may play a role in normal female physiology, for example, in the brain. The chief androgen found in serum is testosterone, and this is the effective compound in tissues such as the testes and pituitary. In prostate and skin, testosterone is converted to dihydrotestosterone (DHT) by the action of 5α-reductase. DHT is a more potent androgen than testosterone because it binds more strongly to the androgen receptor.

Like all steroid hormones, androgens bind to a specific receptor inside the cells of target tissues, in this case the androgen receptor. This is a member of the nuclear receptor transcription factor family. Binding of androgen to the receptor activates it and causes it to bind to DNA binding sites adjacent to target genes. From there it interacts with co-activator proteins and basic transcription factors to regulate the expression of the gene. Thus, via its receptor, androgens cause changes in gene expression in cells. These changes ultimately have consequences on the metabolic output, differentiation or proliferation of the cell that are visible in the physiology of the target tissue.

Although modulators of androgen receptor function have been employed clinically for some time, both the steroidal (Basaria, S., Wahlstrom, J. T., Dobs, A. S., *J. Clin Endocrinol Metab* (2001), 86, pp 5108-5117; Shahidi, N. T., *Clin Therapeutics*, (2001), 23, pp 1355-1390), and non-steroidal (Newling, D. W., *Br. J. Urol.*, 1996, 77 (6), pp 776-784) compounds have significant liabilities related to their pharmacological parameters, including gynecomastia, breast tenderness and hepatoxicity. In addition, drug-drug interactions have been observed in patients receiving anticoagulation therapy using coumarins. Finally, patients with aniline sensitivities could be compromised by the metabolites of non-steroidal antiandrogens.

Non-steroidal agonists and antagonists of the androgen receptor are useful in the treatment of a variety of disorders and diseases. More particularly, agonists of the androgen receptor could be employed in the treatment of prostate cancer, benign prostatic hyperplasia, hirsutism in women, alopecia, anorexia nervosa, breast cancer and acne. Antagonists of the androgen receptor could be employed in male contraception, male performance enhancement, as well as in the treatment of cancer, AIDS, cachexia, and other disorders.

Nonetheless, there exists a need for small molecule, non-steroidal antagonists of the androgen receptor. We now describe a novel series of tri-substituted pyrazole derivatives as androgen receptor modulators.

SUMMARY OF THE INVENTION

The present invention is directed to compounds of formula (I)

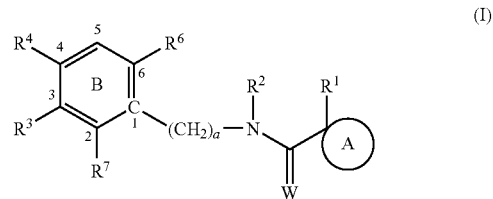

wherein

W is selected from the group consisting of O, S and $NR^F$;

$R^F$ is selected from the group consisting of hydrogen, hydroxy, cyano, $C_{1-4}$alkyl, $C_{1-4}$alkoxy and —$SO_2$—$C_{1-4}$alkyl;

$R^1$ is selected from the group consisting of $C_{1-4}$alkyl and halogenated $C_{1-4}$alkyl;

$R^2$ is selected from the group consisting of hydrogen, $C_{1-4}$alkyl, halogenated $C_{1-4}$alkyl, —C(O)O—$C_{1-4}$alkyl, —C(O)—$C_{1-4}$alkyl and —C(O)-(halogenated $C_{1-4}$alkyl);

a is an integer from 0 to 1;

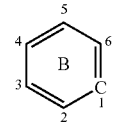

is selected from the group consisting of phenyl, pyridyl, pyrazinyl, pyrimidinyl and pyridazinyl;

$R^3$ is absent or selected from the group consisting of hydrogen, halogen, $C_{1-4}$alkyl, halogenated $C_{1-4}$alkyl, cyano, nitro, amino, $C_{1-4}$alkylamino, di($C_{1-4}$alkyl)amino, —O—$C_{1-4}$alkyl, —S(O)$_{0-2}$—$C_{1-4}$alkyl, —$NR^A$—C(O)—$C_{1-4}$alkyl, benzyl, —O-phenyl, —C(O)-phenyl and —S(O)$_{0-2}$-phenyl; wherein $R^A$ is selected from hydrogen or $C_{1-4}$alkyl;

$R^4$ absent or is selected from the group consisting of hydrogen, halogen, $C_{1-4}$alkyl, halogenated $C_{1-4}$alkyl, cyano, nitro, amino, $C_{1-4}$alkylamino, di($C_{1-4}$alkyl)amino, —O—$C_{1-4}$alkyl, —S(O)$_{0-2}$—$C_{1-4}$alkyl, —$NR^B$—C(O)—$C_{1-4}$alkyl, benzyl, —O-phenyl, —C(O)-phenyl and —S(O)$_{0-2}$-phenyl; wherein $R^B$ is selected from hydrogen or $C_{1-4}$alkyl;

provided that when

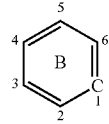

is phenyl then at least one of $R^3$ or $R^4$ is other than hydrogen;

$R^6$ and $R^7$ are each independently absent or selected from the group consisting of hydrogen halogen, $C_{1-4}$alkyl, $C_{2-4}$alkenyl, $C_{1-4}$alkoxy, cyano, —C(O)O—$C_{1-4}$alkyl and —S(O)$_{0-2}$—$C_{1-4}$alkyl;

provided further that $R^3$ is absent when a nitrogen atom is present at the 3-position of

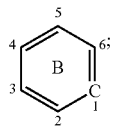

provided further that $R^4$ is absent when a nitrogen atom is present at the 4-position of

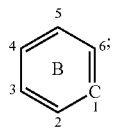

provided further that $R^6$ is absent when a nitrogen atom is present at the 6-position of

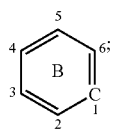

provided further that $R^7$ is absent when a nitrogen atom is present at the 2-position of

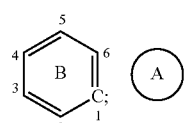

is selected from the group consisting of

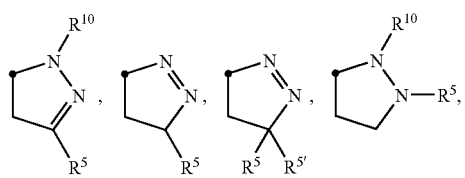

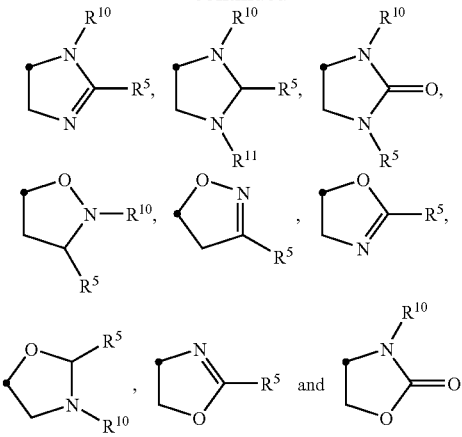

wherein $R^{5'}$ is selected from the group consisting of halogen and $C_{1-4}$alkyl; and wherein $R^{10}$ and $R^{11}$ are each independently selected from hydrogen, $C_{1-4}$alkyl, benzyl or —C(O)—CF$_3$;

$R^5$ is selected from the group consisting of hydrogen, carboxy, alkyl, halogenated $C_{1-4}$alkyl, hydroxy substituted $C_{1-4}$alkyl, cycloalkyl, aryl, aralkyl, heteroaryl, heteroarylalkyl-, heterocycloalkyl, heterocycloalkyl-alkyl-, —C(O)-alkyl, —C(O)-(halogenated $C_{1-4}$alkyl), —C(O)O—$C_{1-4}$alkyl, —C(O)O-aryl, —$C_{1-4}$alkyl-S(O)$_{0-2}$—$C_{1-4}$alkyl, t-butyl-dimethyl-silyl and trimethylsilyl;

wherein the aryl, cycloalkyl, heteroaryl or heterocycloalkyl, whether alone or as part of a substituent group is optionally substituted with one or more substituents independently selected from the group consisting of halogen, hydroxy, $C_{1-4}$alkyl, $C_{1-4}$alkoxy, halogenated $C_{1-4}$alkyl, halogenated $C_{1-4}$alkoxy, cyano, nitro, amino, $C_{1-4}$alkylamino, di($C_{1-4}$alkyl)amino, —NR$^C$—C(O)—$C_{1-4}$alkyl, NR$^C$—C(O)-(halogenated $C_{1-4}$alkyl), —C(O)O—$C_{1-4}$alkyl, —S(O)$_{0-2}$—$C_{1-4}$alkyl, —SO$_2$—NR$^C$R$^D$, trimethyl-silyl and t-butyl-dimethyl-silyloxy; wherein each R$^C$ and R$^D$ are each independently selected from hydrogen or $C_{1-4}$alkyl;

and pharmaceutically acceptable salts thereof.

The present invention is further directed to compounds of formula (II)

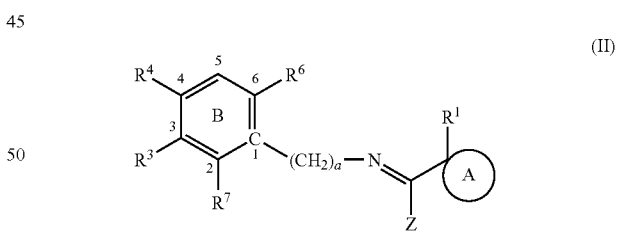

(II)

wherein

Z is selected from the group consisting of OR$^E$, SR$^E$ and N(R$^F$)$_2$;

wherein R$^E$ is selected from the group consisting of hydrogen and $C_{1-4}$alkyl;

wherein each R$^F$ is independently selected from the group consisting of hydrogen, hydroxy, cyano, $C_{1-4}$alkyl, $C_{1-4}$alkoxy and —SO$_2$—$C_{1-4}$alkyl;

provided that when one R$^F$ group is hydroxy or cyano, then the other R$^F$ group is hydrogen;

alternatively, the two R$^F$ groups are taken together with the nitrogen atom to which they are bound to form a 5 to 6 membered, saturated heterocyclic ring structure;

$R^1$ is selected from the group consisting of $C_{1-4}$alkyl and halogenated $C_{1-4}$alkyl;

a is an integer from 0 to 1;

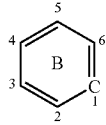

is selected from the group consisting of phenyl, pyridyl, pyrazinyl, pyrimidinyl and pyridazinyl;

$R^3$ is absent or selected from the group consisting of hydrogen, halogen, $C_{1-4}$alkyl, halogenated $C_{1-4}$alkyl, cyano, nitro, amino, $C_{1-4}$alkylamino, di($C_{1-4}$alkyl)amino, —O—$C_{1-4}$alkyl, —S(O)$_{0-2}$—$C_{1-4}$alkyl, —NR$^A$—C(O)—$C_{1-4}$alkyl, benzyl, —O-phenyl, —C(O)-phenyl and —S(O)$_{0-2}$-phenyl; wherein $R^A$ is selected from hydrogen or $C_{1-4}$alkyl;

$R^4$ absent or is selected from the group consisting of hydrogen, halogen, $C_{1-4}$alkyl, halogenated $C_{1-4}$alkyl, cyano, nitro, amino, $C_{1-4}$alkylamino, di($C_{1-4}$alkyl)amino, —O—$C_{1-4}$alkyl, —S(O)$_{0-2}$—$C_{1-4}$alkyl, —NR$^B$—C(O)—$C_{1-4}$alkyl, benzyl, —O-phenyl, —C(O)-phenyl and —S(O)$_{0-2}$-phenyl; wherein $R^B$ is selected from hydrogen or $C_{1-4}$alkyl;

provided that when

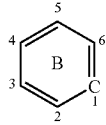

is phenyl then at least one of $R^3$ or $R^4$ is other than hydrogen;

$R^6$ and $R^7$ are each independently absent or selected from the group consisting of hydrogen halogen, $C_{1-4}$alkyl, $C_{2-4}$alkenyl, $C_{1-4}$alkoxy, cyano, —C(O)O—$C_{1-4}$alkyl and —S(O)$_{0-2}$—$C_{1-4}$alkyl;

provided further that $R^3$ is absent when a nitrogen atom is present at the 3-position of

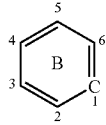

provided further that $R^4$ is absent when a nitrogen atom is present at the 4-position of

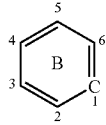

provided further that $R^6$ is absent when a nitrogen atom is present at the 6-position of

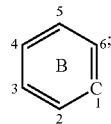

provided further that $R^7$ is absent when a nitrogen atom is present at the 2-position of

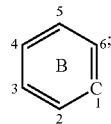

is selected from the group consisting of

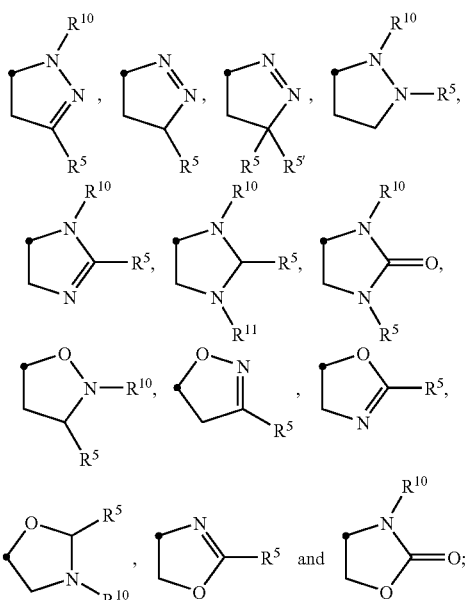

wherein $R^{5'}$ is selected from the group consisting of halogen and $C_{1-4}$alkyl; and wherein $R^{10}$ and $R^{11}$ are each independently selected from hydrogen, $C_{1-4}$alkyl, benzyl or —C(O)—CF$_3$;

$R^5$ is selected from the group consisting of hydrogen, carboxy, alkyl, halogenated $C_{1-4}$alkyl, hydroxy substituted $C_{1-4}$alkyl, cycloalkyl, aryl, aralkyl, heteroaryl, heteroaryl-alkyl-, heterocycloalkyl, heterocycloalkyl-alkyl-, —C(O)-alkyl, —C(O)-(halogenated $C_{1-4}$alkyl), —C(O)O—$C_{1-4}$alkyl, —C(O)O-aryl, —$C_{1-4}$alkyl-S(O)$_{0-2}$—$C_{1-4}$alkyl, t-butyl-dimethyl-silyl and trimethylsilyl;

wherein the aryl, cycloalkyl, heteroaryl or heterocycloalkyl, whether alone or as part of a substituent group is optionally substituted with one or more substituents independently selected from the group consisting of halogen, hydroxy, $C_{1-4}$alkyl, $C_{1-4}$alkoxy, halogenated $C_{1-4}$alkyl, halogenated $C_{1-4}$alkoxy, cyano, nitro, amino, $C_{1-4}$alkylamino, di($C_{1-4}$alkyl)amino, —NR$^C$—C(O)—$C_{1-4}$alkyl, NR$^C$—C(O)-(halogenated $C_{1-4}$alkyl), —C(O)O—$C_{1-4}$alkyl, —S(O)$_{0-2}$—$C_{1-4}$alkyl, —SO$_2$—NR$^C$R$^D$, trimethyl-silyl and t-butyl-dimethyl-silyloxy; wherein each R$^C$ and R$^D$ are each independently selected from hydrogen or $C_{1-4}$alkyl;

and pharmaceutically acceptable salts thereof.

The present invention is further directed to a tautomeric mixture comprising

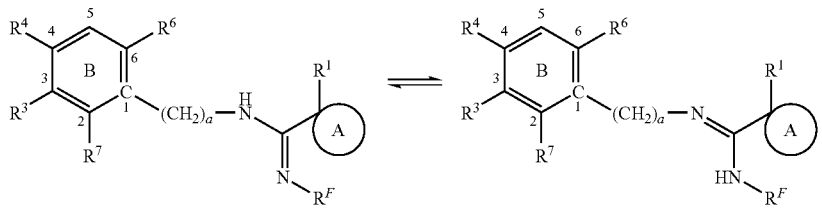

$R^F$ is selected from the group consisting of hydrogen, hydroxy, cyano, $C_{1-4}$alkyl, $C_{1-4}$alkoxy and —$SO_2$—$C_{1-4}$alkyl;
$R^1$ is selected from the group consisting of $C_{1-4}$alkyl and halogenated $C_{1-4}$alkyl;
a is an integer from 0 to 1;

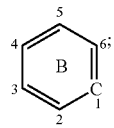

is selected from the group consisting of phenyl, pyridyl, pyrazinyl, pyrimidinyl and pyridazinyl;
$R^3$ is absent or selected from the group consisting of hydrogen, halogen, $C_{1-4}$alkyl, halogenated $C_{1-4}$alkyl, cyano, nitro, amino, $C_{1-4}$alkylamino, di($C_{1-4}$alkyl)amino, —O—$C_{1-4}$alkyl, —$S(O)_{0-2}$—$C_{1-4}$alkyl, —$NR^A$—C(O)—$C_{1-4}$alkyl, benzyl, —O-phenyl, —C(O)-phenyl and —$S(O)_{0-2}$-phenyl; wherein $R^A$ is selected from hydrogen or $C_{1-4}$alkyl;
$R^4$ absent or is selected from the group consisting of hydrogen, halogen, $C_{1-4}$alkyl, halogenated $C_{1-4}$alkyl, cyano, nitro, amino, $C_{1-4}$alkylamino, di($C_{1-4}$alkyl)amino, —O—$C_{1-4}$alkyl, —$S(O)_{0-2}$—$C_{1-4}$alkyl, —$NR^B$—C(O)—$C_{1-4}$alkyl, benzyl, —O-phenyl, —C(O)-phenyl and —$S(O)_{0-2}$-phenyl; wherein $R^B$ is selected from hydrogen or $C_{1-4}$alkyl;
provided that when

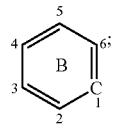

is phenyl then at least one of $R^3$ or $R^4$ is other than hydrogen;
$R^6$ and $R^7$ are each absent or independently selected from the group consisting of hydrogen halogen, $C_{1-4}$alkyl, $C_{2-4}$alkenyl, $C_{1-4}$alkoxy, cyano, —C(O)O—$C_{1-4}$alkyl and —$S(O)_{0-2}$—$C_{1-4}$alkyl;
provided further that $R^3$ is absent when a nitrogen atom is present at the 3-position of

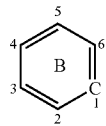

provided further that $R^4$ is absent when a nitrogen atom is present at the 4-position of

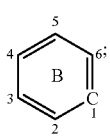

provided further that $R^6$ is absent when a nitrogen atom is present at the 6-position of

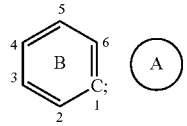

provided further that $R^7$ is absent when a nitrogen atom is present at the 2-position of

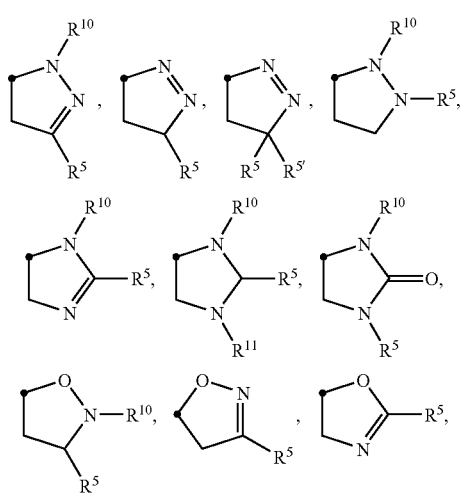

is selected from the group consisting of

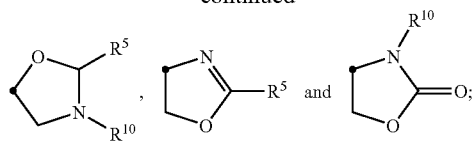

wherein $R^{5'}$ is selected from the group consisting of halogen and $C_{1-4}$alkyl; and wherein $R^{10}$ and $R^{11}$ are each independently selected from hydrogen, $C_{1-4}$alkyl, benzyl or —C(O)—CF$_3$;

$R^5$ is selected from the group consisting of hydrogen, carboxy, alkyl, halogenated $C_{1-4}$alkyl, hydroxy substituted $C_{1-4}$alkyl, cycloalkyl, aryl, aralkyl, heteroaryl, heteroarylalkyl-, heterocycloalkyl, heterocycloalkyl-alkyl-, —C(O)-alkyl, —C(O)-(halogenated $C_{1-4}$alkyl), —C(O)O—$C_{1-4}$ alkyl, —C(O)O-aryl, —$C_{1-4}$alkyl-S(O)$_{0-2}$—$C_{1-4}$alkyl, t-butyl-dimethyl-silyl and trimethylsilyl;

wherein the aryl, cycloalkyl, heteroaryl or heterocycloalkyl, whether alone or as part of a substituent group is optionally substituted with one or more substituents independently selected from the group consisting of halogen, hydroxy, $C_{1-4}$alkyl, $C_{1-4}$alkoxy, halogenated $C_{1-4}$alkyl, halogenated $C_{1-4}$alkoxy, cyano, nitro, amino, $C_{1-4}$alkylamino, di($C_{1-4}$alkyl)amino, —NR$^C$—C(O)—$C_{1-4}$alkyl, NR$^C$—C(O)-(halogenated $C_{1-4}$alkyl), —C(O)O—$C_{1-4}$alkyl, —S(O)$_{0-2}$—$C_{1-4}$alkyl, —SO$_2$—NR$^C$R$^D$, trimethyl-silyl and t-butyl-dimethyl-silyloxy; wherein each R$^C$ and R$^D$ are each independently selected from hydrogen or $C_{1-4}$alkyl;

or a pharmaceutically acceptable salt thereof.

Illustrative of the invention is a pharmaceutical composition comprising a pharmaceutically acceptable carrier and any of the compounds described herein. An illustration of the invention is a pharmaceutical composition made by mixing any of the compounds described herein and a pharmaceutically acceptable carrier. Illustrating the invention is a process for making a pharmaceutical composition comprising mixing any of the compounds described herein and a pharmaceutically acceptable carrier.

Exemplifying the invention are methods of treating disorders and conditions modulated by the androgen receptor comprising administering to a subject in need thereof a therapeutically effective amount of any of the compounds or pharmaceutical compositions described herein.

An example of the invention is a method for treating an androgen receptor modulated disorder selected from the group consisting of prostate carcinoma, benign prostatic hyperplasia, hirsutism, or for male contraception, comprising administering to a subject in need thereof an effective amount of any of the compounds or pharmaceutical compositions described herein.

Another example of the invention is the use of any of the compounds described herein in the preparation of a medicament for treating: (a) prostate carcinoma, (b) benign prostatic hyperplasia, (c) hirsutism, (d) alopecia, (e) anorexia nervosa, (f) breast cancer, (g) acne, (h) AIDS, (i) cachexia, for (j) male contraception, or for (k) male performance enhancement, in a subject in need thereof.

DETAILED DESCRIPTION OF THE INVENTION

The present invention is directed to compounds of formula (I) and compounds of formula (II)

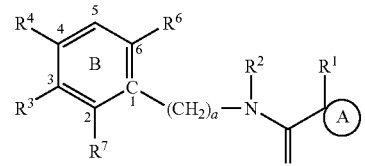

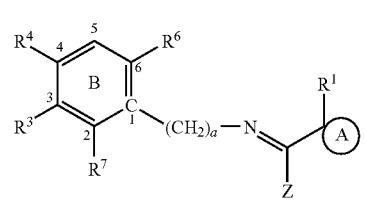

wherein $R^1$, $R^2$, $R^3$, $R^4$, $R^6$, $R^7$, W, Z, a,

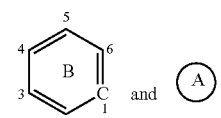

are as herein defined, useful as selective androgen receptor modulators for the treatment of prostate carcinoma, benign prostatic hyperplasia (BPH), hirsutism, alopecia, anorexia nervosa, breast cancer, acne, AIDS, cachexia, as a male contraceptive, and/or as a male performance enhancer.

The present invention is further directed to tautomeric mixtures comprising a compound of formula (It) and a compound of formula (IIt)

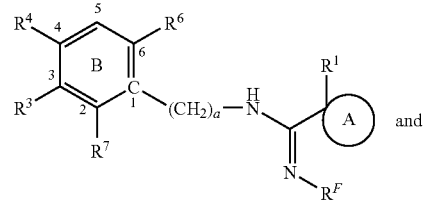

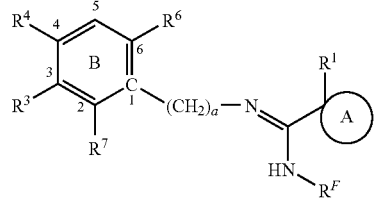

wherein $R^1$, $R^3$, $R^4$, $R^6$, $R^7$, $R^F$, a,

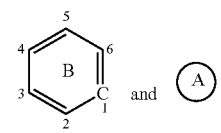

are as herein defined, useful as selective androgen receptor modulators for the treatment of prostate carcinoma, benign prostatic hyperplasia (BPH), hirsutism, alopecia, anorexia nervosa, breast cancer, acne, AIDS, cachexia, as a male contraceptive, and/or as a male performance enhancer.

One skilled in the art will recognize that some of the variables (e.g. $R^1$, $R^2$, $R^3$, a, etc.) appear in compounds of formula (I) and compounds of formula (II). One skilled in the art will further recognize that wherein a particular substituent is selected for a given variable for a compound of formula (I), said selection is not intended to limit the scope of said variable for compounds of formula (II). Similarly, the selection of a particular substituent for a given variable for a compound of formula (II), is not intended to limit the scope of said variable for compounds of formula (I).

One skilled in the art will recognize that when in the compound of formula (I) $R^2$ is hydrogen and W is $NR^F$ and in the compound of formula (II) Z is $NHR^F$, then the corresponding compound of formula (I) and the corresponding compound formula (II) are tautomers. One skilled in the art will further recognize that in solution, the tautomers may exist as a mixture of varying ratios, depending on the nature of the solvent. Upon isolation as a solid, only one of the tautomers is isolated, although which tautomer was isolated was not determined for the compounds of the instant application.

In an embodiment, the present invention is directed to compounds of formula (I)

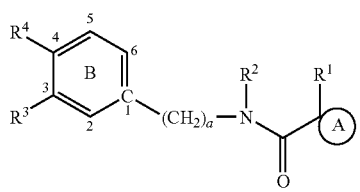

wherein $R^1$ is selected from the group consisting of $C_{1-4}$alkyl and halogenated $C_{1-4}$alkyl;

$R^2$ is selected from the group consisting of hydrogen, $C_{1-4}$alkyl and —C(O)O—$C_{1-4}$alkyl;

a is an integer from 0 to 1;

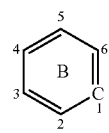

is selected from the group consisting of phenyl, pyridyl, pyrazinyl, pyrimidinyl and pyridazinyl;

$R^3$ is absent or selected from the group consisting of hydrogen, halogen, $C_{1-4}$alkyl, halogenated $C_{1-4}$alkyl, cyano, nitro, amino, $C_{1-4}$alkylamino, di($C_{1-4}$alkyl)amino, —O—$C_{1-4}$alkyl, —S(O)$_{0-2}$—$C_{1-4}$alkyl, —$NR^A$—C(O)—$C_{1-4}$alkyl, benzyl, —O-phenyl, —C(O)-phenyl and —S(O)$_{0-2}$-phenyl; wherein $R^A$ is selected from hydrogen or $C_{1-4}$alkyl;

$R^4$ absent or is selected from the group consisting of hydrogen, halogen, $C_{1-4}$alkyl, halogenated $C_{1-4}$alkyl, cyano, nitro, amino, $C_{1-4}$alkylamino, di($C_{1-4}$alkyl)amino, —O—$C_{1-4}$alkyl, —S(O)$_{0-2}$—$C_{1-4}$alkyl, —$NR^B$—C(O)—$C_{1-4}$alkyl, benzyl, —O-phenyl, —C(O)-phenyl and —S(O)$_{0-2}$-phenyl; wherein $R^B$ is selected from hydrogen or $C_{1-4}$alkyl;

provided that when

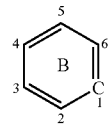

is phenyl then at least one of $R^3$ or $R^4$ is other than hydrogen;

provided further that $R^3$ is absent when a nitrogen atom is present at the 3-position of

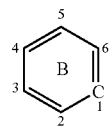

provided further that $R^4$ is absent when a nitrogen atom is present at the 4-position of

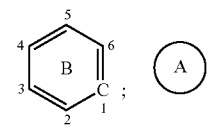

is selected from the group consisting of

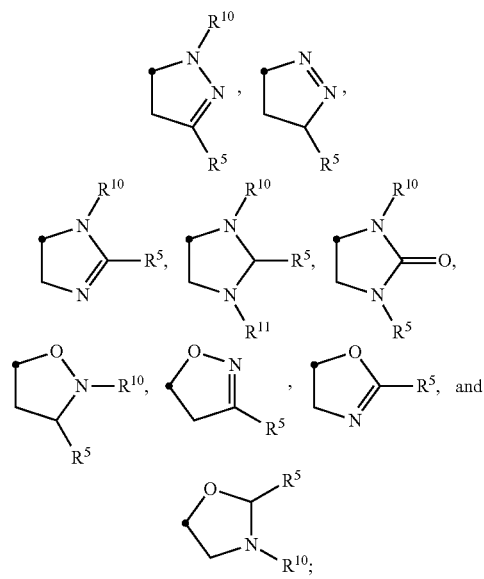

wherein $R^{10}$ and $R^{11}$ are each independently selected from hydrogen, $C_{1-4}$alkyl or benzyl;

$R^5$ is selected from the group consisting of hydrogen, carboxy, alkyl, halogenated $C_{1-4}$alkyl, hydroxy substituted $C_{1-4}$alkyl, cycloalkyl, aryl, aralkyl, heteroaryl, heteroaryl-alkyl-, heterocycloalkyl, heterocycloalkyl-alkyl-, —C(O)-alkyl, —C(O)-(halogenated $C_{1-4}$alkyl), —C(O)O—$C_{1-4}$alkyl, —C(O)O-aryl, —$C_{1-4}$alkyl-S(O)$_{0-2}$—$C_{1-4}$alkyl, t-butyl-dimethyl-silyl and trimethylsilyl;

wherein the aryl, cycloalkyl, heteroaryl or heterocycloalkyl, whether alone or as part of a substituent group is optionally substituted with one or more substituents independently selected from the group consisting of halogen, hydroxy, $C_{1-4}$alkyl, $C_{1-4}$alkoxy, halogenated $C_{1-4}$alkyl, halogenated $C_{1-4}$alkoxy, cyano, nitro, amino, $C_{1-4}$alkylamino, di($C_{1-4}$alkyl)amino, —$NR^C$—C(O)—$C_{1-4}$alkyl, $NR^C$—C(O)-(halogenated $C_{1-4}$alkyl), —C(O)O—$C_{1-4}$alkyl, —S(O)$_{0-2}$—$C_{1-4}$alkyl, —SO$_2$—$NR^C R^D$, trimethyl-silyl and t-butyl-dimethyl-silyloxy; wherein each $R^C$ and $R^D$ are each independently selected from hydrogen or $C_{1-4}$alkyl;

and pharmaceutically acceptable salts thereof.

In an embodiment of the present invention, W is selected from the group consisting of O, S and $NR^F$; wherein $R^F$ is selected from the group consisting of hydrogen, hydroxy, $C_{1-4}$alkyl, $C_{1-4}$alkoxy, cyano and —SO$_2$—$C_{1-4}$alkyl. In another embodiment of the present invention, W is selected from the group consisting of O, S and $NR^F$; wherein $R^F$ is selected from the group consisting of hydrogen, hydroxy, $C_{1-4}$alkyl, $C_{1-2}$alkoxy, cyano and —SO$_2$—$C_{1-2}$alkyl. In another embodiment of the present invention, W is selected from the group consisting of O, S and $NR^F$; wherein $R^F$ is selected from the group consisting of hydrogen, hydroxy, methyl, ethyl, methoxy, cyano and —SO$_2$-methyl. In another embodiment of the present invention, W is selected from the group consisting of O, S and $NR^F$; wherein $R^F$ is selected from the group consisting of hydrogen, methyl, ethyl, methoxy, cyano and —SO$_2$-methyl.

In an embodiment of the present invention, W is selected from the group consisting of O, NH, N(OH), N(ethyl) and N(methoxy). In another embodiment of the present invention, W is selected from the group consisting of O and N(ethyl).

In an embodiment of the present invention W is selected from the group consisting of O and S. Preferably W is O. In another embodiment of the present invention W is selected from the group consisting of O and $NR^F$. In another embodiment of the present invention W is $NR^F$. Preferably, W is $NR^F$ and $R^F$ is selected form the group consisting of hydrogen, hydroxy, cyano, $C_{1-4}$alkyl and —SO$^2$—$C_{1-4}$alkyl. More preferably, W is $NR^F$ and $R^F$ is selected form the group consisting of hydrogen, hydroxy, cyano, methyl, ethyl and —SO$_2$-methyl.

In an embodiment of the present invention, Z is selected from the group consisting of —O-methyl, —O-ethyl, —S-ethyl, —NH$_2$, —NH(OH), —NH-ethyl, —N(ethyl)$_2$ and —NH(OCH$_3$).

In an embodiment of the present invention, $R^E$ is selected from the group consisting of hydrogen and $C_{1-4}$alkyl. In another embodiment of the present invention, $R^E$ is selected from the group consisting of $C_{1-4}$alkyl. In another embodiment of the present invention, $R^E$ is selected from the group consisting of methyl and ethyl.

In an embodiment of the present invention, each $R^F$ is independently selected from the group consisting of hydrogen, hydroxy, cyano, $C_{1-4}$alkyl, $C_{1-4}$alkoxy and —SO$_2$—$C_{1-4}$alkyl. In another embodiment of the present invention, each $R^F$ is independently selected from the group consisting of hydrogen, hydroxy, cyano, $C_{1-4}$alkyl, $C_{1-2}$alkoxy and —SO$_2$—$C_{1-2}$alkyl. In another embodiment of the present invention, $R^F$ is independently selected from the group consisting of hydrogen, hydroxy, cyano, methyl, ethyl, methoxy and —SO$_2$-methyl.

In an embodiment of the present invention, the two $R^F$ groups are taken together with the nitrogen atom to which they are bound to form a 5 to 6 membered, saturated heterocyclic ring structure. In another embodiment of the present invention, the two $R^F$ groups are taken together with the nitrogen, atom to which they are bound to form 1-pyrrolidinyl or 1-piperidinyl. In another embodiment of the present invention, the two $R^F$ groups are taken together with the nitrogen atom to which they are bound to form 1-pyrrolidinyl.

In an embodiment of the present invention, $R^1$ is selected from the group consisting of $C_{1-4}$alkyl and halogenated $C_{1-4}$alkyl. In another embodiment of the present invention, $R^1$ is selected from the group consisting of $C_{1-4}$alkyl and halogenated $C_{1-2}$alkyl. In another embodiment of the present invention, $R^1$ is selected from the group consisting of methyl, (S)-methyl, (R)-methyl, ethyl, n-propyl and trifluoromethyl. In another embodiment of the present invention, $R^1$ is selected from the group consisting of methyl, (R)-methyl, (S)-methyl, ethyl and trifluoromethyl.

In an embodiment of the present invention, $R^1$ is selected from the group consisting of $C_{1-2}$alkyl and halogenated $C_{1-2}$alkyl. In another embodiment of the present invention, $R^1$ is selected from the group consisting of $C_{1-2}$alkyl. In another embodiment of the present invention, $R^1$ is selected from the group consisting of methyl, (R)-methyl and (S)-methyl. In another embodiment of the present invention, $R^1$ is selected from the group consisting of methyl and (S)-methyl.

In an embodiment of the present invention, $R^1$ is selected from the group consisting of $C_{1-2}$alkyl and halogenated $C_{1-2}$alkyl. In another embodiment of the present invention, $R^1$ is selected from the group consisting of $C_{1-4}$alkyl. In another embodiment of the present invention, $R^1$ is selected from the group consisting of methyl, ethyl and n-propyl. Preferably, $R^1$ is selected from the group consisting of methyl, ethyl and n-propyl. More preferably, $R^1$ is selected from the group consisting of methyl, (R)-methyl, (S)-methyl and ethyl. More preferably still, $R^1$ is methyl.

In an embodiment of the present invention, $R^2$ is selected from the group consisting of hydrogen and $C_{1-4}$alkyl. In another embodiment of the present invention, $R^2$ is selected from the group consisting of hydrogen and methyl. Preferably, $R^2$ is hydrogen.

In an embodiment of the present invention, $R^2$ is selected from the group consisting of hydrogen, $C_{1-4}$alkyl, halogenated $C_{1-4}$alkyl and —C(O)-(halogenated $C_{1-4}$alkyl). In another embodiment of the present invention, $R^2$ is selected from the group consisting of hydrogen, $C_{1-4}$alkyl, halogenated $C_{1-2}$alkyl and —C(O)-(halogenated $C_{1-2}$alkyl). In another embodiment of the present invention, $R^2$ is selected from the group consisting of hydrogen, methyl, trifluoroethyl and —C(O)—CF$_3$.

In an embodiment of the present invention, a is 1. In another embodiment of the present invention, a is 0.

In an embodiment of the present invention,

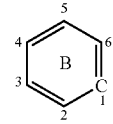

is selected from the group consisting of phenyl and pyridyl. In another embodiment,

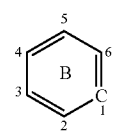

is selected from the group consisting of phenyl, 3-pyridyl and 4-pyridyl. Preferably,

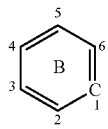

is phenyl. In another embodiment of the present invention,

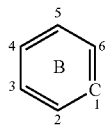

is pyridyl. In yet another embodiment of the present invention,

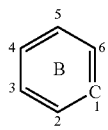

is selected from the group consisting of 3-pyridyl and 4-pyridyl.

In an embodiment of the present invention, $R^3$ is absent or selected from the group consisting of hydrogen, halogen, halogenated $C_{1-4}$alkyl, cyano, nitro, benzyl, —O-phenyl, —C(O)-phenyl, —S(O)$_{0-2}$—$C_{1-4}$alkyl and —S(O)$_{0-2}$-phenyl. In another embodiment of the present invention, $R^3$ is absent or selected from the group consisting of hydrogen, halogen, halogenated $C_{1-4}$alkyl and cyano. Preferably, $R^3$ is absent or selected from the group consisting of hydrogen, chloro, trifluoromethyl and cyano.

In an embodiment of the present invention, $R^3$ is selected from the group consisting of hydrogen, halogen, halogenated $C_{1-4}$alkyl and cyano. In another embodiment of the present invention, $R^3$ is selected from the group consisting of hydrogen, chloro, trifluoromethyl and cyano. Preferably, $R^3$ is selected from the group consisting of hydrogen and trifluoromethyl. More preferably, $R^3$ is trifluoromethyl.

In an embodiment of the present invention, $R^3$ is absent or hydrogen.

In an embodiment of the present invention, $R^3$ is absent or selected from the group consisting of hydrogen, halogen and halogenated $C_{1-2}$alkyl. In another embodiment of the present invention, $R^3$ is halogenated $C_{1-2}$alkyl. In another embodiment of the present invention, $R^3$ is trifluoromethyl.

In an embodiment of the present invention, $R^4$ is selected from the group consisting of hydrogen, halogen, halogenated $C_{1-4}$alkyl, cyano, nitro, benzyl, —O-phenyl, —C(O)-phenyl, —S(O)$_{0-2}$—$C_{1-4}$alkyl and —S(O)$_{0-2}$-phenyl. In another embodiment of the present invention, $R^4$ is absent or selected from the group consisting of halogen, cyano, nitro, benzyl, —O-phenyl, —C(O)-phenyl, —S(O)$_{0-2}$—$C_{1-4}$alkyl and —S(O)$_{0-2}$-phenyl. Preferably, $R^4$ is absent or selected from the group consisting of chloro, bromo, cyano, nitro, benzyl, —O-phenyl, —S-phenyl, —C(O)-phenyl, —SO$_2$-methyl and —SO$_2$-phenyl.

In an embodiment of the present invention, $R^4$ is selected from the group consisting of chloro, bromo, cyano, nitro, benzyl, —O-phenyl, —S-phenyl, —C(O)-phenyl, —SO$_2$-methyl and —SO$_2$-phenyl. In another embodiment of the present invention, $R^4$ is selected from the group consisting of halogen, cyano, nitro, benzyl, —O-phenyl, —C(O)-phenyl, —S(O)$_{0-2}$—$C_{1-4}$alkyl and —S(O)$_{0-2}$-phenyl. Preferably, $R^4$ is selected from the group consisting of bromo, cyano, nitro and —SO$_2$-phenyl. More preferably, $R^4$ is selected from the group consisting of chloro, cyano and nitro.

In an embodiment of the present invention, $R^4$ absent or is selected from the group consisting of cyano and halogen. In another embodiment of the present invention, $R^4$ absent or is selected from the group consisting of cyano and chloro.

In an embodiment of the present invention, $R^4$ is absent or selected from the group consisting of hydrogen, halogen, halogenated $C_{1-2}$alkyl and cyano. In another embodiment of the present invention, $R^4$ is cyano. In an embodiment of the present invention, $R^6$ and $R^7$ are each independently absent or selected from the group consisting of hydrogen, halogen, $C_{1-4}$alkyl, $C_{1-4}$alkoxy, cyano, —C(O)O—$C_{1-4}$alkyl and —S(O)$_{0-2}$—$C_{1-4}$alkyl.

In another embodiment of the present invention, $R^6$ and $R^7$ are each independently absent or selected from the group consisting of hydrogen, halogen, $C_{1-2}$alkyl, $C_{1-2}$alkoxy, cyano, —C(O)O—$C_{1-2}$alkyl, —S—$C_{1-4}$alkyl and —SO$_2$—$C_{1-4}$alkyl. In another embodiment of the present invention, $R^6$ and $R^7$ are each independently absent or selected from the group consisting of hydrogen, halogen, $C_{1-4}$alkyl and halogenated $C_{1-2}$alkyl.

In an embodiment of the present invention, $R^6$ is selected from the group consisting of hydrogen, chloro, iodo, ethyl, methoxy, cyano, —C(O)O-methyl, —S-ethyl, —S-t-butyl and —SO$_2$-ethyl. In another embodiment of the present invention, $R^6$ is selected from the group consisting of hydrogen, iodo, chloro and —S-ethyl. In another embodiment of the present invention, $R^6$ is selected from the group consisting of hydrogen, chloro, ethyl and —SO$_2$-ethyl. In another embodiment of the present invention, $R^6$ is hydrogen.

In an embodiment of the present invention, $R^7$ is selected from the group consisting of hydrogen, chloro and ethyl. In another embodiment of the present invention, $R^7$ is selected from the group consisting of hydrogen and ethyl. In another embodiment of the present invention, $R^7$ is hydrogen.

In an embodiment of the present invention, (A)

is selected from the group consisting of

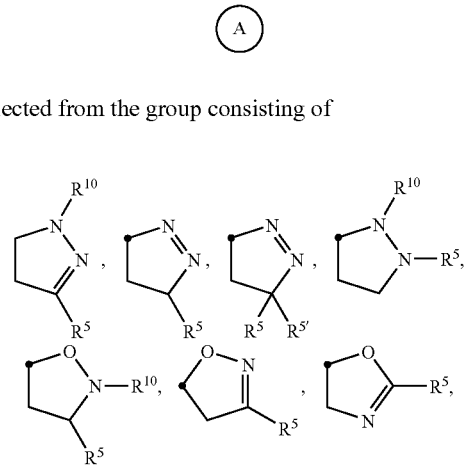

-continued

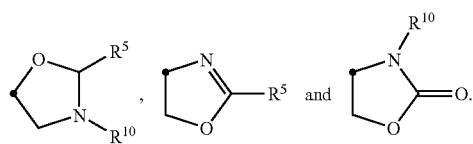

In another embodiment of the present invention,

Ⓐ is selected from the group consisting of

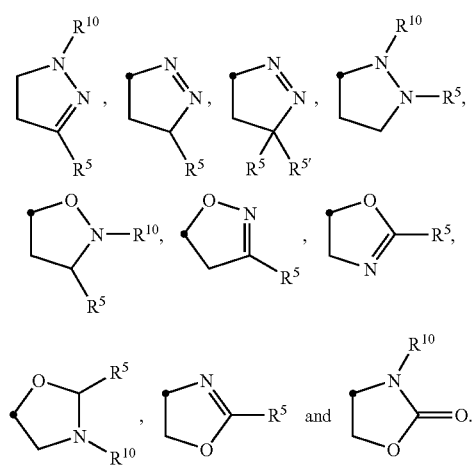

In another embodiment of the present invention,

Ⓐ is selected from the group consisting of

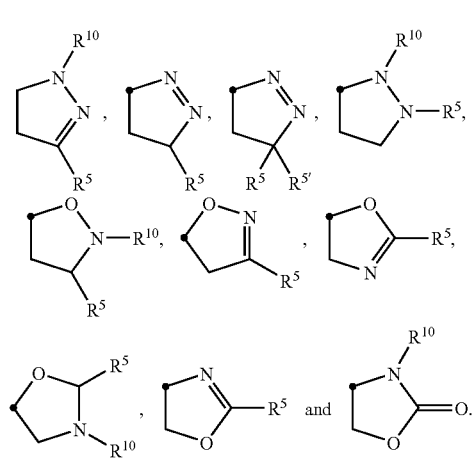

In another embodiment of the present invention,

Ⓐ is selected from the group consisting of

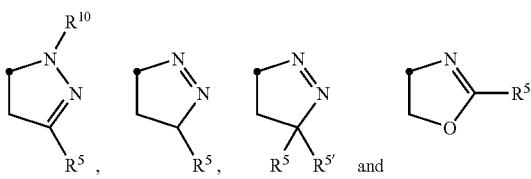

In another embodiment of the present invention,

Ⓐ is selected from the group consisting of

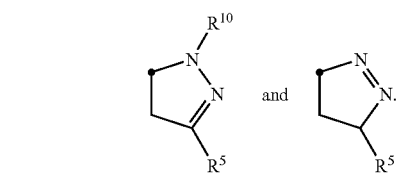

In another embodiment of the present invention,

Ⓐ is 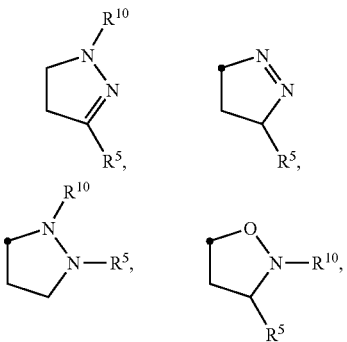.

In an embodiment of the present invention,

Ⓐ is selected from the group consisting of

-continued

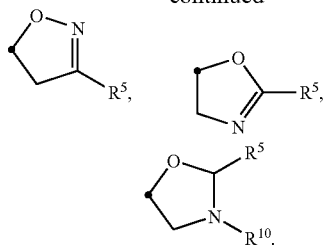

In another embodiment of the present invention, (A)

is selected from the group consisting of

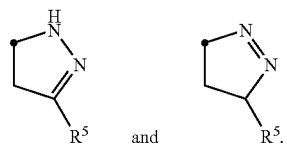

Preferably, (A) is 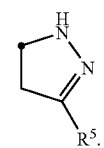

In an embodiment of the present invention, (A)

is selected from the group consisting of

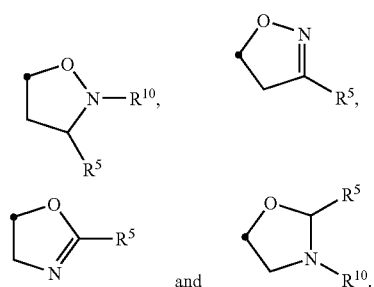

In another embodiment of the present invention, (A)

is selected from the group consisting of

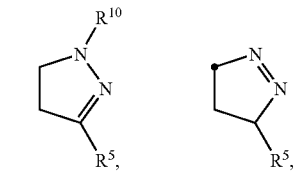

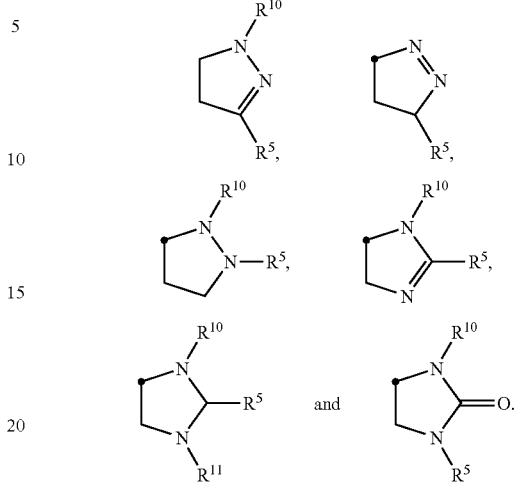

In yet another embodiment of the present invention, (A)

is selected from the group consisting of

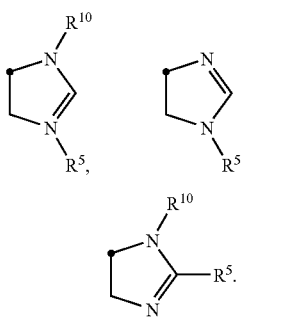

In yet another embodiment of the present invention, (A)

is selected from the group consisting of

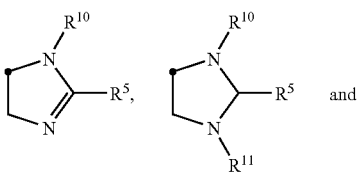

-continued

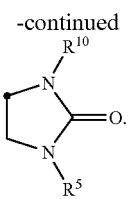

In an embodiment of the present invention, $R^{5'}$ is selected from the group consisting of halogen and $C_{1-2}$alkyl. In another embodiment of the present invention, $R^{5'}$ is selected from the group consisting of halogen and $C_{1-4}$alkyl. In another embodiment of the present invention, $R^{5'}$ is selected from the group consisting of halogen and $C_{1-2}$alkyl. In another embodiment, $R^{5'}$ is selected from the group consisting of chloro, bromo, idoo, methyl and ethyl. Preferably, $R^{5'}$ is chloro or methyl, more preferably, $R^{5'}$ is chloro.

In an embodiment of the present invention $R^{10}$ and $R^{11}$ are each independently selected from the group consisting of hydrogen, methyl and benzyl. Preferably, $R^{10}$ and $R^{11}$ are each independently selected from the group consisting of hydrogen and methyl.

In an embodiment of the present invention, $R^{10}$ is selected from hydrogen, $C_{1-4}$alkyl, benzyl or —C(O)—CF$_3$. In another embodiment of the present invention, $R^{10}$ is selected from the group consisting of hydrogen, $C_{1-4}$alkyl, benzyl and —C(O)—CF$_3$. In another embodiment of the present invention, $R^{10}$ is selected from the group consisting of hydrogen, $C_{1-2}$alkyl and benzyl. In another embodiment of the present invention, $R^{10}$ is selected from the group consisting of hydrogen, methyl and benzyl. In another embodiment of the present invention, $R^{10}$ is selected from the group consisting of hydrogen and $C_{1-4}$alkyl. In another embodiment of the present invention, $R^{10}$ is selected from the group consisting of hydrogen, methyl and ethyl. In another embodiment of the present invention, $R^{10}$ is selected from the group consisting of hydrogen and ethyl. In another embodiment of the present invention, $R^{10}$ is selected from the group consisting of hydrogen and methyl. Preferably, $R^{10}$ is hydrogen.

In an embodiment of the present invention, $R^5$ is selected from the group consisting of hydrogen, carboxy, alkyl, halogenated $C_{1-4}$alkyl, hydroxy substituted $C_{1-4}$alkyl, cycloalkyl, aryl, aralkyl, heteroaryl, heterocycloalkyl, —C(O)—$C_{1-4}$alkyl, —C(O)-(halogenated $C_{1-4}$alkyl), —C(O)O—$C_{1-4}$alkyl, —C(O)O-aryl, —$C_{1-4}$alkyl-S(O)$_{0-2}$—$C_{1-4}$alkyl, t-butyl-dimethyl-silyl and trimethylsilyl;

wherein the aryl, heteroaryl or heterocycloalkyl, whether alone or as part of a substituent group is optionally substituted with one or more substituents independently selected from the group consisting of halogen, hydroxy, $C_{1-4}$alkyl, $C_{1-4}$alkoxy, halogenated $C_{1-4}$alkyl, cyano, nitro, —NR$^C$—C(O)—$C_{1-4}$alkyl, NR$^C$—C(O)-(halogenated $C_{1-4}$alkyl), —C(O)O—$C_{1-4}$alkyl, trimethyl-silyl and t-butyl-dimethyl-silyloxy; wherein R$^C$ and R$^D$ are each independently selected from hydrogen or $C_{1-4}$alkyl.

In another embodiment of the present invention, $R^5$ is selected from the group consisting of hydrogen, carboxy, $C_{1-4}$alkyl, halogenated $C_{1-4}$alkyl, —$C_{1-4}$alkyl-OH, cycloalkyl, aryl, aralkyl, heteroaryl, heterocycloalkyl, —$C_{1-4}$alkyl-S—$C_{1-4}$alkyl, —C(O)O—$C_{1-4}$alkyl, —C(O)-(halogenated $C_{1-4}$alkyl) and trimethylsilyl;

wherein the aryl, whether alone or as part of a substituent group is optionally substituted with one or more substituents independently selected from hydroxy, halogen, $C_{1-4}$alkyl, —O—$C_{1-4}$alkyl, —C(O)O—$C_{1-4}$alkyl, —NH—C(O)—$C_{1-4}$alkyl, —NH—C(O)-(halogenated $C_{1-4}$alkyl) or t-butyl-dimethyl-silyloxy.

In another embodiment of the present invention, $R^5$ is selected from the group consisting of hydrogen, carboxy, methyl, ethyl, n-propyl, isopropyl, isobutyl, t-butyl, trifluoromethyl, 2,2,2-trifluoro-ethyl, 1,1,2,2,2-pentafluoro-ethyl, hydroxy-methyl-, 2-hydroxy-phenyl, 4-fluorophenyl, 3,4-difluorophenyl, 2,3,4,5,6-pentafluorophenyl, 4-ethylphenyl, 4-methoxy-phenyl, 2-hydroxy-3-fluoro-phenyl, 2-fluoro-3-hydroxy-phenyl, 3-methyl-4-fluoro-phenyl, cyclopentyl, cyclohexyl, 4-methoxy-carbonyl-phenyl, 3-methyl-carbonyl-amino-phenyl, 4-methyl-carbonyl-amino-phenyl, 4-(trifluoromethyl-carbonyl-amino)-phenyl, 2-(t-butyl-dimethyl-silyloxy)-3-fluoro-phenyl, t-butyl-dimethyl-silyloxy-phenyl, 4-methyl-carbonyl-amino-benzyl, 4-methyl-carbonyl-amino-phenyl, 2-furyl, 2-thienyl, 3-pyridyl, 2-tetrahydrofuryl, methyl-thio-ethyl-, ethyl-thio-ethyl-, ethoxy-carbonyl-, t-butoxy-carbonyl-, trifluoromethyl-carbonyl- and trimethyl-silyl.

Preferably, $R^5$ is selected from the group consisting of hydrogen, carboxy, methyl, ethyl, n-propyl, isopropyl, isobutyl, t-butyl, trifluoromethyl, 2,2,2-trifluoro-ethyl, 1,1,2,2,2-pentafluoro-ethyl, hydroxy-methyl-, 2-hydroxy-phenyl, 4-fluorophenyl, 3,4-difluorophenyl, 2,3,4,5,6-pentafluorophenyl, 4-ethylphenyl, 4-methoxy-phenyl, 2-hydroxy-3-fluoro-phenyl, 2-fluoro-3-hydroxy-phenyl, 3-methyl-4-fluoro-phenyl, cyclopentyl, cyclohexyl, 4-methoxy-carbonyl-phenyl, 3-methyl-carbonyl-amino-phenyl, 4-methyl-carbonyl-amino-phenyl, 4-(trifluoromethyl-carbonyl-amino)-phenyl, 2-(t-butyl-dimethyl-silyloxy)-3-fluoro-phenyl, t-butyl-dimethyl-silyloxy-phenyl, 4-methyl-carbonyl-amino-benzyl, 2-furyl, 2-thienyl, 3-pyridyl, 2-tetrahydrofuryl, methyl-thio-ethyl-, ethyl-thio-ethyl-, ethoxy-carbonyl-, t-butoxy-carbonyl-, trifluoromethyl-carbonyl- and trimethylsilyl.

In a embodiment of the present invention, $R^5$ is selected from the group consisting of halogenated $C_{1-2}$alkyl. In another embodiment of the present invention, $R^5$ is trifluoromethyl. In another embodiment of the present invention, $R^5$ is selected from the group consisting of halogenated $C_{1-4}$alkyl and aryl; wherein the aryl is optionally substituted with one to two halogen. Preferably, $R^5$ is selected from the group consisting of trifluoromethyl and 4-fluorophenyl.

In an embodiment of the present invention, $R^5$ is selected from the group consisting of methyl, trifluoromethyl, 1,1,2,2,2-pentafluoro-ethyl, —C(O)O-ethyl, 4-methyl-carbonyl-amino-phenyl, 4-trifluoromethyl-carbonyl-amino-phenyl and 4-methyl-carbonyl-amino-benzyl. In another embodiment of the present invention, $R^5$ is selected from the group consisting of hydrogen, n-propyl, isopropyl, trifluoromethyl, 4-fluorophenyl, 3,4-difluorophenyl, 2,3,4,5,6-pentafluorophenyl, 4-methoxyphenyl, 4-ethylphenyl, cyclohexyl, 2-furyl and 2-thienyl.

In an embodiment of the present invention are compounds of formula (I) selected from the group consisting of 3-Methyl-5-trifluoromethyl-3,4-dihydro-2H-pyrazole-3-carboxylic acid (4-cyano-3-trifluoromethyl-phenyl)-amide; 3-Ethyl-5-trifluoromethyl-3,4-dihydro-2H-pyrazole-3-carboxylic acid (4-cyano-3-trifluoromethyl-phenyl)-amide; 5-(4-Acetylamino-phenyl)-3-methyl-3,4-dihydro-2H-pyrazole-3-carboxylic acid (4-cyano-3-trifluoromethyl-phenyl)-amide;

5-(4-Acetylamino-phenyl)-3-methyl-3,4-dihydro-2H-pyrazole-3-carboxylic acid (4-nitro-3-trifluoromethyl-phenyl)-amide; 3-Methyl-5-[4-(2,2,2-trifluoro-acetylamino)-phenyl]-3,4-dihydro-2H-pyrazole-3-carboxylic acid (4-nitro-3-trifluoromethyl-phenyl)-amide; and pharmaceutically acceptable salts thereof.

In an embodiment of the present invention, the $R^1$ group on the compound of formula (I) or the compound of formula (II) is in the (R) stereo-configuration. In another embodiment of the present invention, the $R^1$ group on the compound of formula (I) or the compound of formula (II) is in the (S) stereo-configuration.

In another embodiment of the present invention is any single compound or subset of compounds selected from the representative compounds listed in Tables 1-4 below.

Additional embodiments of the present invention, include those wherein the substituents selected for one or more of the variables defined herein (i.e. $R^1$, $R^2$, $R^3$, $R^4$, $R^6$, $R^7$, W, Z, a,

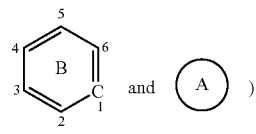

are independently selected to be any individual substituent or any subset of substituents selected from the complete list as defined herein.

Representative compounds of the present invention are as listed in Table 1-9 below. Unless otherwise noted, wherein a stereogenic center is present in the listed compound, the compound was prepared as a mixture of stereo-configurations. Where a stereogenic center is present, the (S) and (R) designations are intended to indicate that the exact stereo-configuration of the center has been determined.

TABLE 1

Representative Compounds of Formula (I)

| ID | $R^1$ | $R^3$ | $R^4$ | $R^{10}$ | $R^5$ |
|---|---|---|---|---|---|
| 1 | methyl | trifluoromethyl | cyano | H | 4-fluoro-phenyl |
| 2 | methyl | trifluoromethyl | cyano | H | 3,4-difluoro-phenyl |
| 3 | methyl | trifluoromethyl | cyano | H | 4-ethyl-phenyl |
| 4 | methyl | trifluoromethyl | cyano | H | 2-furyl |
| 5 | methyl | trifluoromethyl | cyano | benzyl | 4-fluoro-phenyl |
| 6 | methyl | trifluoromethyl | nitro | H | H |
| 7 | methyl | trifluoromethyl | nitro | H | 4-fluoro-phenyl |
| 8 | methyl | trifluoromethyl | cyano | H | trifluoromethyl |
| 9 | methyl | trifluoromethyl | cyano | H | 2,3,4,5,6-pentafluoro-phenyl |
| 10 | methyl | trifluoromethyl | cyano | H | 4-methoxy-phenyl |
| 11 | methyl | trifluoromethyl | cyano | H | isobutyl |
| 12 | methyl | trifluoromethyl | cyano | H | 2-fluoro-3-hydroxy-phenyl |
| 13 | methyl | trifluoromethyl | chloro | H | 4-fluoro-phenyl |
| 14 | methyl | trifluoromethyl | cyano | H | n-propyl |
| 15 | methyl | trifluoromethyl | cyano | H | ethyl |
| 16 | methyl | H | phenyl-carbonyl | H | H |
| 17 | methyl | H | phenyl-carbonyl | H | trifluoromethyl |
| 18 | methyl | H | benzyl | H | trifluoromethyl |
| 19 | methyl | H | phenyloxy- | H | trifluoromethyl |
| 20 | methyl | H | cyano | H | trifluoromethyl |
| 21 | methyl | H | cyano | H | H |
| 23 | methyl | trifluoromethyl | chloro | H | trifluoromethyl |
| 24 | methyl | chloro | chloro | H | trifluoromethyl |
| 25 | methyl | trifluoromethyl | cyano | H | cyclohexyl |
| 28 | methyl | H | phenyl-thio- | H | trifluoromethyl |
| 30 | ethyl | trifluoromethyl | cyano | H | trifluoromethyl |
| 32 | methyl | H | phenyl-sulfonyl | H | trifluoromethyl |
| 33 | methyl | trifluoromethyl | cyano | H | 4-methyl-carbonyl-amino-phenyl |
| 34 | methyl | trifluoromethyl | nitro | H | 4-methyl-carbonyl-amino-phenyl |
| 35 | (S)-methyl | trifluoromethyl | cyano | H | trifluoromethyl |
| 36 | (R)-methyl | trifluoromethyl | cyano | H | trifluoromethyl |
| 37 | methyl | trifluoromethyl | nitro | H | 4-(trifluoro-methyl-carbonyl-amino)-phenyl |
| 38 | methyl | cyano | cyano | H | 4-methyl-carbonyl-amino-phenyl |
| 39 | methyl | trifluoromethyl | cyano | methyl | 4-methyl-carbonyl-amino-phenyl |

TABLE 1-continued

Representative Compounds of Formula (I)

| ID | R$^1$ | R$^3$ | R$^4$ | R$^{10}$ | R$^5$ |
|---|---|---|---|---|---|
| 40 | methyl | trifluoromethyl | nitro | methyl | 4-methyl-carbonyl-amino-phenyl |
| 41 | methyl | trifluoromethyl | cyano | H | 3-methyl-carbonyl-amino-phenyl |
| 42 | methyl | trifluoromethyl | cyano | H | isopropyl |
| 43 | methyl | trifluoromethyl | cyano | H | 4-methyl-carbonyl-amino-benzyl |
| 44 | methyl | trifluoromethyl | chloro | H | 4-methyl-carbonyl-amino-phenyl |
| 45 | methyl | trifluoromethyl | cyano | H | 4-methoxy-carbonyl-phenyl |
| 46 | methyl | trifluoromethyl | chloro | H | 4-(trifluoro-methyl-carbonyl-amino)-phenyl |
| 47 | methyl | trifluoromethyl | cyano | H | H |
| 48 | methyl | chloro | chloro | H | H |
| 49 | methyl | trifluoromethyl | cyano | H | 2-thienyl |
| 52 | methyl | trifluoromethyl | cyano | H | 2-tetrahydro-furyl |
| 56 | methyl | trifluoromethyl | cyano | H | 3-methyl-4-fluoro-phenyl |
| 57 | methyl | trifluoromethyl | nitro | H | trimethyl-silyl |
| 73 | n-propyl | trifluoromethyl | cyano | H | trifluoromethyl |
| 74 | methyl | trifluoromethyl | nitro | H | trifluoromethyl |
| 75 | methyl | trifluoromethyl | cyano | H | 2,2,2-trifluoro-ethyl |
| 76 | methyl | trifluoromethyl | cyano | H | 2-hydroxy-phenyl |
| 77 | methyl | trifluoromethyl | cyano | H | 3-pyridyl |
| 78 | methyl | trifluoromethyl | cyano | H | cyclopentyl |
| 79 | methyl | trifluoromethyl | cyano | H | methyl-thio-ethyl- |
| 81 | (S)-ethyl | trifluoromethyl | cyano | H | trifluoromethyl |
| 82 | (R)-ethyl | trifluoromethyl | cyano | H | trifluoromethyl |
| 83 | methyl | trifluoromethyl | nitro | H | ethoxy-carbonyl- |
| 84 | methyl | trifluoromethyl | cyano | H | ethoxy-carbonyl- |
| 85 | methyl | trifluoromethyl | bromo | H | ethoxy-carbonyl- |
| 86 | methyl | trifluoromethyl | cyano | H | t-butyl |
| 87 | methyl | trifluoromethyl | cyano | H | ethyl-thio-ethyl- |
| 89 | methyl | trifluoromethyl | nitro | H | t-butyl |
| 90 | methyl | trifluoromethyl | cyano | H | t-butoxy-carbonyl- |
| 91 | methyl | trifluoromethyl | cyano | H | carboxy |
| 92 | methyl | trifluoromethyl | cyano | H | hydroxy-methyl- |
| 96 | methyl | trifluoromethyl | cyano | H | 2-(t-butyl-dimethyl-silyloxy)-3-fluoro-phenyl |
| 97 | methyl | trifluoromethyl | cyano | H | 2-hydroxy-3-fluoro-phenyl |
| 99 | methyl | trifluoromethyl | cyano | H | 1,1,2,2,2-pentafluoro-ethyl |
| 100 | methyl | trifluoromethyl | nitro | H | 1,1,2,2,2-pentafluoro-ethyl |
| 112 | trifluoro-methyl | trifluoromethyl | cyano | H | trifluoromethyl |
| 113 | trifluoro-methyl | trifluoromethyl | cyano | H | ethoxy-carbonyl- |
| 116 | trifluoro-methyl | trifluoromethyl | cyano | H | methyl |
| 119 | methyl | trifluoromethyl | bromo | H | trifluoromethyl |
| 120 | methyl | trifluoromethyl | cyano | ethyl | trifluoromethyl |
| 122 | (S)-methyl | trifluoromethyl | cyano | ethyl | trifluoromethyl |
| 123 | methyl | trifluoromethyl | cyano | methyl | trifluoromethyl |
| 125 | (R)-methyl | trifluoromethyl | cyano | ethyl | trifluoromethyl |
| 131 | methyl | trifluoromethyl | cyano | trifluoro-methyl-carbonyl | trifluoromethyl |
| 135 | methyl | trifluoromethyl | cyano | ethyl | 4-methyl-carbonyl-amino-phenyl |
| 146 | methyl | trifluoromethyl | cyano | ethyl | methyl |

TABLE 2

Representative Compounds of Formula (I)

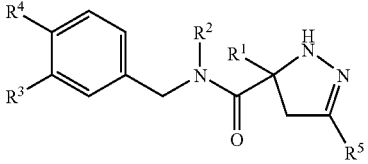

| ID | R¹ | R² | R³ | R⁴ | R⁵ |
|---|---|---|---|---|---|
| 22 | methyl | H | H | phenoxy | H |
| 26 | methyl | H | H | methyl-sulfonyl- | H |
| 27 | methyl | H | H | methyl-sulfonyl- | trifluoromethyl |
| 29 | methyl | H | H | chloro | trifluoromethyl |
| 115 | methyl | trifluoromethyl-carbonyl- | trifluoro-methyl | cyano | trifluoromethyl |
| 133 | methyl | methyl | trifluoro-methyl | cyano | trifluoromethyl |

TABLE 3

Representative Compounds of Formula (I)

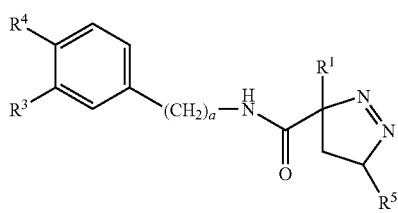

TABLE 3-continued

Representative Compounds of Formula (I)

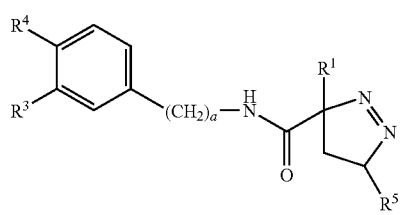

| ID | R¹ | a | R³ | R⁴ | R⁵ |
|---|---|---|---|---|---|
| 51 | methyl | 0 | trifluoromethyl | cyano | trimethyl-silyl |
| 53 | methyl | 0 | trifluoromethyl | cyano | 3,4-difluorophenyl |
| 54 | methyl | 0 | trifluoromethyl | cyano | 2-t-butyl-dimethylsilyloxy-phenyl |
| 55 | methyl | 0 | trifluoromethyl | cyano | 2-hydroxy-phenyl |
| 58 | methyl | 0 | trifluoromethyl | cyano | ethyl |
| 59 | methyl | 0 | trifluoromethyl | cyano | methyl-thio-ethyl |
| 60 | methyl | 0 | trifluoromethyl | cyano | methyl |
| 61 | methyl | 0 | trifluoromethyl | cyano | isobutyl |
| 62 | methyl | 0 | trifluoromethyl | cyano | n-propyl |
| 63 | methyl | 0 | H | phenyl-carbonyl | trimethyl-silyl |
| 64 | methyl | 0 | trifluoromethyl | cyano | 4-fluoro-phenyl |
| 65 | methyl | 0 | H | cyano | trimethyl-silyl |
| 66 | methyl | 1 | H | phenyloxy- | trimethyl-silyl |
| 67 | methyl | 1 | H | methyl-sulfonyl | trimethyl-silyl |
| 68 | methyl | 0 | trifluoromethyl | cyano | cyclohexyl |
| 69 | methyl | 0 | trifluoromethyl | cyano | isopropyl |
| 98 | methyl | 0 | trifluoromethyl | cyano | methyl |
| 114 | trifluoromethyl | 0 | trifluoromethyl | cyano | methyl |

TABLE 4

Representative Compounds of Formula (I)

| ID | A | R¹ | R³ | R⁴ | R⁵ |
|---|---|---|---|---|---|
| 70 | 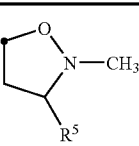 | methyl | trifluoromethyl | cyano | 4-methyl-carbonyl-amino-phenyl |

TABLE 4-continued

Representative Compounds of Formula (I)

| ID | A | R¹ | R³ | R⁴ | R⁵ |
|----|---|----|----|----|----|
| 71 | isoxazolidine N-CH₃, R⁵ | methyl | trifluoromethyl | nitro | 4-methyl-carbonyl-amino-phenyl |
| 72 | oxazolidine-R⁵ | methyl | trifluoromethyl | cyano | 4-methyl-carbonyl-amino-phenyl |
| 95 | isoxazoline-R⁵ | methyl | trifluoromethyl | cyano | 4-fluoro-phenyl |
| 103 | oxazoline-R⁵ | methyl | trifluoromethyl | cyano | methyl |
| 104 | oxazoline-R⁵ | methyl | chloro | chloro | methyl |
| 105 | oxazoline-R⁵ | methyl | H | cyano | methyl |
| 101 | pyrazolidine N-R⁵ | methyl | trifluoromethyl | cyano | H |
| 102 | pyrazolidine N-R⁵ | methyl | trifluoromethyl | cyano | trifluoro-methyl-carbonyl- |
| 107 | pyrazolidine N-R⁵ | methyl | trifluoromethyl | cyano | 4-methyl-carbonyl-amino-benzyl |
| 110 | oxazoline-R⁵ | methyl | trifluoromethyl | cyano | trifluoromethyl |
| 111 | oxazolidinone | methyl | trifluoromethyl | cyano | absent |

TABLE 4-continued

Representative Compounds of Formula (I)

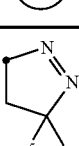

| ID | A | R¹ | R³ | R⁴ | R⁵ |
|---|---|---|---|---|---|
| 124 | (pyrazoline with R⁵, Cl) | methyl | trifluoromethyl | cyano | trifluoromethyl |
| 134 | (isoxazoline with R⁵) | methyl | trifluoromethyl | cyano | methyl |

TABLE 5

Representative Compounds of formula (I)

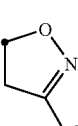

| ID No. | A | R⁵ | R¹ | R² | R⁶ | R⁷ |
|---|---|---|---|---|---|---|
| 126 | (pyrazoline with R⁵) | | trifluoromethyl | methyl | H | iodo | H |
| 127 | (pyrazoline with R⁵) | | trifluoromethyl | methyl | H | H | ethyl |
| 128 | (pyrazoline with R⁵) | | trifluoromethyl | methyl | H | ethyl | H |
| 129 | (pyrazoline with R⁵) | | trifluoromethyl | methyl | H | cyano | H |

TABLE 5-continued

Representative Compounds of formula (I)

| ID No. | A | R⁵ | R¹ | R² | R⁶ | R⁷ |
|---|---|---|---|---|---|---|
| 130 | 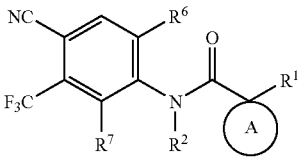 | trifluoromethyl | methyl | H | chloro | H |
| 137 | 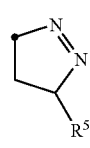 | trifluoromethyl | methyl | H | chloro | chloro |
| 138 | 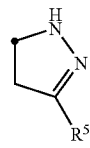 | trifluoromethyl | methyl | trifluoro-ethyl | chloro | chloro |
| 139 | 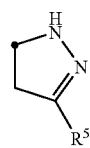 | trifluoromethyl | methyl | H | chloro | chloro |
| 140 | 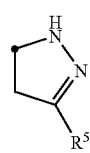 | trifluoromethyl | methyl | H | ethyl-thio- | H |
| 141 | 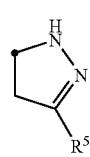 | trifluoromethyl | methyl | H | methoxy | H |
| 142 | 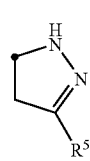 | trifluoromethyl | methyl | H | ethyl-sulfonyl- | H |
| 143 | 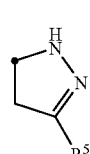 | trifluoromethyl | methyl | H | t-butyl-thio- | H |

TABLE 6

Representative Compounds of Formula (I)

| ID No. | A | R⁵ | R¹ | R² | R⁶ | R⁷ |
|---|---|---|---|---|---|---|
| 147 |  | H | H | methyl | H | methoxy-carbonyl- | H |

TABLE 7

Representative Compounds of Formula (I)

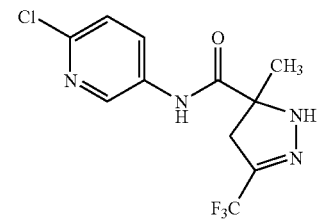

| ID No. | A | R⁵ | R¹ | R³ | R⁴ |
|---|---|---|---|---|---|
| 118 | 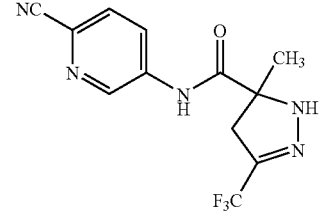 | trifluoromethyl | methyl | trifluoromethyl | cyano |
| 136 | 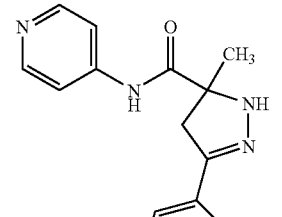 | trifluoromethyl | methyl | chloro | chloro |
| 144 | 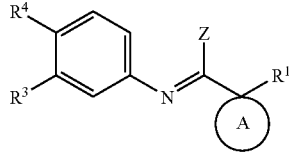 | trifluoromethyl | (R)-methyl | trifluoromethyl | cyano |
| 145 |  | trifluoromethyl | (S)-methyl | trifluoromethyl | cyano |

TABLE 8

Representative Compounds of Formula (I)

| ID No | Structure |
|---|---|
| 80 | 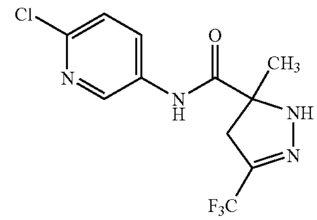 |
| 88 | 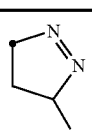 |
| 93 | 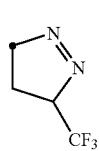 |

Representative compounds of formula (II) are as listed in Table 9 below. For convenience only one tautomeric form of the compounds listed below is specifically shown in Table 9.

TABLE 9

Representative Compounds of Formula (II)

| ID No. | A | R¹ | R³ | R⁴ | Z |
|---|---|---|---|---|---|
| 200 | (pyrazoline with CF₃) | methyl | trifluoromethyl | cyano | —O-ethyl |
| 201 | (pyrazoline with CF₃) | (S)-methyl | trifluoromethyl | cyano | —O-ethyl |

TABLE 9-continued

Representative Compounds of Formula (II)

| ID No. | A | R¹ | R³ | R⁴ | Z |
|---|---|---|---|---|---|
| 202 | 4,5-dihydro-3-(trifluoromethyl)pyrazol-1-yl (N=N) | (S)-methyl | trifluoromethyl | cyano | —O-ethyl |
| 203 | N-methyl pyrazolinyl-CF₃ | methyl | trifluoromethyl | cyano | —O-methyl |
| 204 | NH pyrazolinyl-CF₃ | methyl | trifluoromethyl | cyano | —S-ethyl |
| 205 | NH pyrazolinyl-CF₃ | methyl | trifluoromethyl | cyano | —NH-ethyl |
| 206 | NH pyrazolinyl-CF₃ | methyl | trifluoromethyl | cyano | —NH—OH |
| 207 | NH pyrazolinyl-CF₃ | methyl | trifluoromethyl | cyano | —NH₂ |
| 208 | NH pyrazolinyl-CF₃ | methyl | trifluoromethyl | cyano | —N(ethyl)₂ |
| 209 | NH pyrazolinyl-CF₃ | methyl | trifluoromethyl | cyano | 1-pyrrolidinyl |
| 210 | NH pyrazolinyl-CF₃ | methyl | trifluoromethyl | cyano | —NH—O-methyl |
| 211 | NH pyrazolinyl-CF₃ | methyl | trifluoromethyl | cyano | —NH-methyl |
| 212 | NH pyrazolinyl-CF₃ | methyl | trifluoromethyl | cyano | —O-methyl |
| 213 | NH pyrazolinyl-CF₃ | methyl | chloro | chloro | —S-ethyl |
| 214 | NH pyrazolinyl-CF₃ | methyl | trifluoromethyl | cyano | —NH—SO₂-methyl |
| 215 | NH pyrazolinyl-CF₃ | (R)-methyl | trifluoromethyl | cyano | —S-ethyl |
| 216 | NH pyrazolinyl-CF₃ | (S)-methyl | trifluoromethyl | cyano | —S-ethyl |
| 217 | N-methyl pyrazolinyl-CF₃ | (S)-methyl | trifluoromethyl | cyano | —NH-cyano |

TABLE 9-continued

Representative Compounds of Formula (II)

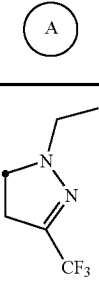

| ID No. | A | R¹ | R³ | R⁴ | Z |
|--------|---|-----|-----|-----|---|
| 218 | <img> | (S)-methyl | trifluoromethyl | cyano | —S-ethyl |

One skilled in the art will recognize that in the recitation of the substituent groups of

the "●" symbol is intended to denote the point of attachment of the

ring to the rest of the molecule.

One skilled in the art will further recognize that in the drawing of the substituent group

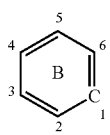

in the compounds of formula (I) and compounds of formula (II), the "C" within the ring structure is intended to indicate a carbon atom. Thus when

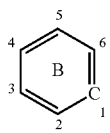

is other than phenyl, the

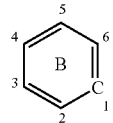

ring is attached to the —$(CH_2)_a$— portion of the compounds of formula (I) through a carbon atom. One skilled in the art will further recognize that the

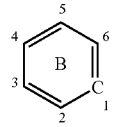

substituent group further indicates the numbering of the atoms on the ring. More specifically, the "C" carbon atom is counted as 1, with the other atoms numbered (counted off) in a clockwise fashion. Thus for example, wherein the

substituent group is other than phenyl, for example pyridyl, as in the following representative compound of formula (I)

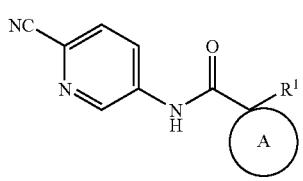

the

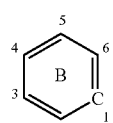

substituent group is 3-pyridyl, substituted with a cyano group at the 4-position.

As used herein, "halogen" shall mean chlorine, bromine, fluorine and iodine.

As used herein, unless otherwise noted, the abbreviation "$C_{a-b}$" wherein a and b are integers, is intended to denote the number of carbon atoms within the substituent group. For example, $C_{1-4}$alkyl denotes alkyl chains containing one (1) to four (4) carbon atoms. Similarly, $C_{2-4}$alkenyl, denotes an alkenyl chain containing two (2) to four (4) carbon atoms.

As used herein, the term "alkyl" whether used alone or as part of a substituent group, include straight and branched chains. For example, alkyl radicals include methyl, ethyl, propyl, isopropyl, butyl, isobutyl, sec-butyl, t-butyl, pentyl and the like.

As used herein, unless otherwise noted, the term "halogenated $C_{1-4}$alkyl" shall mean any straight or branched alkyl chain comprising one to four carbon atoms wherein the alkyl chain is substituted with one or more, preferably one to five, more preferably one to three halogen atoms, and wherein the halogen atoms are independently selected from chloro, bromo, fluoro or iodo, preferably chloro or fluoro, more preferably fluoro. Suitable examples include, but are not limited to trifluoromethyl, 2,2,2-trifluoroethyl, 1,1,2,2,2-pentafluoroethyl, and the like. Preferably, the halogenated $C_{1-4}$alkyl is trifluoromethyl or 1-(2,2,2-trifluoroethyl), more preferably, trifluoromethyl.

As used herein, unless otherwise noted, the term "alkenyl" shall include straight and branched chains comprising at least one unsaturated double bond. Suitable examples include, but are not limited to, vinyl, 1-propenyl, and the like. Preferably, the alkenyl group contains one unsaturated double bond.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, "aryl" shall refer to unsubstituted carbocylic aromatic groups such as phenyl, naphthyl, and the like.

As used herein, unless otherwise noted, the term "cycloalkyl" shall mean any stable 3-8 membered monocyclic, saturated ring system, for example cyclopropyl, cyclobutyl, cyclopentyl, cyclohexyl, cycloheptyl and cyclooctyl.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

As used herein, the term "heterocycloalkyl" shall denote any five to seven membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic bicyclic ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure.

Examples of suitable heterocycloalkyl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, and the like.

As used herein, unless otherwise noted the term "5 or 6 membered, saturated, heterocyclic ring structure" shall mean any stable ring structure comprising 5 to 6 ring atoms independently selected from C, N, O and S, wherein the ring structure does not contain any unsaturated bonds. Preferably, the 5 to 6 membered, saturated heterocyclic ring structure contains one to two ring atoms selected from the group consisting of N, O and S (wherein the remaining ring atoms are C). More preferably, the 5 or 6 membered, saturated, heterocyclic ring structure contains one nitrogen ring atom and optionally contains an additional ring atom selected from the group consisting of O, N and S (wherein the remaining ring atoms are C). Suitable examples include, but are not limited to pyrrolidinyl, piperidinyl, piperazinyl, morpholinyl, pyrazolidinyl, and the like; preferably pyrrolidinyl.

As used herein, the notation "*" shall denote the presence of a stereogenic center.

When a particular group is "substituted" (e.g., alkyl, aryl, cycloalkyl, heterocycloalkyl, heteroaryl), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "aprotic solvent" shall mean any solvent that does not yield a proton. Suitable examples include, but are not limited to DMF, dioxane, THF, acetonitrile, pyridine, dichloroethane, dichloromethane, MTBE, toluene, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

Under standard nomenclature used throughout this disclosure, the terminal portion of the designated side chain is described first, followed by the adjacent functionality toward the point of attachment. Thus, for example, a "phenylC$_1$-C$_6$alkylaminocarbonylC$_1$-C$_6$alkyl" substituent refers to a group of the formula

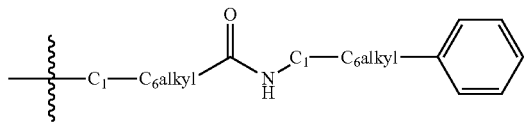

Abbreviations used in the specification, particularly the Schemes and Examples, are as follows:
Ac=Acetyl (i.e. —C(O)CH$_3$)
AcOH=Acetic acid
CDI=N,N'-Carbonyl-Diimidazole
CSA=Camphor sulfonic acid
DCC=N,N'-Dicyclohexyl-carbodiimide
DCM=Dichloromethane
DIPEA or DIEA=Diisopropylethylamine
DMA N,N-Dimethylacetamide
DMF=N,N-Dimethylformamide
DMSO=Dimethylsulfoxide
EDC=1,2-Dichloroethane
Et=Ethyl
Et$_3$N=Triethylamine
Et$_2$O=Diethyl ether
EtOAc=Ethyl acetate
LiHMDS=Lithium Hexamethyldisilazinamide
Me=methyl
MeOH=Methanol
NCS=N-chlorosuccinimide
NMP=1-Methyl-2-pyrrolidinone
OXONE®=Potassium monopersulphate triple salt
Pd—C or Pd/C=Palladium on Carbon Catalyst
PdCl$_2$(PPh$_3$)$_2$=Palladium Bis(triphenylphosphine) chloride
PTSA or pTSA=p-Toluene sulfonic acid
PyBroP=Bromortri(pyrrolidino)phosphonium hexafluorophosphate
TBAF=Tetra(n-butyl)ammonium fluoride
TEA=Triethylamine
Tf=Triflate
TFA=Trifluoroacetic Acid
TFAA=Trifluoroacetic acid anhydride
THF=Tetrahydrofuran
TMS=Trimethylsilyl
TMSCHN$_2$=Trimethylsilyl diazomethane
Ts=tosyl (—SO$_2$— (p-toluene))

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edentate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Compounds of formula (I) wherein

is selected from

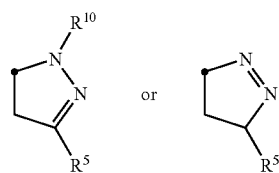

may be prepared according to the process outlined in Scheme 1.

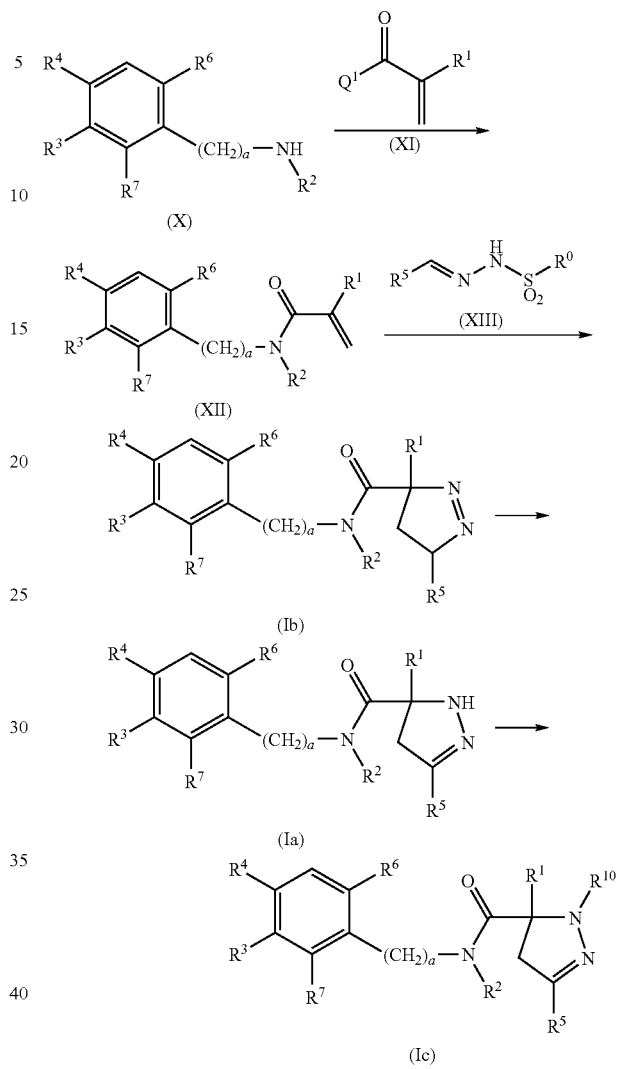

Accordingly, a suitably substituted compound of formula (X), a known compound or compound prepared by known methods, is reacted with a suitably substituted compound of formula (XI), wherein $Q^1$ is a suitable leaving group such as hydroxy, halogen, and the like, a known compound or compound prepared by known methods, according to known methods (for example, where Q is a halogen, in an organic solvent such as THF, methylene chloride, and the like; where Q is hydroxy, in the presence of cyanochloride, oxalyl chloride, and the like, in an organic solvent such as DMA, DMF, and the like), to yield the corresponding compound of formula (XII).

The compound of formula (XII) is reacted with a suitably substituted and protected hydrazone, a compound of formula (XIII), wherein $R^0$ a group such as tolyl, and the like, (wherein —$SO_2$—$R^0$ is a leaving group), a known compound or compound prepared by known methods, in the presence of a base such as NaH, potassium t-butoxide, and the like, in an organic solvent such as THF, dioxane, and the like, at a temperature in the range of from about room temperature to about reflux temperature, preferably at a temperature in the range of from about 80 to about 100° C., to yield the corresponding compound of formula (Ib).

The compound of formula (Ib) is further, optionally converted to the corresponding compound of formula (Ia) by treating the compound of formula (Ib) with a weak acid such as acetic acid, TFA, dilute HCl, and the like, or by passing the compound of formula (Ib) through silica gel, according to known methods.

The compound of formula (Ia) is further, optionally reacted with a suitably substituted alkylating agent, according to known methods, to yield the corresponding compound of formula (Ic).

One skilled in the art will recognize that compounds of formula (I) wherein

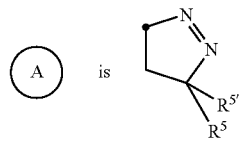

and wherein $R^{5'}$ is $C_{1-4}$alkyl may be similarly prepared according to the process described in Scheme 1 by selecting and substituting a suitably substituted compound of formula (XXXX)

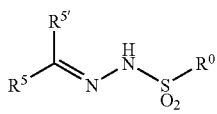
(XXXX)

for the compound of formula (XIII) above.
Compounds of formula (I) wherein

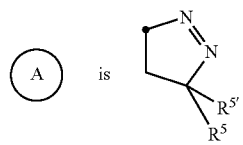

and $R^{5'}$ is halogen may be prepared from the corresponding compound of formula (I) wherein

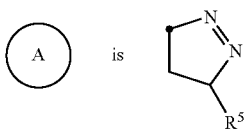

by reacting with a suitable source of the halogen (for example, wherein the halogen is chloro by reacting with $PCl_5$ or $POCl_3$) according to known methods.

Compounds of formula (I) wherein

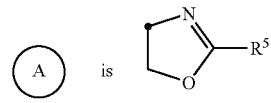

may be similarly prepared according to the process outlined in Scheme 1 above, by selecting and substituting a suitably substituted compound of formula (XXXXI)

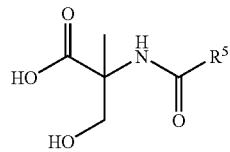
(XXXXI)

for the compound of formula (XIII).
Compounds of formula (I) wherein

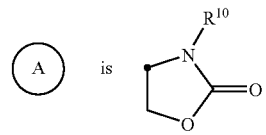

may be similarly prepared according to the process outlined in Scheme 1 above, by selecting and substituting a suitably substituted compound of formula (XXXXII)

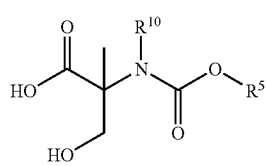
(XXXXII)

for the compound of formula (XIII).
Compounds of formula (Ic) wherein $R^{10}$ is other than hydrogen may alternatively be prepared according to the process outline in Scheme 2.

Scheme 2

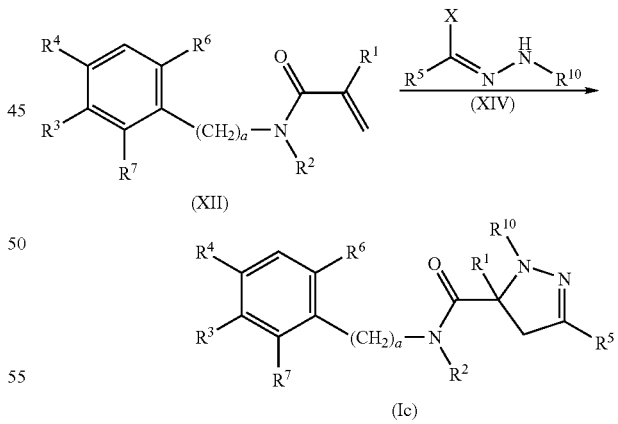

Accordingly, a suitably substituted compound of formula (XII) is reacted with a suitably substituted hydrazine, a compound of formula (XIV), wherein X is Cl or Br, a known compound or compound prepared by known methods, in the presence of an organic amine base such as TEA, DIPEA, pyridine, and the like, in an organic solvent such as THF, dioxane, and the like, at a temperature in the range of about 0 to about 50° C., preferably at about room temperature, to yield the corresponding compound of formula (Ic).

Compounds of formula (I) wherein

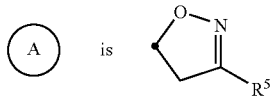

may be prepared according to the process outlined in Scheme 3.

Scheme 3

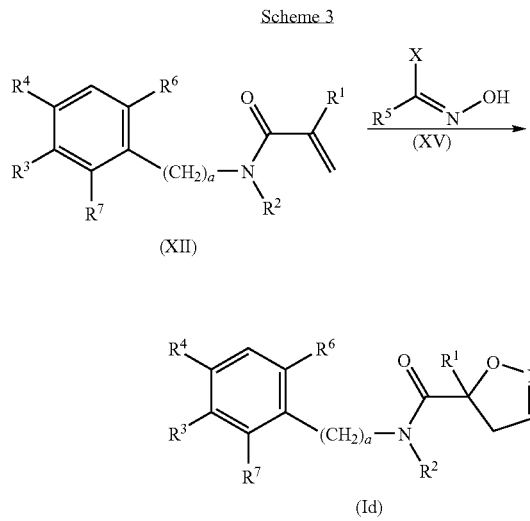

Accordingly, a suitably substituted compound of formula (XII) is reacted with a suitably substituted compound of formula (XV), wherein X is Cl or Br, a known compound or compound prepared by known methods, in the presence of an organic amine base such as TEA, DIPEA, pyridine, and the like, in an organic solvent such as THF, dioxane, and the like, at a temperature in the range of about 0 to about 50° C., preferably at about room temperature, to yield the corresponding compound of formula (Id).

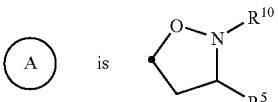

Compounds of formula (I) wherein may be prepared according to the process outlined in Scheme 4.

Scheme 4

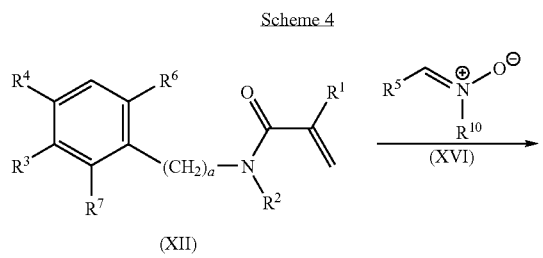

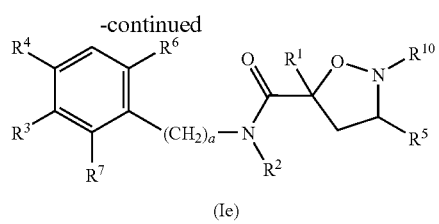

Accordingly, a suitably substituted compound of formula (XII) is reacted with a suitably substituted compound of formula (XVI), a known compound or compound prepared by known methods, in an organic solvent such as toluene, xylene, chlorobenzene, and the like, at a temperature in the range of about room temperature to about 120° C., to yield the corresponding compound of formula (Ie).

Compounds of formula (I) wherein

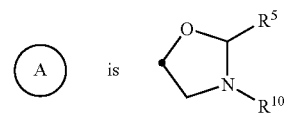

may be prepared according to the process outlined in Scheme 5.

Scheme 5

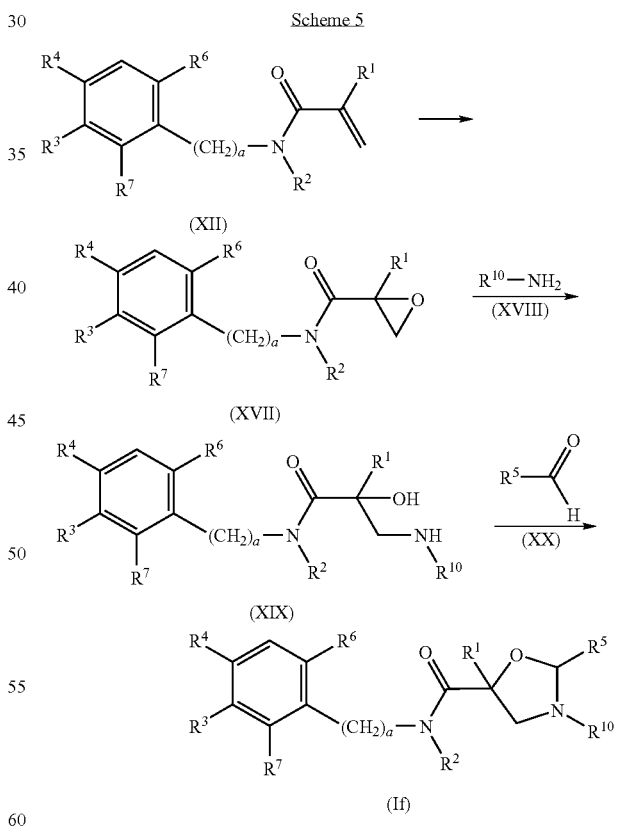

Accordingly, a suitably substituted compound of formula (XII) is reacted with a suitable reducing agent such as mCPBA, hydrogen peroxide, and the like, at a temperature in the range of about 0° C. to about room temperature, according to known methods, to yield the corresponding compound of formula (XVII).

The compound of formula (XVII) is reacted with a suitably substituted amine, a compound of formula (XVIII), a known compound or compound prepared by known methods, in an organic solvent such as DMF, DMSO, and the like, at a temperature in the range of about 0 to about 50° C., preferably at about room temperature, to yield the corresponding compound of formula (XIX).

The compound of formula (XIX) is reacted with a suitably substituted compound of formula (XX), a known compound or compound prepared by known methods, in the presence of an acid such as PTSA, CSA, and the like, in an organic solvent such as toluene, and the like or in an alcohol such as methanol, ethanol, and the like, at a temperature in the range of about 0 to about 50° C., preferably at about room temperature, to yield the corresponding compound of formula (If).

Compounds of formula (I) wherein

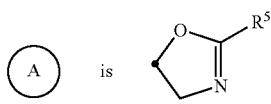

may be prepared according to the process outlined in Scheme 6.

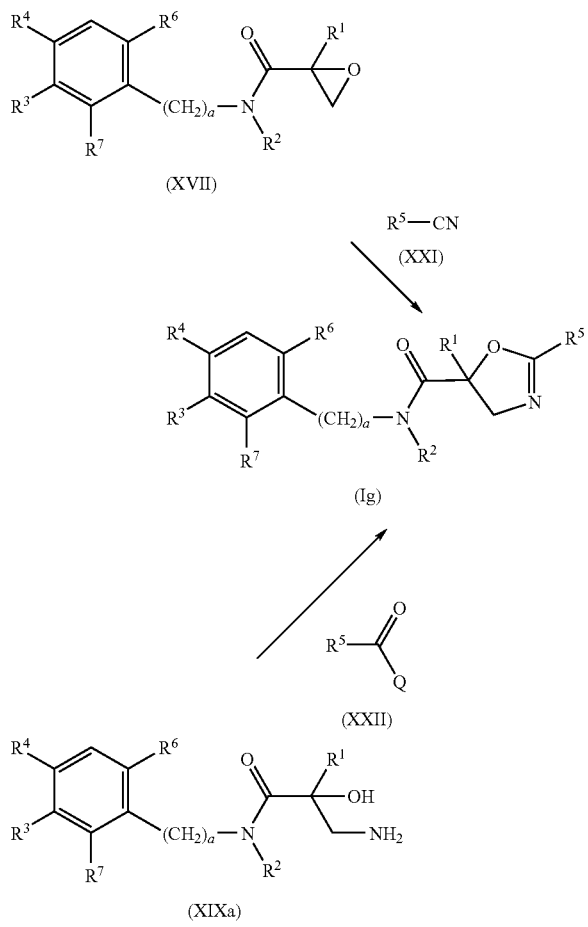

Accordingly, a suitably substituted compound of formula (XVII) is reacted with a suitably substituted compound of formula (XXI), a known compound or compound prepared by known methods, in the presence of a Lewis acid such as $BF_3$.Etherate, $AlCl_3$, and the like, in an organic solvent such as methylene chloride, chloroform, and the like, to yield the corresponding compound of formula (Ig).

Alternatively, a suitably substituted compound of formula (XIXa), a compound of formula (XIX) wherein $R^{10}$ is hydrogen, is reacted with a suitably substituted compound of formula (XXII), wherein Q is a leaving group such as hydroxy, halogen, and the like, a known compound or compound prepared by known methods, according to known methods, at an elevated temperature in the range of from about 50 to about 120° C., preferably at an elevated temperature in the range of about 80 to about 120° C., to yield the corresponding compound of formula (Ig).

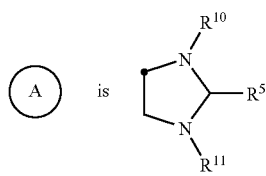

Compounds of formula (I) wherein may be prepared according to the process outlined in Scheme 7.

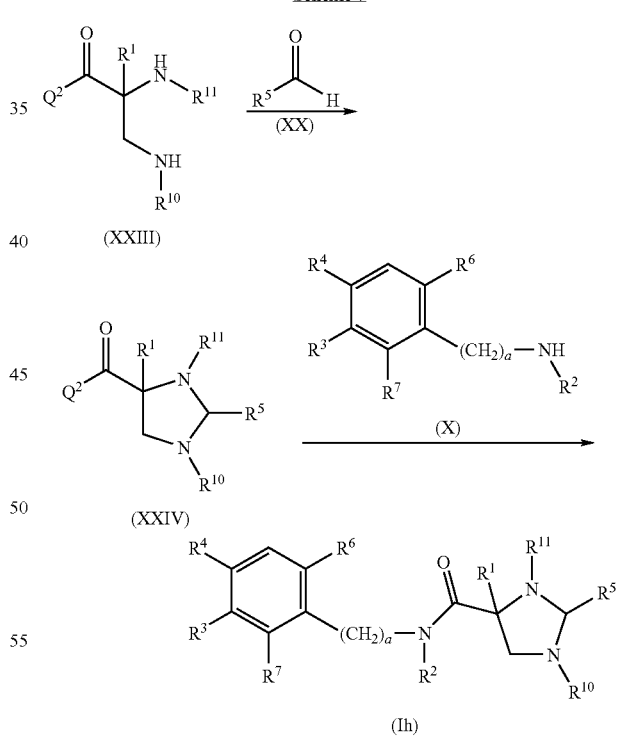

Accordingly, a suitably substituted compound of formula (XXIII), wherein $Q^2$ is suitable leaving group such as OH, halogen, alkoxy, alkyl-carbonyl-oxy-, and the like, is reacted with a suitably substituted aldehyde, a compound of formula (XX), a known compound or compound prepared by known methods, in the presence of an acid such as PTSA, CSA, and the like, in an organic solvent such as toluene, benzene, and the like, at a temperature in the range of from about room temperature to about 50° C., to yield the corresponding compound of formula (XXIV).

Wherein the compound of formula (XXIV) Q² is alkoxy and the like, the compound of formula (XXIV) is reacted with a suitably substituted compound of formula (X), a known compound or compound prepared by known methods, in the presence of a metallic agent such as $(CH_3)_3Al$, isopropyl-MgCl, and the like, in an organic solvent such as toluene, THF, and the like, at a temperature in the range of from about 0° C. to about room temperature, to yield the corresponding compound of formula (Ih).

Alternatively, wherein the compound of formula (XXIV) Q² is hydroxy, the compound of formula (XXIV) is reacted with a suitably substituted compound of formula (X), a known compound or compound prepared by known methods, in the presence of a coupling agent such as DCC, EDC, PyBroP, and the like, in the presence of an organic amine such as TEA, DIPEA, pyridine, and the like, in an organic solvent such as DCM, THF, and the like, at a temperature in the range of from about room temperature to about 50° C., to yield the corresponding compound of formula (Ih).

Compounds of formula (I) wherein

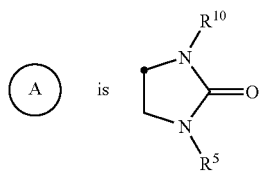

may be prepared according to the process outlined in Scheme 8.

Accordingly, a suitably substituted compound of formula (XXV), wherein Q³ is a suitable leaving group such as hydroxy, halogen, alkoxy, and the like, is reacted with 1,1'carbonyl-diimidazole (CDI), in the presence of an organic amine such as TEA, DIPEA, pyridine, and the like, to yield the corresponding compound of formula (XXVI).

Wherein the compound of formula (XXVI) Q³ is alkoxy and the like, the compound of formula (XXVI) is reacted with a suitably substituted compound of formula (X), a known compound or compound prepared by known methods, in the presence of a metallic agent such as $(CH_3)_3Al$, isopropyl-MgCl, and the like, in an organic solvent such as toluene, THF, and the like, at a temperature in the range of from about 0° C. to about room temperature, to yield the corresponding compound of formula (Ij).

Alternatively, wherein the compound of formula (XXVI) Q³ is hydroxy, the compound of formula (XXVI) is reacted with a suitably substituted compound of formula (X), a known compound or compound prepared by known methods, in the presence of a coupling agent such as DCC, EDC, PyBroP, and the like, in the presence of an organic amine such as TEA, DIPEA, pyridine, and the like, in an organic solvent such as DCM, THF, and the like, at a temperature in the range of from about room temperature to about 50° C., to yield the corresponding compound of formula (Ij).

Compounds of formula (I) wherein

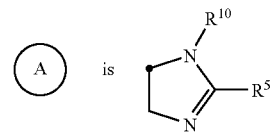

may be prepared according to the process outlined in Scheme 9.

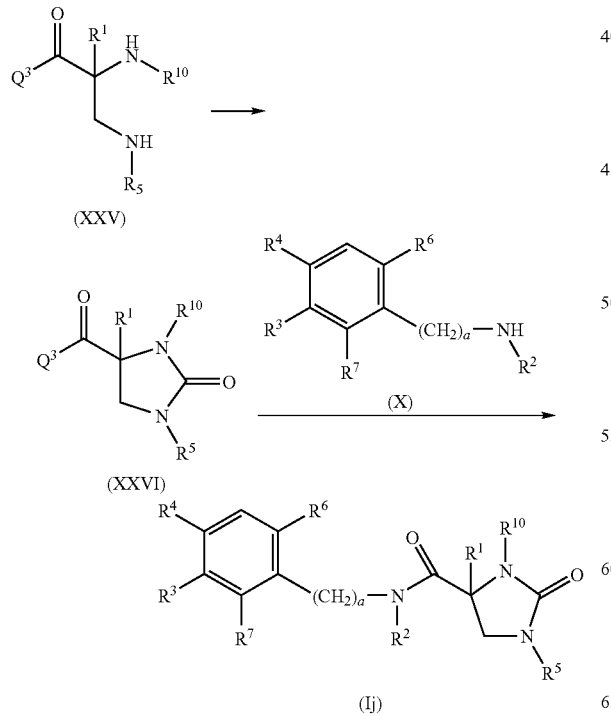

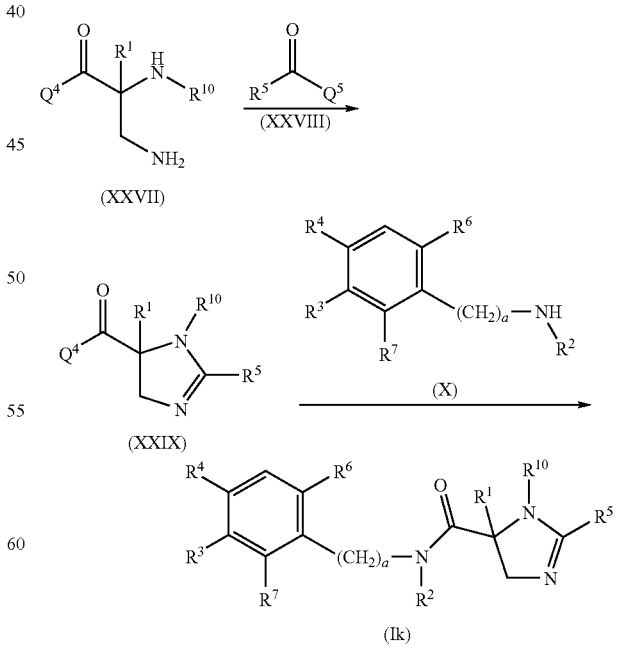

Accordingly, a suitably substituted compound of formula (XXVII), wherein Q⁴ is a suitable leaving group such as OH, halogen, alkoxy, alkyl-carbonyl-oxy-, and the like, a known compound or compound prepared by known methods, is reacted with a suitably substituted compound of formula (XXVIII), wherein $Q^5$ is a suitable leaving group such as OH, halogen, alkoxy, alkyl-carbonyl-oxy-, and the like, a known compound or compound prepared by known methods, in the presence of a coupling agent such as DCC, EDC, PyBroP, and the like, in the presence of an acid such as PTSA, CSA, and the like, in an organic solvent such as THF, toluene, benzene, and the like, at a temperature in the range of from about 50 to about 80° C., to yield the corresponding compound of formula (XXIX).

Wherein the compound of formula (XXIX) $Q^4$ is alkoxy and the like, the compound of formula (XXIX) is reacted with a suitably substituted compound of formula (X), a known compound or compound prepared by known methods, in the presence of a metallic agent such as $(CH_3)_3Al$, isopropyl-MgCl, and the like, in an organic solvent such as toluene, THF, and the like, at a temperature in the range of from about 0° C. to about room temperature, to yield the corresponding compound of formula (Ik).

Alternatively, wherein the compound of formula (XXIX) $Q^4$ is hydroxy, the compound of formula (XXIX) is reacted with a suitably substituted compound of formula (X), a known compound or compound prepared by known methods, in the presence of a coupling agent such as DCC, EDC, PyBroP, and the like, in the presence of an organic amine such as TEA, DIPEA, pyridine, and the like, in an organic solvent such as DCM, THF, and the like, at a temperature in the range of from about room temperature to about 50° C., to yield the corresponding compound of formula (Ik).

Compounds of formula (I) wherein

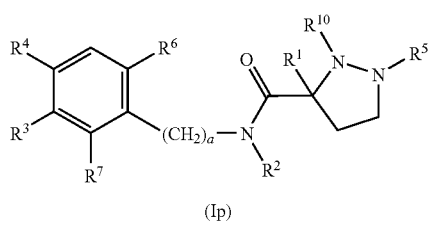

may be prepared according to the process outlined in Scheme 10.

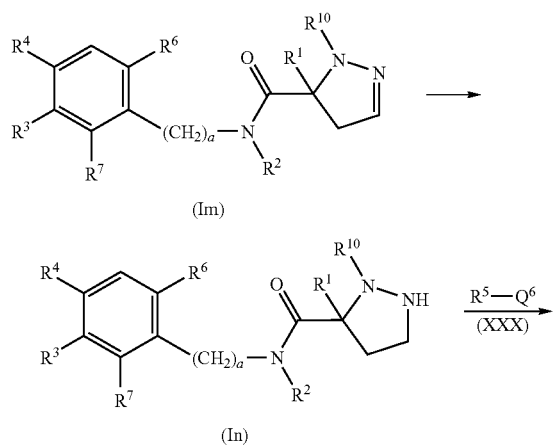

Accordingly, a suitably substituted compound of formula (Im), a compound of formula (Ic) wherein $R^5$ is hydrogen, is reacted with a reducing agent such as $NaBH_4$, $NaCNBH_3$, and the like, in an organic solvent such as AcOH, $CF_3CO_2H$, methanol, and the like, at a temperature in the range of from about 0° C. to about room temperature, to yield the corresponding compound of formula (In).

The compound of formula (In) is reacted with a suitably substituted compound of formula (XXX), wherein $Q^6$ is a suitable leaving group such as halogen, alkyl-carbonyl-oxy-, and the like, in the presence of an organic amine such as TEA, DIPEA, pyridine, and the like, in an organic solvent such as DCM, THF, DMF, and the like, at a temperature in the range of from about 0° C. to about room temperature, to yield the corresponding compound of formula (Ip).

Compounds of formula (I) wherein W is S, may be prepared according to the process outlined in Scheme 11.

Scheme 11

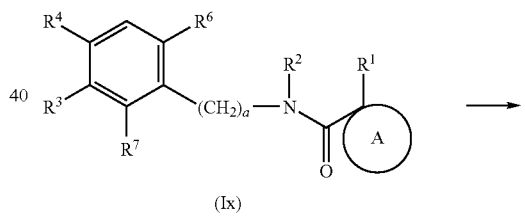

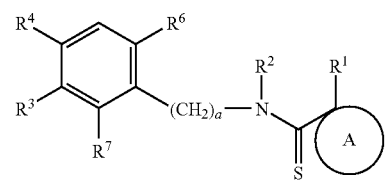

Accordingly, a suitably substituted compound of formula (Ix) is reacted with a source of sulfur such as Lawesson's reagent, $P_2S_5$, and the like, in an organic solvent such as toluene, xylene, p-oxlane, and the like, at a temperature in the range of from about 110° C. to about 150° C., to yield the corresponding compound of formula (Iy).

Compounds of formula (II) wherein Q is $-OR^E$ may be prepared according to the process outlined in Scheme 12.

Scheme 12

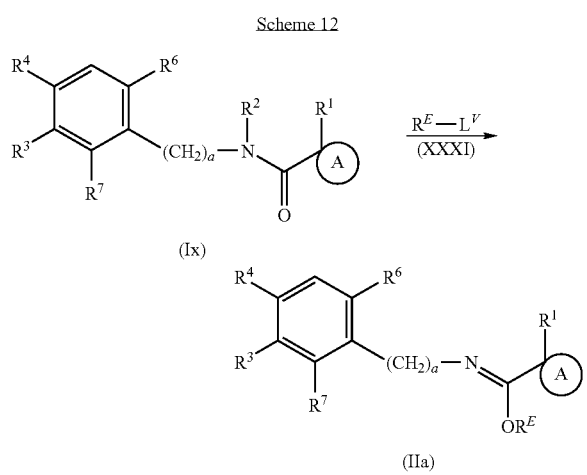

Accordingly, a suitably substituted compound of formula (Ix) wherein $R^2$ is hydrogen, is recated with a suitably substituted electrophile, a compound of formula (XXXI) wherein $L^V$ is a suitable leaving group such as Cl, Br, tosyl, triyl, mesyl, and the like, (for example where $R^E$ is ethyl, the compound of formula (XXIX) may be $BF_4$ etherate), in the presence of an organic amine base such as TEA, DIPEA, pyridine, and the like, in an organic solvent such as DCM, THF, diethyl ether, and the like, at a temperature in the range of from about −40° C. to about room temperature, to yield a mixture of the corresponding compound of formula (IIa) and (Iz).

Compounds of formula (II) wherein Q is —$SR^E$ or —$N(R^F)_2$ may be prepared according to the process outlined in Scheme 13.

Scheme 13

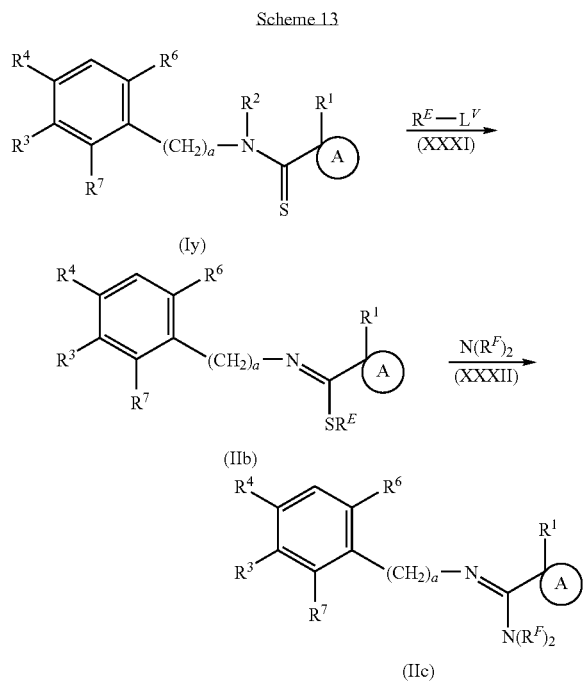

Accordingly, a suitably substituted compound of formula (Iy) is reacted with a suitably substituted compound of formula (XXXI), wherein $L^V$ is a suitable leaving group such as Cl, Br, tosyl, trifyl, mesyl, and the like, a known compound or compound prepared by known methods, in the presence of an organic amine base such as TEA, DIPEA, pyridine, and the like, in an organic solvent such as acetone, THF, DMF, and the like, at a temperature in the range of from about 0° C. to about 80° C., to yield the corresponding compound of formula (IIb).

The compound of formula (IIb) is reacted with a suitably substituted nitrogen containing nucleophile, a compound of formula (XXXII) (for example, $NH_3$, $NH(C_{1-4}alkyl)$, $N(C_{1-4}alkyl)_2$, $NH(OC_{1-4}alkyl)$, $NH_2(OH)$, $NH(CN)$, $NH(SO_2-C_{1-4}alkyl)$, pyrrolidine, and the like), in the presence of an inorganic base such as $K_2CO_3$, NaH, $Na_2CO_3$, and the like, in an organic solvent such as THF, DMF, dioxane, and the like, at a temperature in the range of from about room temperature to about 100° C., to yield the corresponding compound of formula (IIc).

One skilled in the art will recognize that when in the compound of formula (IIc) at least one $R^F$ group is hydrogen, then the corresponding compound of formula (I) wherein W is $NHR^F$ is its tautomer.

One skilled in the art will recognize that compound of formula (I) wherein

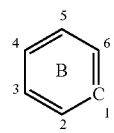

is other than phenyl, may be similarly prepared according to the processes outlined in Scheme 1-9 above, by selecting and substituting suitably substituted compounds for the starting materials and reagents.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The present invention further comprises pharmaceutical compositions containing one or more compounds of formula (I) and/or (II) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 50-100 mg and may be given at a dosage of from about 0.5-5.0 mg/kg/day, preferably from about 1.0-3.0 mg/kg/day. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating a disorder mediated by one or more androgen receptor(s) described in the present invention may also be carried out using a pharmaceutical composition comprising any of the compounds as defined herein and a pharmaceutically acceptable carrier. The pharmaceutical composition may contain between about 0.1 mg and 500 mg, preferably about 50 to 100 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxybutyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders mediated by one or more androgen receptor(s) is required.

The daily dosage of the products may be varied over a wide range from 0.01 to 1,000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day. Preferably, the range is from about 0.5 to about 5.0 mg/kg of body weight per day, most preferably, from about 1.0 to about 3.0 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following Examples are set forth to aid in the understanding of the invention, and are not intended and should not be construed to limit in any way the invention set forth in the claims which follow thereafter.

In the Examples which follow, some synthesis products may be listed as having been isolated as a residue. It will be understood by one of ordinary skill in the art that the term "residue" does not limit the physical state in which the product was isolated and may include, for example, a solid, an oil, a foam, a gum, a syrup, and the like.

One skilled in the art will recognize that in the Examples which follow and describe the preparation of compounds of formula (II) wherein Z is NHR$^F$ and their corresponding tautomers (compounds of formula (I) wherein W is NR$^F$), the identity and ratio of the two tautomeric forms in the isolated product was not determined.

Example 1

2-Methyl-N-(4-cyano-3-trifluoromethyl-phenyl)-acrylamide

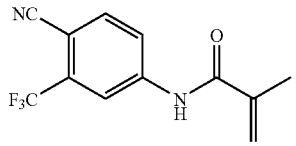

Methyl acrylic acid (510 mg, 6 mmol) in DMA (10 ml) was treated with thionyl chloride (714 mg, 6 mmol) at 0° C. The mixture was stirred for 30 min then 4-cyano-3-trifluoromethyl-aniline (1.0 g, 6.0 mmol) was added. The resulting suspension was stirred overnight and then quenched with NaHCO$_3$. The reaction mixture was extracted with ethyl acetate, washed with brine and dried with Na$_2$SO$_4$. The resulting concentrated crude product was purified on column (Ethyl acetate:Hexane, 1:2) to yield the title compound as a yellow solid.

$^1$H NMR (CDCl$_3$) δ 8.10 (s, 1H), 7.95 (dd, J=1.5 Hz, 0.5 Hz, 1H), 7.90 (br, 1H), 7.75 (d, J=1.5 Hz), 5.85 (s, 1H), 5.60 (s, 1H), 2.10 (s, 3H).

MS (m/z): M+Na (277).

Example 2

2-Methyl-N-(4-nitro-3-trifluoromethyl-phenyl)-acrylamide

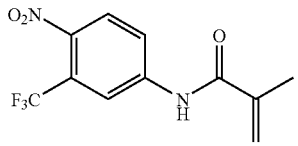

Following the procedure described in Example 1, starting from 4-nitro-3-trifluoromethyl-aniline (2.06 g, 10.0 mmol), the title compound was prepared as a yellow solid.

$^1$H NMR (CDCl$_3$) δ 8.00 (m, 3H), 7.95 (s, 1H), 5.88 (s, 1H), 5.60 (s, 1H), 2.10 (s, 3H).

MS (m/z): M+Na (297)

Example 3

2-Methyl-N-(4-Chloro-3-trifluoromethyl-phenyl)-acrylamide

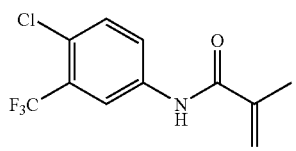

Following the procedure described in Example 1, starting from 4-chloro-3-trifluoromethyl-aniline, the title compound was prepared as a yellow solid.

$^1$H NMR (CDCl$_3$) δ 7.90 (s, 1H), 7.70 (dd, J=1.5 Hz, 0.5 Hz, 1H), 7.40 (d, J=1.5 Hz), 5.80 (s, 1H), 5.50 (s, 1H), 2.00 (s, 3H).

MS (m/z): MH+ (263)

Example 4

2-Methyl-N-(4-bromo-3-trifluoromethyl-phenyl)-acrylamide

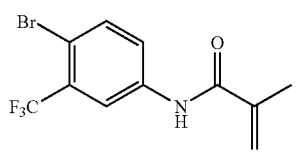

Following the procedure described in Example 1, starting from 4-bromo-3-trifluoromethyl-aniline, the title compound was prepared as a yellow solid.

$^1$H NMR (CDCl$_3$) δ 7.90 (s, 1H), 7.85 (s, br, 1H), 7.69 (d, J=7.5 Hz, 1H), 7.61 (d, J=7.5 Hz, 1H), 5.85 (s, 1H), 5.55 (s, 1H), 2.08 (s, 3H)

Example 5

2-Methyl-N-(3,4-di-chloro-phenyl)-acrylamide

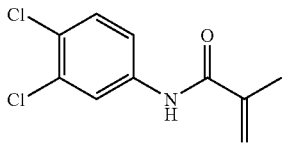

Following the procedure described in Example 1, starting from 3,4-di-chloro-aniline, the title compound was prepared as a yellow solid.

$^1$H NMR (CDCl$_3$) δ 7.85 (s, 1H), 7.50 (s, br, 1H), 7.36 (s, 2H), 5.78 (s, 1H), 5.51 (s, 1H), 2.08 (s, 3H).

MS (m/z): MH+ (230).

Example 6

2-Methyl-N-(3,4-di-cyano-phenyl)-acrylamide

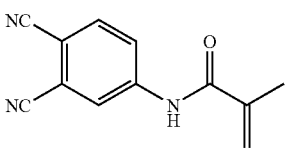

Following the procedure described in Example 1, starting from 3,4-di-cyano-aniline the title compound was prepared as a yellow solid.

$^1$H NMR (CDCl$_3$) δ 8.25 (s, 1H), 8.05 (s, br, 1H), 7.95 (d, J=7.5 Hz, 1H), 7.74 (d, J=7.5 Hz, 1H), 5.88 (s, 1H), 5.65 (s, 1H), 2.11 (s, 3H)

MS (m/z): MNa+ (234)

Example 7

N-(4-Benzoyl-phenyl)-2-methyl-acrylamide

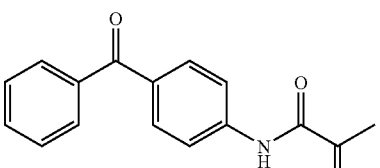

Following the procedure described in Example 1, starting from (4-amino-phenyl)-phenyl-methanone, the title compound was prepared as a yellow solid.

$^1$H NMR (CDCl$_3$) δ 7.98 (s, br, 1H), 7.88~7.72 (m, 6H), 7.60 (t, J=8.5 Hz, 1H), 7.52 (t, J=7.8 Hz, 2H), 5.88 (s, 1H), 5.55 (s, 1H)

MS (m/z): MH+ (266), MNa+ (288)

Example 8

N-(4-Benzoyl-benzyl)-2-methyl-acrylamide

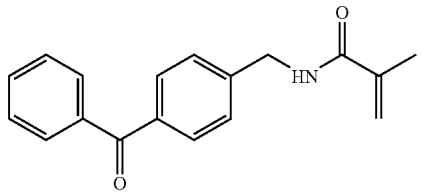

Following the procedure described in Example 1, starting from (4-Aminomethyl-phenyl)-phenyl-methanone, the title compound was prepared as a yellow solid.

$^1$H NMR (CDCl$_3$) δ 7.38~7.22 (m, 4H), 7.10 (t, J=7.5 Hz, 1H), 7.00 (m, 4H), 6.15 (s, br, 1H), 5.71 (s, 1H), 5.35 (s, 1H), 4.52 (d, J=4.5 Hz, 2H), 2.11 (s, 3H)

MS (m/z): MH+ (280), MNa+ (302)

Example 9

2-Methyl-N-(4-phenoxy-phenyl)-acrylamide

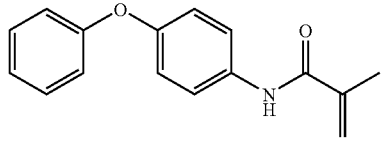

Following the procedure described in Example 1, starting from 4-phenoxy-phenylamine, the title compound was prepared as a yellow solid.

$^1$H NMR (CDCl$_3$) δ 7.70 (s, 1H), 7.50 (m, 2H), 7.30 (m, 2H), 7.00 (m, 5H), 5.80 (s, 1H), 4.90 (s, 1H), 2.00 (s, 3H). MS (m/z): M+1 (254).

MS (m/z): MH+ (254), MNa+ (276)

Example 10

2-Methyl-N-(4-cyano-phenyl)-acrylamide

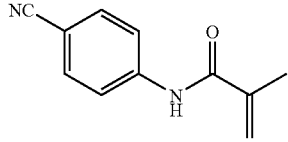

Following the procedure described in Example 1, starting from 4-cyano-aniline, the title compound was prepared as a yellow solid.

$^1$H NMR (CDCl$_3$) δ 7.70 (m, 5H), 5.80 (s, 1H), 5.05 (s, 1H), 2.00 (s, 3H)

MS (m/z): MH+ (187), MNa+ (209)

Example 11

2-Methyl-N-(4-phenylsulfanyl-phenyl)-acrylamide

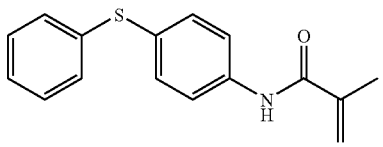

Following the procedure described in Example 1, starting from 4-phenylsulfanyl-phenylamine, the title compound was prepared as a yellow solid.

$^1$H NMR (CDCl$_3$) δ 7.60 (s, 1H), 7.55 (d, J=9.0 Hz, 2H), 7.35 (d, J=9.0 Hz, 2H), 7.20 (m, 5H), 5.80 (s, 1H), 5.00 (s, 1H), 2.00 (s, 3H)

MS (m/z): MH+ (270), MNa+ (292)

Example 12

N-(4-Benzyl-phenyl)-2-methyl-acrylamide

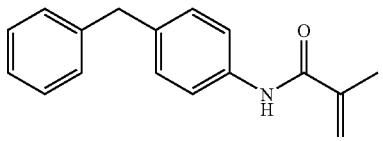

Following the procedure described in Example 1, starting from 4-benzyl-phenylamine, the title compound was prepared as a yellow solid.

$^1$H NMR (CDCl$_3$) δ 8.00 (d, J=9.0 Hz, 1H), 7.15-7.35 (m, 9H), 5.35 (s, 1H), 5.25 (s, 1H), 1.75 (s, 3H)

MS (m/z): MH+ (252), MNa+ (274)

Example 13

N-(4-Methanesulfonyl-benzyl)-2-methyl-acrylamide

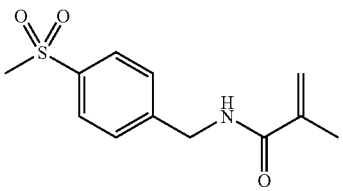

Following the procedure described in Example 1, starting from 4-methanesulfonyl-benzylamine, the title compound was prepared as a yellow solid.

$^1$H NMR (CDCl$_3$) δ 7.75 (d, J=8.5 Hz, 2H), 7.42 (d, J=8.5 Hz, 2H), 6.92 (s, 1H), 5.78 (s, 1H), 5.38 (s, 1H), 4.55 (d, J=6.5 Hz, 2H), 3.02 (s, 3H), 2.05 (s, 3H)

MS (m/z): MH+ (254), MNa+ (276)

Example 14

N-(4-Chloro-benzyl)-2-methyl-acrylamide

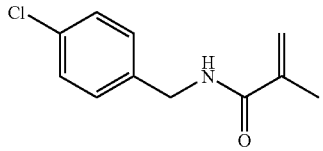

Following the procedure described in Example 1, starting from 4-chloro-benzylamine, the title compound was prepared as a yellow solid.

$^1$H NMR (CDCl$_3$) δ 7.20 (m, 4H), 6.15 (s, 1H), 5.75 (s, 1H), 4.85 (s, 1H), 4.50 (d, J=5.0 Hz, 2H), 2.00 (s, 3H).

MS (m/z): MH+ (210).

Example 15

N-(4-phenoxy-benzyl)-2-methyl-acrylamide

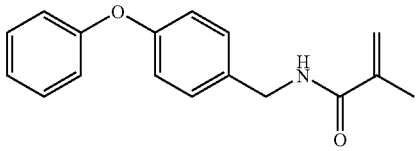

Following the procedure described in Example 1, starting from 4-phenoxy-benzylamine, the title compound was prepared as a yellow solid.

$^1$H NMR (CDCl$_3$) δ 7.18~6.94 (m, 4H), 6.85 (t, J=6.5 Hz, 1H), 6.77 (m, 4H), 5.56 (s, br, 1H), 5.65 (s, 1H), 5.30 (s, 1H), 4.38 (d, J=5.5 Hz, 2H), 2.06 (s, 3H)

MS (m/z): MH+ (268), MNa+ (290)

Example 16

N-(4-Cyano-3-trifluoromethyl-phenyl)-2-ethyl-acrylamide

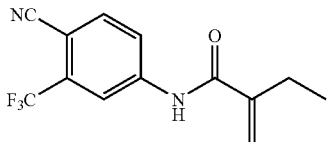

Following the procedure described in Example 1, starting from 4-cyano-3-trifluoromethyl-aniline and 2-ethyl-acrylic acid, the title compound was prepared as a yellow solid.

$^1$H NMR (CDCl$_3$) δ 8.70 (s, 1H), 8.18 (s, 1H), 8.06 (d, J=12.0H, 1H), 7.78 (d, J=12.0 Hz, 1H), 5.75 (s, 1H), 5.05 (s, 1H), 2.40 (q, J=9.0 Hz, 2H), 1.11 (t, J=9.0 Hz, 3H).

MS (m/z): MH+ (270), MNa+ (292)

Example 17

N-(4-Cyano-3-trifluoromethyl-phenyl)-2-propyl-acrylamide

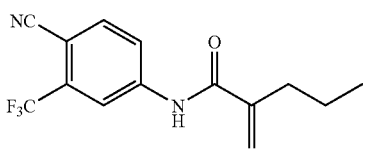

Following the procedure described in Example 1, starting from 4-cyano-3-trifluoromethyl-aniline and 2-propyl-acrylic acid, the title compound was prepared as a yellow solid.

MS (m/z): MH+ (284), MNa+ (306).

$^1$H NMR (CDCl$_3$) δ 8.20 (s, 1H), 8.12 (s, 1H), 8.00 (d, J=12.0 Hz, 1H), 7.78 (d, J=12.0 Hz, 1H), 5.70 (s, 1H), 5.00 (s, 1H), 2.40 (t, J=9.0 Hz, 2H), 1.50 (m, 2H), 0.95 (t, J=9.0 Hz, 3H).

Example 18

N-Benzyl-N″-(4-fluoro-benzylidene)-hydrazine

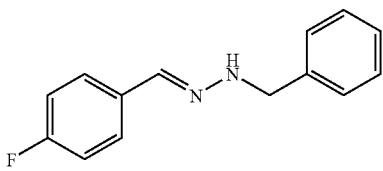

4-Fluorobenzenealdehyde (1.24 g, 10.0 mmol) in benzene (40 ml) was mixed with benzyl hydrazine hydrochloride (1.95 g, 10.0 mmol). The reaction was stirred at room temperature for 12 h. The solvent was then removed by vacuum evaporation to yield the title compound as a white solid.

$^1$H NMR (CDCl$_3$) δ 7.60 (m, 2H), 7.30 (m, 5H), 7.05 (m, 2H), 4.45 (s, 1H).

MS (m/z): MH+ (227)

Example 19

N-[4-(Methyl-hydrazonomethyl)-phenyl]-acetamide

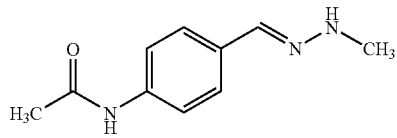

Following the procedure described in Example 18, starting from N-(4-formyl-phenyl)-acetamide and methyl hydrazine, the title compound was prepared as a white solid.

Example 20

4-Fluoro-benzaldehyde oxime

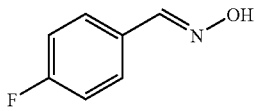

Following the procedure described in Example 18, starting from N-(4-formyl-phenyl)-acetamide and N-hydroxyamine, the title compound was prepared as a white solid.
MS (m/z): MH+ (140).

Example 21

4-Fluoro-N-(phenylmethyl)-benzenecarbohydrazonoyl chloride

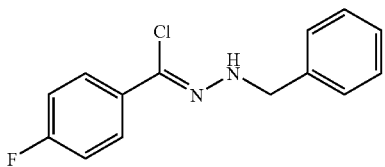

NCS (1.33 g, 10.0 mmol) was mixed with dimethyl sulfide (620 mg, 10.0 mmol) in $CH_2Cl_2$ (20 ml) at 0° C. for 30 min. The mixture was then cooled to −78° C. and N-benzyl-N''-(4-fluoro-benzylidene)-hydrazine, prepared as in Example 19, (2.62 g, 10.0 mmol) was added into the mixture. The mixture was maintained at −78° C. for 1 h, then slowly warmed up to room temperature over 2 hrs. The reaction mixture was quenched by $NaHCO_3$, then extracted with ethyl acetate. The organic layer was combined, washed with brine, dried over $Na_2SO_4$ and concentrated to yield a crude product. Purification of the crude product on column (100% $CH_2Cl_2$, Rf=0.5) yielded the title compound as a white solid.
$^1$H NMR (CDCl$_3$) δ 7.80 (m, 2H), 7.30 (m, 5H), 7.05 (m, 2H), 6.10 (br, 1H).
MS (m/z): MH+ (260).

Example 22

4-acetamido-N-(methyl)-benzenecarbohydrazonoyl chloride

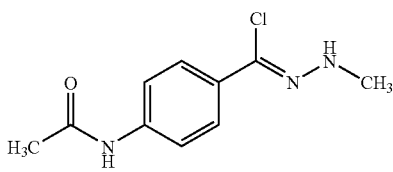

Following the procedure described in Example 21, starting from N-[4-(methyl-hydrazonomethyl)-phenyl]-acetamide, the title compound was prepared as a white solid.
MS (m/z): MH+ (226).

Example 23

2-Benzyl-5-(4-fluoro-phenyl)-3-methyl-3,4-dihydro-2H-pyrazole-3-carboxylic acid (4-cyano-3-trifluoromethyl-phenyl)-amide Compound #5

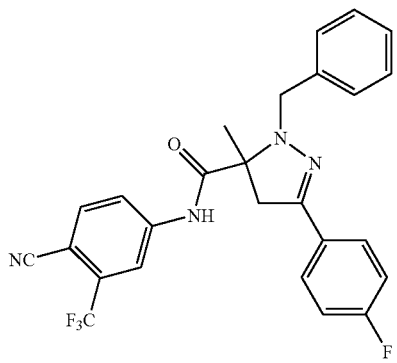

N-(4-Cyano-3-trifluoromethyl-phenyl)-2-methyl-acrylamide (500 mg, 2.0 mmol) was mixed with 4-fluoro-N-(phenylmethyl)-benzenecarbohydrazonoyl chloride (520 mg, 2.0 mmol) in $CH_2Cl_2$ at room temperature. Triethyl amine (300 mg, 3.0 mmol) was then added to the reaction mixture. The reaction was refluxed overnight, then quenched with $NaHCO_3$, and extracted with ethyl acetate. The organic layer was combined, washed with brine, dried over $Na_2SO_4$ and concentrated to yield a crude product. Purification of the crude product on column (Hexane:ethyl acetate, 5:1, Rf=0.5) yielded the title compound as a white solid.
$^1$H NMR (CDCl$_3$) δ 9.25 (s, 1H), 7.80 (s, 1H), 7.70 (s, 2H), 7.60 (m, 2H), 7.45 (m, 2H), 7.05 (m, 5H), 4.30 (dd, J=11.1 Hz, 1.0 Hz, 2H), 3.30 (dd, J=3.6 Hz, 1.2 Hz, 2H), 1.65 (s, 3H).
MS (m/z): MH+ (481)

Example 24

5-(4-Fluoro-phenyl)-3-methyl-3,4-dihydro-2H-pyrazole-3-carboxylic acid (4-cyano-3-trifluoromethyl-phenyl)-amide Compound #1

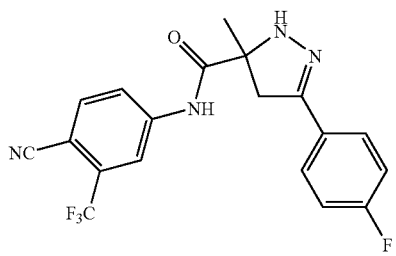

2-Benzyl-5-(4-fluoro-phenyl)-3-methyl-3,4-dihydro-2H-pyrazole-3-carboxylic acid (4-cyano-3-trifluoromethyl-phenyl)-amide (150 mg, 0.33 mmol) in ethanol, was treated with Pd/C (100 mg, 10%) under $H_2$ balloon for two days. Pd/C was removed by vacuum filtration and the solvent was removed by vacuum rotary evaporation to yield a crude product. Purification of the crude product by silica gel (Hex:ethyl acetate, 2:1, Rf=0.4) yielded the title compound as a white solid.

$^1$H NMR (CDCl$_3$) δ 9.75 (s, 1H), 8.10 (s, 1H), 7.85 (dd, J=4.5 Hz, 0.2 Hz, 2H), 7.65 (m, 2H), 7.05 (m, 2H), 5.70 (br, 1H), 3.30 (dd, J=3.6 Hz, 1.2 Hz, 2H), 1.65 (s, 3H)

MS (m/z): MH+ (390)

Example 25

5-(4-Acetylamino-phenyl)-2,3-dimethyl-3,4-dihydro-2H-pyrazole-3-carboxylic acid (4-cyano-3-trifluoromethyl-phenyl)-amide Compound #39

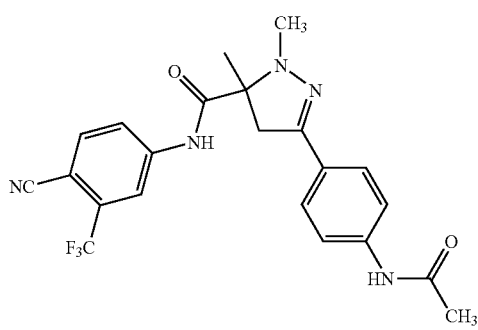

Following the procedure described in Example 23, starting from 2-methyl-N-(4-cyano-3-trifluoromethyl-phenyl)-acrylamide and 4-acetamido-N-(methyl)-benzenecarbohydrazonoyl chloride, the title compound was prepared as a white solid.

$^1$H NMR (CDCl$_3$) δ 9.62 (s, 1H), 8.18 (s, 1H), 8.02 (d, J=7.5 Hz, 1H), 7.98 (d, J=7.5 Hz, 1H), 7.80 (s, 1H), 7.50 (m, 4H), 3.38 (abq, J=12.5 Hz, 2H), 2.98 (s, 3H), 2.20 (s, 3H), 1.50 (s, 3H).

MS (m/z): MH+ (444), MH− (442)

Example 26

5-(4-Acetylamino-phenyl)-2,3-dimethyl-3,4-dihydro-2H-pyrazole-3-carboxylic acid (4-nitro-3-trifluoromethyl-phenyl)-amide Compound #40

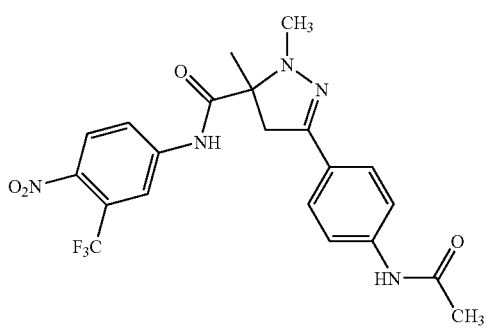

Following the procedure described in Example 23, starting from 2-methyl-N-(4-nitro-3-trifluoromethyl-phenyl)-acrylamide and 4-acetamido-N-(methyl)-benzenecarbohydrazonoyl chloride, the title compound was prepared as a white solid.

$^1$H NMR (CDCl$_3$) δ 9.52 (s, 1H), 8.15 (s, 1H), 8.06 (d, J=7.5 Hz, 1H), 7.95 (d, J=7.5 Hz, 1H), 7.61 (s, 1H), 7.55 (m, 4H), 3.38 (abq, J=12.5 Hz, 2H), 2.98 (s, 3H), 2.18 (s, 3H), 1.48 (s, 3H)

MS (m/z): MH+ (464), MNa+ (486)

Example 27

3-(4-Fluoro-phenyl)-5-methyl-4,5-dihydro-isoxazole-5-carboxylic acid (4-cyano-3-trifluoromethyl-phenyl)-amide Compound #95

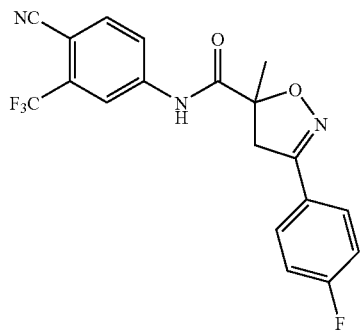

4-Fluorobenzamidoxime (1.39 g, 10 mmol) was mixed with triethylamine (200 mg, 2.0 mmol) and NaOCl (4%, 15 ml, 1.48 g, 10 mmol) in CH$_2$Cl$_2$ (25 ml). N-(4-(Cyano-3-trifluoromethyl-phenyl)-2-methyl-acrylamide (508 mg, 2.0 mmol) was added into the mixture and the mixture was then stirred for 3 hrs at room temperature. The reaction mixture was quenched by NaHCO$_3$, and then extracted with ethyl acetate. The organic layer was combined, washed with brine, dried over Na$_2$SO$_4$ and concentrated to yield a crude product. Purification of the crude product on column (Hexane:ethyl acetate, 2:1, Rf=0.45) yielded the title compound as a white solid.

$^1$H NMR (CDCl$_3$) δ 9.15 (s, 1H), 8.15 (s, 1H), 7.85 (dd, J=4.5 Hz, 0.2 Hz, 2H), 7.60 (m, 2H), 7.05 (m, 2H), 3.75 (dd, J=17.4 Hz, 2.0 Hz, 2H), 1.75 (s, 3H).

MS (m/z): MH+ (392)

Example 28

1-R-p-Toluenesulfonylhydrazone (General procedure)

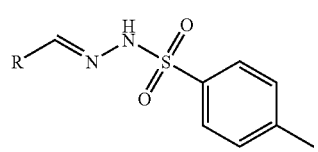

p-Toluenesulfonylhydrazine (10.0 mmol) was mixed with a suitably selected compound of the formula R—CHO (10.0 mmoL) in methanol (40 ml) at room temperature for 4 h. The mixture was then concentrated to yield the title compound as a white solid (unless otherwise noted).

Example 29

5-(4-Fluoro-phenyl)-3-methyl-3,4-dihydro-2H-pyrazole-3-carboxylic acid (4-cyano-3-trifluoromethyl-phenyl)-amide and 5-(4-Fluoro-phenyl)-3-methyl-4,5-dihydro-3H-pyrazole-3-carboxylic acid (4-cyano-3-trifluoromethyl-phenyl)-amide Compound #1 and Compound #64

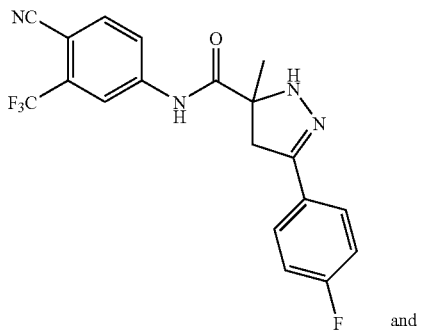

and

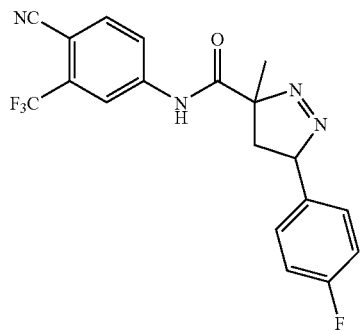

2-[(1E)-(4-fluorophenyl)methylidene]toluenesulfonylhydrazone, prepared according to the procedure described in Example 29 (600 mg, 2.1 mmol) in THF (20 ml) was treated by NaH (60%, 120 mg, 3 mmol) at 0° C. for 20 min, followed by the addition of N-(4-cyano-3-trifluoromethyl-phenyl)-2-methyl-acrylamide (500 mg, 2.0 mmol). The reaction mixture was then heated to 55° C. overnight, then quenched by NaHCO$_3$, and extracted by ethyl acetate. The organic layer was combined, washed with brine, dried over Na$_2$SO$_4$ and concentrated to yield crude product as a mixture. Purification of the crude product on a column yielded the title compound as separate products, as a white solids.

5-(4-Fluoro-phenyl)-3-methyl-3,4-dihydro-2H-pyrazole-3-carboxylic acid (4-cyano-3-trifluoromethyl-phenyl)-amide (Hexane:ethyl acetate, 2:1, Rf=0.45, 475 mg, 61%)

5-(4-Fluoro-phenyl)-3-methyl-4,5-dihydro-3H-pyrazole-3-carboxylic acid (4-cyano-3-trifluoromethyl-phenyl)-amide (Hexane:ethyl acetate: 2:1, Rf=0.6, 100 mg, 13%):
MS (m/z): MH+ (391)
$^1$H NMR (CDCl$_3$) δ 8.50 (s, 1H), 8.10 (s, 1H), 7.90 (dd, J=1.5 Hz, 0.2 Hz, 1H), 7.75 (d, J=1.5 Hz, 1H), 7.20 (m, 2H), 7.10 (m, 2H), 5.60 (t, J=0.9 Hz, 1H), 3.00 (dd, J=1.0 Hz, 0.8 Hz, 1H), 1.87 (s, 3H), 1.55 (t, J=1.1 Hz, 0.6 Hz, 1H).

Example 30

5-(4-Fluoro-phenyl)-3-methyl-3,4-dihydro-2H-pyrazole-3-carboxylic acid (4-nitro-3-trifluoromethyl-phenyl)-amide Compound #7

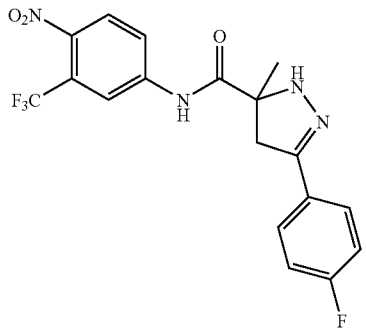

Following the procedure described in Example 29, starting from 2-methyl-N-(4-nitro-3-trifluoromethyl-phenyl)-acrylamide and 2-[(1E)-(4-fluorophenyl)methylidene]toluenesulfonylhydrazone, the title compound was prepared as a yellow solid.
$^1$H NMR (MeOH) δ 6.45 (d, J=0.9 Hz, 1H), 6.20 (m, 1H), 6.00 (s, 1H), 5.55 (m, 4H), 2.00 (dd, J=5.5 Hz, 1.8 Hz, 2H), 1.70 (s, 3H).
MS (m/z): MNa+ (410)

Example 31

3-Methyl-5-trimethylsilanyl-4,5-dihydro-3H-pyrazole-3-carboxylic acid (4-cyano-3-trifluoromethyl-phenyl)-amide and 3-Methyl-3,4-dihydro-2H-pyrazole-3-carboxylic acid (4-cyano-3-trifluoromethyl-phenyl)-amide Compound #51 and Compound #47

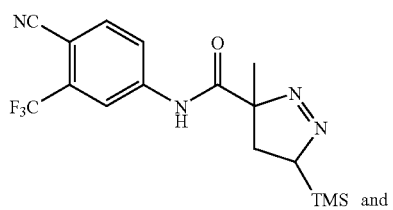

and

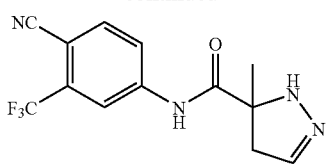
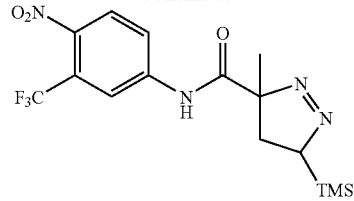

N-(4-Cyano-3-trifluoromethyl-phenyl)-2-methyl-acrylamide (180 mg, 0.71 mmoL) in THF (5 mL) was treated with TMSCHN$_2$ (2.0 M in hexanes, 3.54 mmoL, 1.8 mL) at −10° C. The reaction mixture was then warmed to room temperature slowly and stirred overnight. The solvent was removed and the residue was purified by column chromatography (silica gel, 1:1 hexanes:EtOAc) to yield the title compound as a white solids (1:1 diastereomers).

3-Methyl-5-trimethylsilanyl-4,5-dihydro-3H-pyrazole-3-carboxylic acid (4-cyano-3-trifluoromethyl-phenyl)-amide $^1$H NMR (CDCl$_3$) δ 8.58 (br, s, 1H) for diastereomer 1, 8.35 (br, s, 1H) for diastereomer 2, 7.90 (m, 1), 7.70 (m, 1H), 7.58 (m, 1H), 4.35 (dd, J=10.5, 5.0 Hz, 1H) for diastereomer 1, 4.30 (dd, J=11.0, 6.0 Hz, 1H) for diastereomer 2, 2.30 (m, 1H) for diastereomer 1, 2.05 (m, 1H) for diastereomer 2, 1.66 (m, 1H) for diastereomer 1, 1.48 (s, 3H) for diastereomer 1, 1.42 (s, 3H) for diastereomer 2, 1.29 (m, 1H) for diastereomer 2), 0.10 (s, 9H) for diastereomer 1), 0.01 (s, 9H) for diastereomer 2 MS (m/z), 298 [M-TMS+H]$^+$, 319 [M-TMS+Na]$^+$ 3-Methyl-3,4-dihydro-2H-pyrazole-3-carboxylic acid (4-cyano-3-trifluoromethyl-phenyl)-amide $^1$H NMR (CDCl$_3$) 9.62 (s, 1H), 8.10 (s, 1H), 7.95 (d, J=6.5 Hz, 1H), 7.77 (d, J=6.5 Hz, 1H), 6.88 (s, 1H), 5.52 (s, 1H), 3.05 (abq, J=12.5 Hz, 2H), 1.56 (s, 3H)

MS (m/z), MH+ (297).

Example 32

3-Methyl-3,4-dihydro-2H-pyrazole-3-carboxylic acid (4-nitro-3-trifluoromethyl-phenyl)-amide and 3-Methyl-5-trimethylsilanyl-4,5-dihydro-3H-pyrazole-3-carboxylic acid (4-nitro-3-trifluoromethyl-phenyl)-amide Compound #6 and Compound #57

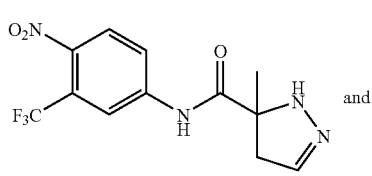

Following the procedure described in Example 31, starting from 2-methyl-N-(4-nitro-3-trifluoromethyl-phenyl)-acrylamide and TMSCHN$_2$ the title compounds were prepared, both as a white solids.

3-Methyl-3,4-dihydro-2H-pyrazole-3-carboxylic acid (4-nitro-3-trifluoromethyl-phenyl)-amide $^1$H NMR (CDCl$_3$) δ 9.62 (br, s, 1H), 8.10 (s, 1H), 7.98 (m, 2H), 6.88 (s, 1H), 5.50 (s, 1H), 3.10 (Abq, J=12.5 Hz, 2H), 1.52 (s, 3H)

MS (m/z), MH$^+$, 317, MH$^−$, 315

3-Methyl-5-trimethylsilanyl-4,5-dihydro-3H-pyrazole-3-carboxylic acid (4-nitro-3-trifluoromethyl-phenyl)-amide $^1$H NMR (CDCl$_3$) δ 8.78 (br, s, 1H), 8.05 (s, 1H), 7.88 (d, J=7.0 Hz, 1H), 7.74 (d, J=7.0 Hz, 1H), 4.48 (dd, J=11.0, 4.5 Hz, 1H), 2.10 (dd, J=13.0, 11.0 Hz, 1H), 1.78 (dd, J=13.0, 4.5 Hz, 1H), 1.55 (s, 3H)

Example 33

N-[4-cyano-3-(trifluoromethyl)phenyl]-3-[2-[[(1,1-dimethylethyl)dimethylsilyl]oxy]phenyl]-4,5-dihydro-5-methyl-1H-pyrazole-5-carboxamide Compound #54

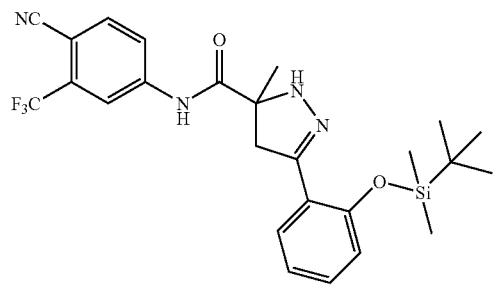

Following the procedure described in Example 29, 4-methyl-2-[(1Z)-[2-[[(1,1-dimethylethyl)dimethylsilyl]oxy]phenyl]methylidene]benzenesulfonyl hydrazone was reacted to yield the title compound as a white solid.

$^1$H NMR (CDCl$_3$) δ 9.25 (s, 1H), 8.16 (s, 1H), 7.95 (d, J=0.6 Hz, 1H), 7.65 (d, J=0.6 Hz, 1H), 7.10 (m, 1H), 6.80 (m, 3H), 5.80 (m, 1H), 2.30 (m, 1H), 1.80 (m, 1H), 1.51 (s, 3H), 0.89 (s, 9H), 0.21 (s, 6H)

MS (m/z): M+(503)

Example 34

N-[4-cyano-3-(trifluoromethyl)phenyl]-4,5-dihydro-3-(2-hydroxyphenyl)-5-methyl-1H-pyrazole-5-carboxamide and 5-(2-hydroxy-phenyl)-3-methyl-4,5-dihydro-3H-pyrazole-3-carboxylic acid (4-cyano-3-trifluoromethyl-phenyl)-amide Compound #76 and Compound #55

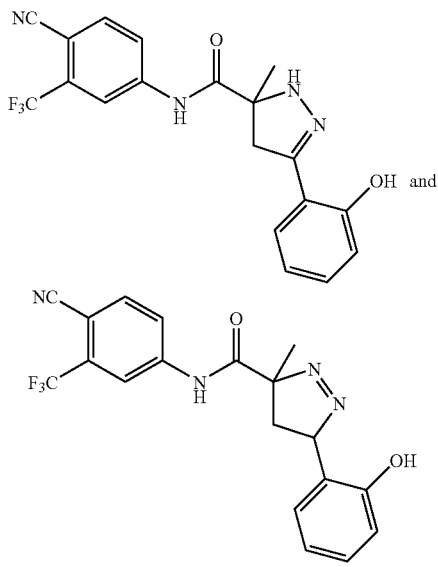

N-[4-cyano-3-(trifluoromethyl)phenyl]-3-[2-[[(1,1-dimethylethyl)dimethylsilyl]oxy]phenyl]-4,5-dihydro-5-methyl-1H-pyrazole-5-carboxamide, prepared as in Example 34 (80 mg, 1.6 mmol) in THF (20 ml) was treated with TBAF (1M, 3.2 ml, 3.2 mmol) at 0° C. The reaction mixture was stirred at room temperature for 2 h, then quenched with $H_2O$, extracted with ethyl acetate, dried over $Na_2SO_4$ and concentrated to yield a crude product. The crude product was purified by silica gel (Hexane:ethyl acetate, 2:1, Rf=0.35) to yield the title compound as a white solid.

N-[4-cyano-3-(trifluoromethyl)phenyl]-4,5-dihydro-3-(2-hydroxyphenyl)-5-methyl-1H-pyrazole-5-carboxamide $^1$H NMR (CDCl$_3$) δ10.78 (br, 1H), 9.75 (s, 1H), 8.16 (s, 1H), 7.95 (d, J=0.6 Hz, 1H), 7.70 (d, J=0.6 Hz, 1H), 7.25 (m, 1H), 7.08 (d, J=0.6 Hz, 1H), 6.85 (m, 1H), 5.95 (s, 1H), 3.40 (dd, J=5.1 Hz, 2.1 Hz, 1H), 1.65 (s, 3H)
MS (m/z): MNa+ (401)

5-(2-hydroxy-phenyl)-3-methyl-4,5-dihydro-3H-pyrazole-3-carboxylic acid (4-cyano-3-trifluoromethyl-phenyl)-amide $^1$H NMR (CDCl$_3$) δ 9.80 (s, 1H), 8.25 (s, 1H), 7.90 (d, J=7.6 Hz, 1H), 7.70 (d, J=7.6 Hz, 1H), 7.65 (s, 1H), 7.55 (d, J=6.6 Hz, 2H), 6.92 (d, J=6.6 Hz, 2H), 5.70 (br, 1H), 3.15 (abq, J=12.5 Hz, 1H), 1.55 (s, 3H)
MS (m/z): MNa+ (401)

Example 35

N-[4-cyano-3-(trifluoromethyl)phenyl]-3-[2-[[(1,1-dimethylethyl)dimethylsilyl]oxy]-3-fluorophenyl]-4,5-dihydro-5-methyl-1H-pyrazole-5-carboxamide Compound #96

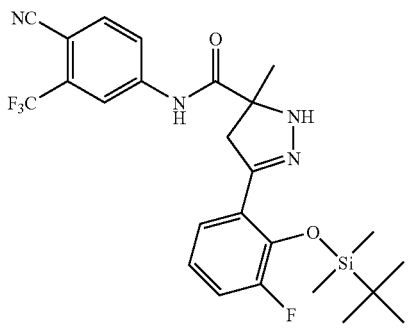

Following the procedure described in Example 29, 4-methyl-2-[(1Z)-2-[[(1,1-dimethylethyl)dimethylsilyl]oxy]-3-fluorophenyl]methylidene]benzenesulfonyl hydrazone was reacted to yield the title compound as a white solid.

$^1$H NMR (CDCl$_3$) δ 9.60 (s, 1H), 8.00 (s, 1H), 7.78 (d, J=0.6 Hz, 1H), 7.65 (d, J=0.6 Hz, 1H), 7.10 (m, 1H), 6.95 (m, 1H), 6.75 (m, 1H), 5.50 (br, 1H), 3.25 (dd, J=5.1 Hz 1.2 Hz, 2H), 1.55 (s, 3H), 0.78 (s, 9H), 0.21 (d, J=4.8 Hz, 6H)

MS (m/z): M Na+ (544), M− (520)

Example 36

N-[4-cyano-3-(trifluoromethyl)phenyl]-3-(3-fluoro-2-hydroxyphenyl)-4,5-dihydro-5-methyl-1H-pyrazole-5-carboxamide Compound #97

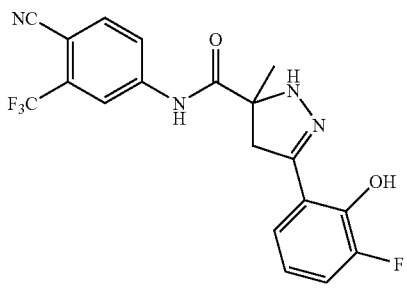

Following the procedure described in Example 34, N-[4-cyano-3-(trifluoromethyl)phenyl]-3-[2-[[(1,1-dimethylethyl)dimethylsilyl]oxy]-3-fluorophenyl]-4,5-dihydro-5-methyl-1H-pyrazole-5-carboxamide, prepared as in Example 36, was reacted to yield the title compound as a white solid.

MS (m/z): M+ (407)

¹H NMR (CDCl₃) δ 10.84 (s, 1H), 9.63 (s, 1H), 8.14 (s, 1H), 7.97 (d, J=0.6 Hz, 1H), 7.79 (d, J=0.6 Hz, 1H), 7.11 (m, 1H), 6.92 (m, 1H), 6.82 (m, 1H), 5.87 (s, 1H), 3.45 (dd, J=3.6 Hz, 1.2 Hz, 2H), 1.69 (s, 3H)

Example 37

3-Methyl-5-thiophen-2-yl-3,4-dihydro-2H-pyrazole-3-carboxylic acid (4-cyano-3-trifluoromethyl-phenyl)-amide Compound #49

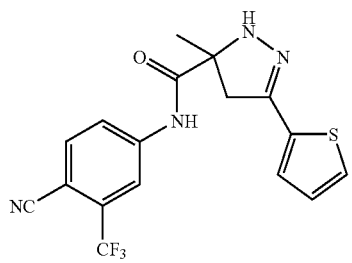

Following the procedure described in Example 29, 4-methyl-2-[(1E)-2-thienylmethylidene]benzenesulfonyl hydrazone was reacted to yield the title compound as a white solid.

¹H NMR (CDCl₃) δ 9.75 (s, 1H), 8.13 (s, 1H), 7.92 (dd, J=1.1 Hz, 0.2 Hz, 1H), 7.78 (d, J=0.8 Hz, 1H), 7.37 (m, 1H), 7.11 (m, 1H), 7.04 (m, 1H), 5.55 (br, 1H), 3.35 (dd, J=5.4 Hz, 1.7 Hz, 2H), 1.65 (s, 3H)

MS (m/z): MH+ (379)

Example 38

5-Furan-2-yl-3-methyl-4,5-dihydro-3H-pyrazole-3-carboxylic acid (4-cyano-3-trifluoromethyl-phenyl)-amide Compound #4

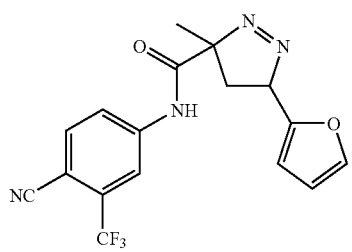

Following the procedure described in Example 29, 4-methyl-2-[(1E)-2-furanylmethylidene]benzenesulfonyl hydrazone was reacted to yield the title compound as a white solid.

¹H NMR (CDCl₃) δ 9.75 (s, 1H), 8.13 (s, 1H), 7.92 (dd, J=1.1 Hz, 0.2 Hz, 1H), 7.78 (d, J=0.8 Hz, 1H), 6.65-6.50 (m, 3H), 3.31 (dd, J=5.4 Hz, 1.7 Hz, 2H), 1.65 (s, 3H)

MS (m/z): MH+ (363)

Example 39

3-Methyl-5-(tetrahydro-furan-2-yl)-4,5-dihydro-3H-pyrazole-3-carboxylic acid (4-cyano-3-trifluoromethyl-phenyl)-amide Compound #52

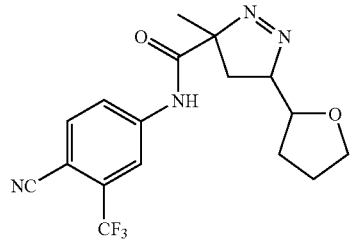

Following the procedure described in Example 29, 4-methyl-2-[(1E)-(tetrahydro-2-furanyl)methylidene]benzenesulfonyl hydrazone was reacted to yield the title compound as a white solid.

¹H NMR (CDCl₃) δ 9.09 (s, 1H), 8.16 (m, 1H), 7.95 (m, 1H), 7.81 (d, J=0.6 Hz, 1H), 4.49 (dd, J=1.0 Hz, 0.5 Hz, 1H), 4.00-3.60 (m, 3H), 2.50-1.60 (m, 6H), 1.56 (s, 3H)

MS (m/z): MH+ (366)

Example 40

3-Methyl-5-trifluoromethyl-3,4-dihydro-2H-pyrazole-3-carboxylic acid (4-cyano-3-trifluoromethyl-phenyl)-amide Compound #8

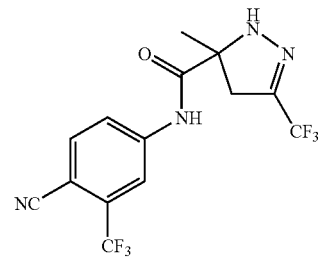

Following the procedure described in Example 29, 4-methyl-2-[(1E)-2,2,2-trifluoroethylidene]benzenesulfonyl hydrazone was reacted to yield the title compound as a white solid.

¹H NMR (CDCl₃) δ 9.30 (s, 1H), 8.11 (s, 1H), 7.98 (dd, J=1.1 Hz, 0.2 Hz, 1H), 7.80 (d, J=0.8 Hz, 1H), 6.18 (br, 1H), 3.15 (dd, J=6.0 Hz, 1.8 Hz, 2H), 1.62 (s, 3H)

MS (m/z): MNa+ (387)

Example 41

5-Cyclohexyl-3-methyl-3,4-dihydro-2H-pyrazole-3-carboxylic acid (4-cyano-3-trifluoromethyl-phenyl)-amide and 5-Cyclohexyl-3-methyl-4,5-dihydro-3H-pyrazole-3-carboxylic acid (4-cyano-3-trifluoromethyl-phenyl)-amide Compound #25 and Compound #68

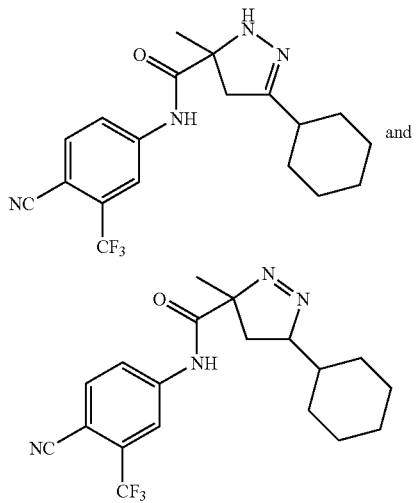

Following the procedure described in Example 29, 4-methyl-2-[(1E)-cyclohexylmethylidene]benzenesulfonyl hydrazone was reacted to yield the two title compounds as a white solids.

5-Cyclohexyl-3-methyl-3,4-dihydro-2H-pyrazole-3-carboxylic acid (4-cyano-3-trifluoromethyl-phenyl)-amide (Hexane:Ethyl Acetate, 2:1, Rf=0.2, 210 Mg, 19%)

$^1$H NMR (CDCl$_3$) δ 9.82 (s, 1H), 8.10 (s, 1H), 7.95 (dd, J=1.0 Hz, 0.2 Hz, 1H), 7.78 (d, J=0.8 Hz, 1H), 2.98 (dd, J=5.1 Hz, 1.7 Hz, 2H), 1.77 (m, 6H), 1.50 (s, 3H), 1.27 (m, 4H).

MS (m/z): MH+ (379)

5-Cyclohexyl-3-methyl-4,5-dihydro-3H-pyrazole-3-carboxylic acid (4-cyano-3-trifluoromethyl-phenyl)-amide (Hexane:Ethyl Acetate, 2:1, Rf=0.8, 160 Mg, 16%)

$^1$H NMR (CDCl$_3$) δ 9.20 (s, 1H), 8.20 (s, 1H), 8.05 (dd, J=1.0 Hz, 0.2 Hz, 1H), 7.85 (d, J=0.9 Hz, 1H), 4.36 (dd, J=1.5 Hz, 0.8 Hz, 1H), 2.15 (d, J=1.0 Hz, 1H), 1.70 (m, 6H), 1.55 (s, 3H), 1.20 (m, 5H)

MS (m/z): MNa+ (401)

Example 42

5-(4-Ethyl-phenyl)-3-methyl-3,4-dihydro-2H-pyrazole-3-carboxylic acid (4-cyano-3-trifluoromethyl-phenyl)-amide Compound #3

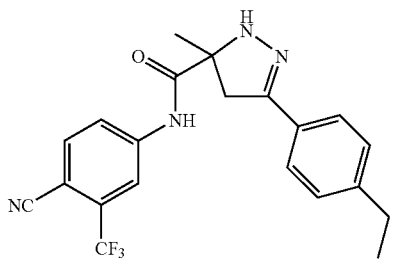

Following the procedure described in Example 29, 4-methyl-2-[(1E)-(4-ethylphenyl)methylidene]benzenesulfonyl hydrazone was reacted to yield the title compound as a white solid.

$^1$H NMR (CDCl$_3$) δ 9.80 (s, 1H), 8.16 (m, 1H), 7.90 (d, J=0.6 Hz, 1H), 7.78 (d, J=0.6 Hz, 1H), 7.50 (d, J=0.8 Hz, 2H), 7.15 (d, J=0.8 Hz, 2H), 5.83 (br, 1H), 3.32 (dd, J=3.9 Hz, 1.3 Hz, 1H), 2.65 (q, J=0.6 Hz, 2H), 1.62 (s, 3H), 1.20 (t, J=0.4 Hz, 3H)

MS (m/z): MH+ (401)

Example 43

5-(4-Fluoro-3-methyl-phenyl)-3-methyl-3,4-dihydro-2H-pyrazole-3-carboxylic acid (4-cyano-3-trifluoromethyl-phenyl)-amide Compound #56

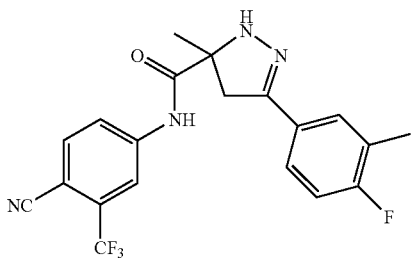

Following the procedure described in Example 29, 4-methyl-2-[(1E)-(4-fluoro-3-methylphenyl)methylidene]benzenesulfonyl hydrazone was reacted to yield the title compound as a white solid.

$^1$H NMR (CDCl$_3$) δ 9.75 (s, 1H), 8.16 (s, 1H), 7.95 (d, J=0.6 Hz, 1H), 7.78 (d, J=0.6 Hz, 1H), 7.50-7.40 (m, 2H), 7.05 (m, 2H), 4.60 (br, 1H), 3.30 (dd, J=3.9 Hz, 1.3 Hz, 1H), 2.30 (s, 3H), 1.65 (s, 3H)

MS (m/z): MNa+ (427)

Example 44

5-Isopropyl-3-methyl-3,4-dihydro-2H-pyrazole-3-carboxylic acid (4-cyano-3-trifluoromethyl-phenyl)-amide and 5-Isopropyl-3-methyl-4,5-dihydro-3H-pyrazole-3-carboxylic acid (4-cyano-3-trifluoromethyl-phenyl)-amide Compound #42 and Compound #69

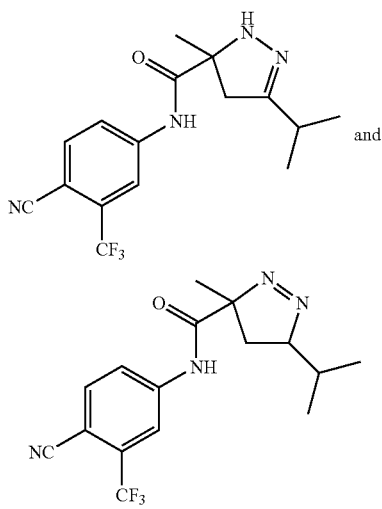

and

Following the procedure described in Example 29, 4-methyl-2-[(1E)-2-methylpropylidene]benzenesulfonyl hydrazone was reacted to yield the two title compounds as a white solids.

5-Isopropyl-3-methyl-3,4-dihydro-2H-pyrazole-3-carboxylic acid (4-cyano-3-trifluoromethyl-phenyl)-amide (Hexane:Ethyl Acetate, 2:1, Rf=0.2, 350 Mg, 35%)

$^1$H NMR (CDCl$_3$) δ 9.85 (s, 1H), 8.10 (s, 1H), 7.95 (dd, J=1.0 Hz, 0.2 Hz, 1H), 7.78 (d, J=0.8 Hz, 1H), 5.35 (br, 1H), 2.98 (dd, J=5.4 Hz, 1.8 Hz, 2H), 1.55 (s, 3H), 1.16 (s, 3H), 1.17 (s, 3H)

MS (m/z): MH+ (339)

5-Isopropyl-3-methyl-4,5-dihydro-3H-pyrazole-3-carboxylic acid (4-cyano-3-trifluoromethyl-phenyl)-amide (Hexane:Ethyl Acetate, 2:1, Rf=0.8, 560 Mg, 55%)

$^1$H NMR (CDCl$_3$) δ 9.18 (s, 1H), 8.20 (s, 1H), 8.05 (dd, J=1.0 Hz, 0.2 Hz, 1H), 7.85 (d, J=0.9 Hz, 1H), 4.36 (dd, J=1.2 Hz, 0.6 Hz, 1H), 2.16 (q, J=0.7 Hz, 1H), 1.80 (m, 2H), 1.55 (s, 3H), 1.22 (d, J=0.7 Hz, 3H), 1.00 (d, J=0.7 Hz, 3H)

MS (m/z): M+ (338)

Example 45

5-(4-Methoxy-phenyl)-3-methyl-4,5-dihydro-3H-pyrazole-3-carboxylic acid (4-cyano-3-trifluoromethyl-phenyl)-amide Compound #10

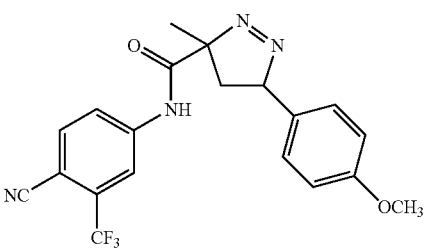

Following the procedure described in Example 29, 4-methyl-2-[(1E)-(4-methoxyphenyl)methylidene]benzenesulfonyl hydrazone was reacted to yield the title compound as a white solid.

$^1$H NMR (CDCl$_3$) δ 9.85 (s, 1H), 8.16 (s, 1H), 7.95 (d, J=0.6 Hz, 1H), 7.76 (d, J=0.6 Hz, 1H), 7.58 (d, J=0.6 Hz, 2H), 6.90 (d, J=0.6 Hz, 2H), 5.68 (br, 1H), 3.82 (s, 3H), 3.30 (dd, J=3.9 Hz, 1.3 Hz, 1H), 1.65 (s, 3H)

MS (m/z): M+ (403)

Example 46

3-Methyl-5-pentafluorophenyl-3,4-dihydro-2H-pyrazole-3-carboxylic acid (4-cyano-3-trifluoromethyl-phenyl)-amide Compound #9

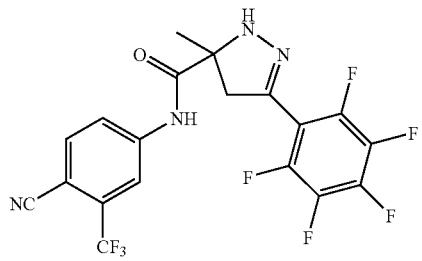

Following the procedure described in Example 29, 4-methyl-2-[(1E)-(pentafluorophenyl)methylidene]benzenesulfonyl hydrazone was reacted to yield the title compound as a white solid.

$^1$H NMR (CDCl$_3$) δ 9.53 (s, 1H), 8.16 (s, 1H), 8.00 (d, J=0.6 Hz, 1H), 7.79 (d, J=0.6 Hz, 1H), 6.27 (s, 1H), 3.40 (dd, J=6.0 Hz, 1.8 Hz, 1H), 1.67 (s, 3H)

MS (m/z): M+ (463)

Example 47

3,5-Dimethyl-4,5-dihydro-3H-pyrazole-3-carboxylic acid (4-cyano-3-trifluoromethyl-phenyl)-amide and 3,5-Dimethyl-3,4-dihydro-2H-pyrazole-3-carboxylic acid (4-cyano-3-trifluoromethyl-phenyl)-amide Compound #97 and Compound #60

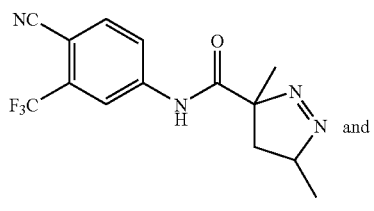

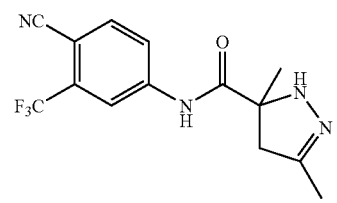

Diazoethane (~0.5 M, 20 mL) in diethyl ether (which may be prepared by according to known methods) was added into 2-methyl-N-(4-cyano-3-trifluoromethyl-phenyl)-acrylamide (250 mg, 1 mmoL) in THF (2 mL) at room temperature. The solution was stirred at room temperature for 72 hours. The solvent was removed and the residue was purified by column chromatography to yield the title compounds as a white solids.

3,5-Dimethyl-4,5-dihydro-3H-pyrazole-3-carboxylic acid (4-cyano-3-trifluoromethyl-phenyl)-amide $^1$H NMR (CDCl$_3$) δ 9.06 (s, 1H), 8.16 (s, 1H), 7.99 (d, J=0.6 Hz, 1H), 7.82 (d, J=0.6 Hz, 1H), 4.58 (m, 1H), 2.06 (dd, J=1.3 Hz, 0.5 Hz, 1H), 1.59 (m, 1H), 1.56 (s, 3H)

MS (m/z): MNa+ (333)

3,5-Dimethyl-3,4-dihydro-2H-pyrazole-3-carboxylic acid (4-cyano-3-trifluoromethyl-phenyl)-amide $^1$H NMR (CDCl$_3$) δ 9.85 (s, br, 1H0, 8.05 (s, 1H), 7.95 (d, J=7.5 Hz, 1H), 7.75 (d, J=7.5 Hz, 1H), 2.95 (abq, J=12.5 Hz, 2H), 1.98 (s, 3H), 1.55 (s, 3H)

MS (m/z): MH+ (311), MH− (309).

Example 48

5-Ethyl-3-methyl-3,4-dihydro-2H-pyrazole-3-carboxylic acid (4-cyano-3-trifluoromethyl-phenyl)-amide and 5-Ethyl-3-methyl-4,5-dihydro-3H-pyrazole-3-carboxylic acid (4-cyano-3-trifluoromethyl-phenyl)-amide Compound #15 and Compound #58

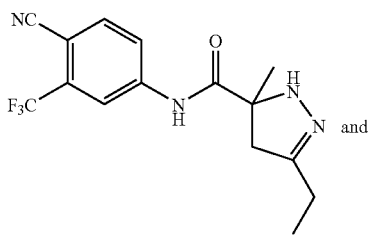

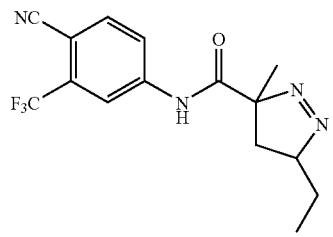

Following the procedure described in Example 29, the mixture of 4-methyl-2-[(1E)-propylidene]benzenesulfonyl hydrazone was reacted to yield the two title compounds as a white solids.

5-Ethyl-3-methyl-4,5-dihydro-3H-pyrazole-3-carboxylic acid (4-cyano-3-trifluoromethyl-phenyl)-amide (Hexane:Ethyl Acetate, 2:1, Rf=0.30)

$^1$H NMR (CDCl$_3$) δ 9.09 (s, 1H), 8.18 (s, 1H), 8.00 (d, J=0.6 Hz, 1H), 7.98 (d, J=0.6 Hz, 1H), 4.48 (m, 1H), 2.10 (m, 2H), 2.00 (m, 1H), 1.65 (m, 1H), 1.56 (s, 3H), 1.01 (t, J=0.7 Hz, 3H)

MS (m/z): MNa+ (347)

5-Ethyl-3-methyl-3,4-dihydro-2H-pyrazole-3-carboxylic acid (4-cyano-3-trifluoromethyl-phenyl)-amide (Hexane:Ethyl Acetate, 2:1, Rf=0.10)

$^1$H NMR (CDCl$_3$) δ 9.89 (s, 1H), 8.14 (s, 1H), 7.95 (d, J=0.6 Hz, 1H), 7.80 (d, J=0.6 Hz, 1H), 5.33 (m, 1H), 2.95 (dd, J=6.0 Hz, 1.4 Hz, 2H), 2.35 (q, J=0.6 Hz, 2H), 1.58 (s, 3H), 1.18 (t, J=0.6 Hz, 3H)

MS (m/z): MNa+ (347)

Example 49

5-Isobutyl-3-methyl-3,4-dihydro-2H-pyrazole-3-carboxylic acid (4-cyano-3-trifluoromethyl-phenyl)-amide and 5-Isobutyl-3-methyl-4,5-dihydro-3H-pyrazole-3-carboxylic acid (4-cyano-3-trifluoromethyl-phenyl)-amide Compound #11 and Compound #61

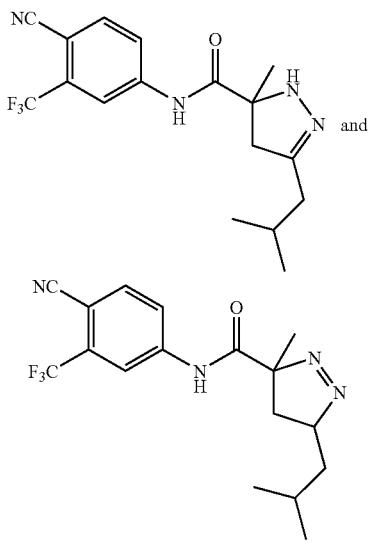

Following the procedure described in Example 29, 4-methyl-2-[(1E)-3-methylbutylidene]benzenesulfonyl hydrazone was reacted to yield the two title compounds as a white solids.

5-Isobutyl-3-methyl-4,5-dihydro-3H-pyrazole-3-carboxylic acid (4-cyano-3-trifluoromethyl-phenyl)-amide (Hexane:Ethyl Acetate, 2:1, Rf=0.80)

$^1$H NMR (CDCl$_3$) δ 9.10 (s, 1H), 8.17 (s, 1H), 8.00 (d, J=0.6 Hz, 1H), 7.82 (d, J=0.6 Hz, 1H), 4.55 (q, J=0.5 Hz, 1H), 2.00 (m, 3H), 1.60 (m, 1H), 1.57 (s, 3H), 1.39 (m, 1H), 1.04 (t, J=0.5 Hz, 3H)

MS (m/z): MNa+ (375)

5-Isobutyl-3-methyl-3,4-dihydro-2H-pyrazole-3-carboxylic acid (4-cyano-3-trifluoromethyl-phenyl)-amide (Hexane:Ethyl Acetate, 2:1, Rf=0.20)

$^1$H NMR (CDCl$_3$) δ 9.86 (s, 1H), 8.12 (s, 1H), 7.93 (d, J=0.6 Hz, 1H), 7.77 (d, J=0.6 Hz, 1H), 5.39 (br, 1H), 2.90 (dd, J=5.4 Hz, 1.3 Hz, 2H), 2.19 (d, J=0.5 Hz, 2H), 1.91 (m, 1H), 1.57 (s, 3H), 0.93 (m, 6H)

MS (m/z): M+ (353)

Example 50

3-Methyl-5-(2-methylsulfanyl-ethyl)-4,5-dihydro-3H-pyrazole-3-carboxylic acid (4-cyano-3-trifluoromethyl-phenyl)-amide Compound #59

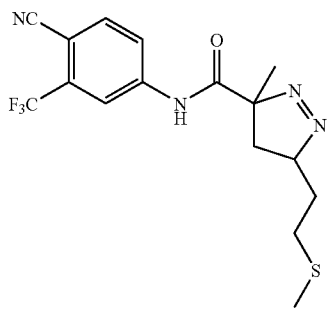

Following the procedure described in Example 29, 4-methyl-2-[(1E)-3-(methylthio)propylidene]benzenesulfonyl hydrazone was reacted to yield the title compound as a white solid.

$^1$H NMR (CDCl$_3$) δ 9.02 (s, 1H), 8.15 (s, 1H), 7.98 (d, J=0.6 Hz, 1H), 7.82 (d, J=0.6 Hz, 1H), 4.71 (q, J=0.5 Hz, 1H), 2.82 (m, 2H), 2.35 (m, 1H), 2.11 (s, 3H), 2.08 (m, 1H), 1.95 (m, 1H), 1.60 (m, 1H), 1.57 (s, 3H)

MS (m/z): MNa+ (393).

Example 51

3-Methyl-5-propyl-3,4-dihydro-2H-pyrazole-3-carboxylic acid (4-cyano-3-trifluoromethyl-phenyl)-amide and 3-Methyl-5-propyl-4,5-dihydro-3H-pyrazole-3-carboxylic acid (4-cyano-3-trifluoromethyl-phenyl)-amide Compound #14 and Compound #62

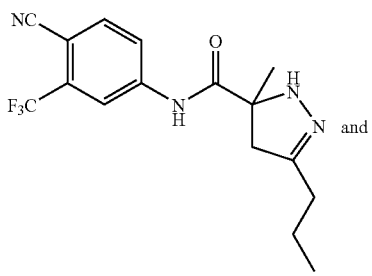

-continued

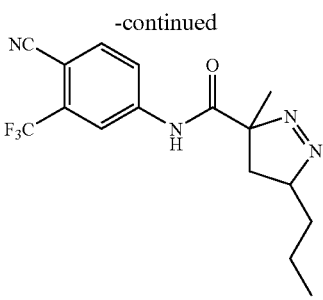

Following the procedure described in Example 29, 4-methyl-2-[(1E)-butylidene]benzenesulfonyl hydrazone was reacted to yield the two title compounds as a white solids.

3-Methyl-5-propyl-4,5-dihydro-3H-pyrazole-3-carboxylic acid (4-cyano-3-trifluoromethyl-phenyl)-amide (Hexane:Ethyl Acetate, 2:1, Rf=0.70)
$^1$H NMR (CDCl$_3$) δ 9.11 (s, 1H), 8.11 (s, 1H), 7.93 (d, J=0.6 Hz, 1H), 7.70 (d, J=0.6 Hz, 1H), 4.42 (q, J=0.5 Hz, 1H), 2.00 (m, 3H), 1.60 (m, 3H), 1.49 (s, 3H), 1.00 (t, J=0.5 Hz, 3H)
MS (m/z): M+ (338)

3-Methyl-5-propyl-3,4-dihydro-2H-pyrazole-3-carboxylic acid (4-cyano-3-trifluoromethyl-phenyl)-amide (Hexane:Ethyl Acetate, 2:1, Rf=0.15)
$^1$H NMR (CDCl$_3$) δ 9.88 (s, 1H), 8.13 (s, 1H), 7.95 (d, J=0.6 Hz, 1H), 7.79 (d, J=0.6 Hz, 1H), 5.39 (s, 1H), 2.90 (dd, J=5.8, 1.2 Hz, 2H), 2.29 (t, J=0.6 Hz, 2H), 1.57 (m, 2H), 1.56 (s, 3H), 0.95 (t, J=0.5 Hz, 3H)
MS (m/z): M+ (338).

Example 52

5-(4-Acetylamino-phenyl)-3-methyl-3,4-dihydro-2H-pyrazole-3-carboxylic acid (4-cyano-3-trifluoromethyl-phenyl)-amide Compound #33

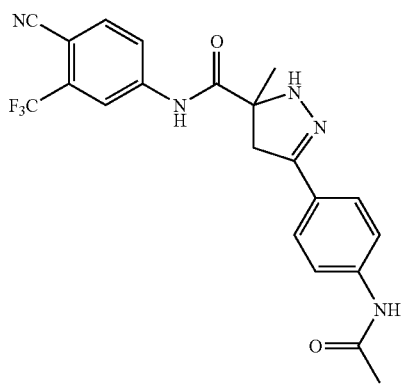

Following the procedure described in Example 29, 4-methyl-2-[(1E)-4-(acetamidophenyl)methylidene]benzenesulfonyl hydrazone was reacted with 2-methyl-N-(4-cyano-3-trifluoromethyl-phenyl)-acrylamide to yield the title compound as a white solid.

$^1$H NMR (CDCl$_3$) δ 9.70 (s, 1H), 8.11 (s, 1H), 7.93-7.79 (m, 2H), 7.55 (s, 4H), 5.65 (s, 1H), 3.82 (dd, J=4.8, 2.4 Hz, 2H), 2.20 (s, 3H), 2.00 (s, 3H).
MS (m/z): M+ (430)

Example 53

5-(4-Acetylamino-phenyl)-3-methyl-3,4-dihydro-2H-pyrazole-3-carboxylic acid (4-nitro-3-trifluoromethyl-phenyl)-amide Compound #34

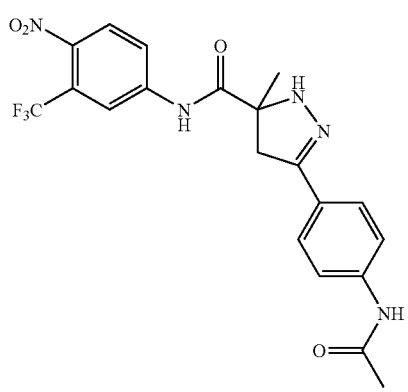

Following the procedure described in Example 29, 4-methyl-2-[(1E)-4-(acetamidophenyl)methylidene]benzenesulfonyl hydrazone was reacted with 2-methyl-N-(4-nitro-3-trifluoromethyl-phenyl)-acrylamide to yield the title compound as a yellow solid.

$^1$H NMR (CDCl$_3$) δ 8.30 (s, 1H), 8.15-8.01 (m, 2H), 7.58 (m, 4H), 3.82 (dd, J=7.5, 2.4 Hz, 2H), 2.05 (s, 3H), 2.00 (s, 3H).
MS (m/z): M+ (450), M− (448)

Example 54

3-Methyl-5-trifluoromethyl-3,4-dihydro-2H-pyrazole-3-carboxylic acid (4-cyano-phenyl)-amide Compound #20

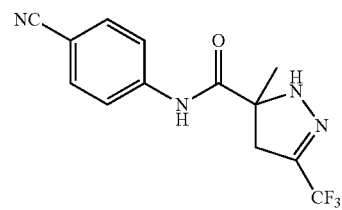

Following the procedure described in Example 29, 4-methyl-2-[(1E)-2,2,2-trifluoroethylidene]benzenesulfonyl hydrazone was reacted with 2-methyl-N-(4-cyano-phenyl)-acrylamide to yield the title compound as a yellow solid.

$^1$H NMR (CDCl$_3$) δ 9.05 (s, 1H), 7.70-7.60 (m, 4H), 5.95 (s, 1H), 3.15 (dd, J=6.0, 2.4 Hz, 2H), 1.60 (s, 3H).
MS (m/z): M− (295)

Example 55

3-Methyl-5-trifluoromethyl-3,4-dihydro-2H-pyrazole-3-carboxylic acid (4-chloro-3-trifluoromethyl-phenyl)-amide Compound #23

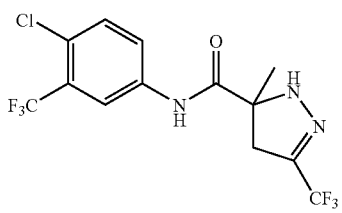

Following the procedure described Example 29, 4-methyl-2-[(1E)-2,2,2-trifluoroethylidene]benzenesulfonyl hydrazone was reacted with 2-methyl-N-(4-cyano-3-chloro-phenyl)-acrylamide to yield the title compound as a yellow solid.

$^1$H NMR (CDCl$_3$) δ 8.95 (s, 1H), 7.95 (s, 1H), 7.75 (m, 1H), 7.50 (m, 1H), 6.00 (s, 1H), 3.15 (dd, J=6.0, 2.4 Hz, 2H), 1.60 (s, 3H).

MS (m/z): MH+ (374)

Example 56

3-Methyl-5-trifluoromethyl-3,4-dihydro-2H-pyrazole-3-carboxylic acid (3,4-dichloro-phenyl)-amide Compound #24

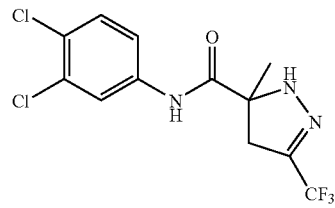

Following the procedure described in Example 29, 4-methyl-2-[(1E)-2,2,2-trifluoroethylidene]benzenesulfonyl hydrazone was reacted with 2-methyl-N-(3,4-dichlorophenyl)-acrylamide to yield the title compound as a yellow solid.

$^1$H NMR (CDCl$_3$) δ 8.85 (s, 1H), 7.85 (s, 1H), 7.40 (m, 2H), 5.85 (s, 1H), 3.15 (dd, J=6.0, 2.4 Hz, 2H), 1.60 (s, 3H).
MS (m/z): MH+ (341).

Example 57

3-Methyl-5-trifluoromethyl-3,4-dihydro-2H-pyrazole-3-carboxylic acid (4-benzyl-phenyl)-amide Compound #18

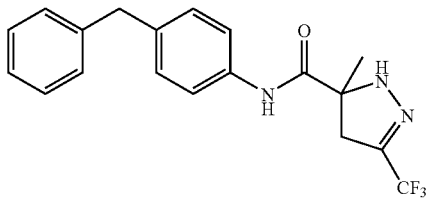

Following the procedure described in Example 29, 4-methyl-2-[(1E)-2,2,2-trifluoroethylidene]benzenesulfonyl hydrazone was reacted with N-(4-Benzyl-phenyl)-2-methyl-acrylamide to yield the title compound as a yellow solid.

$^1$H NMR (CDCl$_3$) δ 8.60 (s, 1H), 8.00 (m, 1H), 7.30-7.10 (m, 8H), 5.40 (s, 1H), 4.00 (s, 2H), 2.70 (s, 2H), 1.38 (s, 3H).

MS (m/z): MH+ (362)

Example 58

3-Methyl-5-trifluoromethyl-3,4-dihydro-2H-pyrazole-3-carboxylic acid (4-benzoyl-phenyl)-amide Compound #17

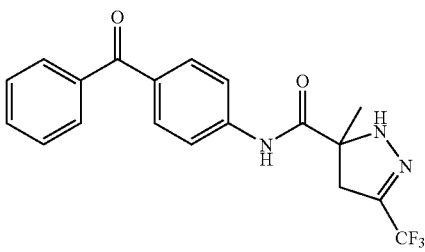

Following the procedure described in Example 29, 4-methyl-2-[(1E)-2,2,2-trifluoroethylidene]benzenesulfonyl hydrazone was reacted with N-(4-benzoyl-phenyl)-2-methyl-acrylamide to yield the title compound as a yellow solid.

$^1$H NMR (CDCl$_3$) δ 9.00 (s, 1H), 7.85 (m, 2H), 7.75 (m, 2H), 7.58 (m, 5H), 5.90 (s, 1H), 3.15 (dd, J=6.5, 2.1 Hz, 2H), 1.60 (s, 3H).

MS (m/z): MH+ (376)

Example 59

3-Methyl-5-trifluoromethyl-3,4-dihydro-2H-pyrazole-3-carboxylic acid (4-phenoxy-phenyl)-amide Compound #19

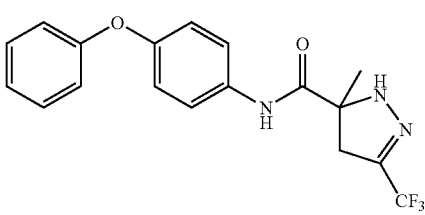

Following the procedure described in Example 29, the title compound was prepared as a white solid.

$^1$H NMR (CDCl$_3$) δ 8.75 (s, 1H), 7.55 (m, 2H), 7.30 (m, 2H), 7.10 (m, 5H), 5.75 (s, 1H), 3.15 (dd, J=6.4, 2.1 Hz, 2H), 1.55 (s, 3H).

MS (m/z): MH+ (364).

Example 60

3-Ethyl-5-trifluoromethyl-3,4-dihydro-2H-pyrazole-3-carboxylic acid (4-cyano-3-trifluoromethyl-phenyl)-amide Compound #30

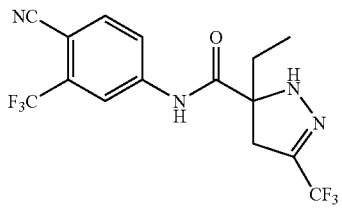

Following the procedure described Example 29, the title compound was obtained as a white solid.

$^1$H NMR (CDCl$_3$) δ 9.37 (s, 1H), 8.11 (s, 1H), 7.95-7.80 (m, 2H), 6.10 (s, 1H), 3.22 (dd, J=6.0, 2.7 Hz, 2H), 2.05 (m, 2H), 1.00 (t, J=1.5 Hz, 3H).

MS (m/z): MH+ (379).

Example 61

3-Propyl-5-trifluoromethyl-3,4-dihydro-2H-pyrazole-3-carboxylic acid (4-cyano-3-trifluoromethyl-phenyl)-amide Compound #73

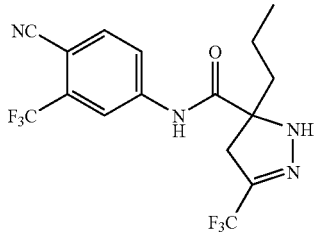

Following the procedure described in Example 29, the title compound was obtained as a white solid.

$^1$H NMR (CDCl$_3$) δ 9.30 (s, 1H), 8.15 (s, 1H), 7.95 (m, 1H), 7.80 (m, 1H), 6.25 (s, 1H), 3.15 (dd, J=6.0, 2.7 Hz, 2H), 2.00 (m, 2H), 1.30 (m, 2H), 1.65 (t, J=1.0 Hz, 3H)

MS (m/z): MH+ (393).

Example 62

3-Methyl-5-trifluoromethyl-3,4-dihydro-2H-pyrazole-3-carboxylic acid 4-methanesulfonyl-benzylamide Compound #27

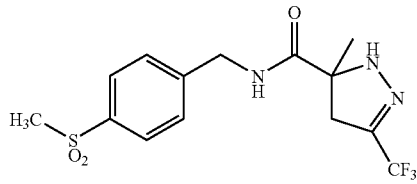

Following the procedure described in Example 29, the title compound was obtained as a white solid.

$^1$H NMR (CDCl$_3$) δ 7.90 (m, 2H), 7.45 (m, 2H), 6.75 (s, 1H), 4.50 (m, 2H), 3.05 (s, 3H), 3.00 (dd, J=6.0, 2.7 Hz, 2H), 1.55 (s, 3H).

MS (m/z): MH+ (364).

Example 63

3-Methyl-5-trifluoromethyl-3,4-dihydro-2H-pyrazole-3-carboxylic acid (4-phenylsulfanyl-phenyl)-amide Compound #28

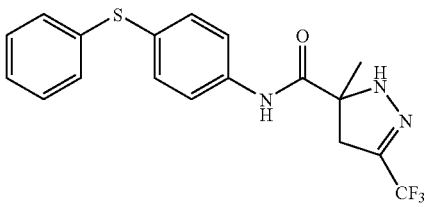

Following the procedure described in Example 29, the title compound was obtained as a white solid.

$^1$H NMR (CDCl$_3$) δ 8.75 (s, 1H), 7.55 (m, 2H), 7.35 (m, 2H), 7.23 (m, 5H), 5.70 (s, 1H), 3.00 (dd, J=8.4, 2.4 Hz, 2H), 1.60 (s, 3H).

MS (m/z): MH+ (380)

Example 64

3-Methyl-5-trifluoromethyl-3,4-dihydro-2H-pyrazole-3-carboxylic acid (4-benzenesulfonyl-phenyl)-amide Compound #32

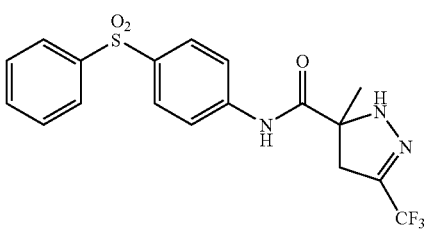

3-Methyl-5-trifluoromethyl-3,4-dihydro-2H-pyrazole-3-carboxylic acid (4-phenylsulfanyl-phenyl)-amide (100 mg, 0.264 mmoL) in EtOAc (2 mL) at room temperature was treated with Oxone (1.0 g) in water (10 mL). Sat. NaHCO$_3$ was added to adjust pH 7~8. The reaction mixture was stirred for 2 hrs. The mixture was then partitioned between ethyl acetate and water. The organic layers were combined and dried over Na$_2$SO$_4$, concentrated and purified by silica gel column using ethyl acetate as eluent to afford the title product.

$^1$H NMR (CDCl$_3$) δ 8.50 (s, 1H), 7.55 (m, 4H), 7.45 (m, 5H), 2.90 (dd, J=6.4, 2.1 Hz, 2H), 1.80 (s, 3H).

MS (m/z): MNa+ (432).

Example 65

3-Methyl-5-trifluoromethyl-3,4-dihydro-2H-pyrazole-3-carboxylic acid 4-chloro-benzylamide Compound #29

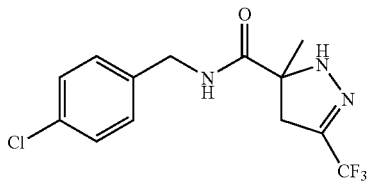

Following the procedure described in Example 29, the title compound was obtained as a white solid.

$^1$H NMR (CDCl$_3$) δ 7.35 (m, 4H), 5.70 (s, 1H), 4.50 (m, 2H), 3.00 (dd, J=6.0, 2.1 Hz, 2H), 1.50 (s, 3H).

MS (m/z): MH+ (319).

Example 66

5-(3,4-Difluoro-phenyl)-3-methyl-3,4-dihydro-2H-pyrazole-3-carboxylic acid (4-cyano-3-trifluoromethyl-phenyl)-amide and 5-(3,4-Difluoro-phenyl)-3-methyl-4,5-dihydro-3H-pyrazole-3-carboxylic acid (4-cyano-3-trifluoromethyl-phenyl)-amide Compound #2 and compound #53

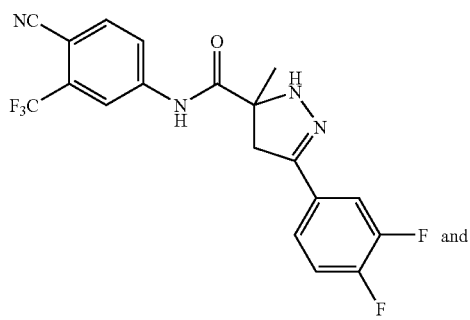

and

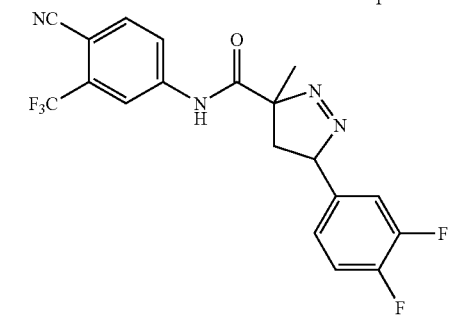

Following the procedure described in Example 29, the title compounds were obtained as white solids.

5-(3,4-Difluoro-phenyl)-3-methyl-3,4-dihydro-2H-pyrazole-3-carboxylic acid (4-cyano-3-trifluoromethyl-phenyl)-amide MS (m/z): M+1 (409).

5-(3,4-Difluoro-phenyl)-3-methyl-4,5-dihydro-3H-pyrazole-3-carboxylic acid (4-cyano-3-trifluoromethyl-phenyl)-amide MS (m/z): M+1 (409)

Example 67

3-Methyl-5-(2,2,2-trifluoro-ethyl)-3,4-dihydro-2H-pyrazole-3-carboxylic acid (4-cyano-3-trifluoromethyl-phenyl)-amide Compound #75

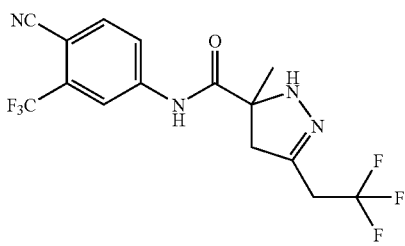

Following the procedure described in Example 29, the title compound was obtained as a white solid.

$^1$H NMR (CDCl$_3$) δ 9.60 (s, 1H), 8.15 (s, 1H), 7.95 (m, 1H), 7.80 (m, 1H), 5.65 (s, 1H), 3.20 (m, 2H), 3.05 (dd, J=6.0, 2.4 Hz, 2H), 1.55 (s, 3H).

MS (m/z): MH+ (379).

Example 68

5-Cyclopentyl-3-methyl-3,4-dihydro-2H-pyrazole-3-carboxylic acid (4-cyano-3-trifluoromethyl-phenyl)-amide Compound #48

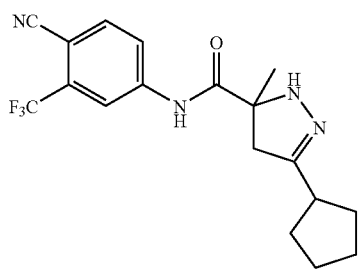

Following the procedure described in Example 29, the title compound was obtained as a white solid.

¹H NMR (CDCl₃) δ 9.85 (s, 1H), 8.10 (s, 1H), 7.95 (m, 1H), 7.80 (m, 1H), 5.20 (s, 1H), 2.80 (dd, J=7.8, 2.4 Hz, 2H), 1.60 (m, 1H), 1.55 (s, 3H). MS (m/z): MH+ (365).

Example 69

5-(2-Fluoro-3-hydroxy-phenyl)-3-methyl-3,4-dihydro-2H-pyrazole-3-carboxylic acid (4-cyano-3-trifluoromethyl-phenyl)-amide Compound #12

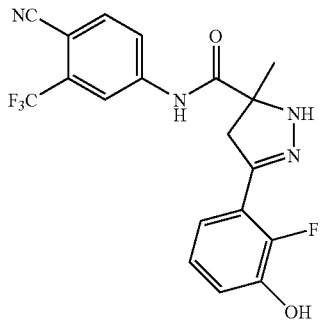

Following the procedure described in Example 29, the title compound was obtained as a white solid.

¹H NMR (CDCl₃) δ 8.00 (s, 1H), 7.95 (m, 2H), 7.82 (s, 1H), 7.60 (m, 2H), 7.35 (m, 2H), 7.15 (m, 2H), 3.60 (dd, J=25.0 Hz, 12.0 Hz, 2H), 1.35 (s, 3H)

MS (m/z): M+1 (400).

Example 70

3-Methyl-5-pyridin-3-yl-3,4-dihydro-2H-pyrazole-3-carboxylic acid (4-cyano-3-trifluoromethyl-phenyl)-amide Compound #77

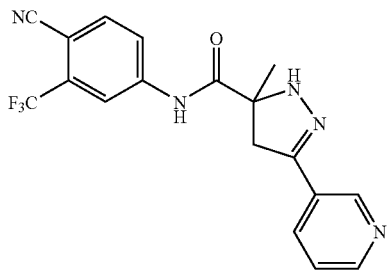

Following the procedure described in Example 29, the title compound was obtained as a white solid.

¹H NMR (CDCl₃) δ 9.70 (s, 1H), 8.80 (s, 1H), 8.60 (m, 1H), 8.10 (s, 1H), 8.00 (m, 2H), 7.80 (m, 1H), 7.35 (m, 1H), 6.00 (s, 1H), 3.35 (dd, J=5.7, 2.4 Hz, 2H), 1.65 (s, 3H). MS (m/z): MH+ (374).

Example 71

5-(4-Fluoro-phenyl)-3-methyl-3,4-dihydro-2H-pyrazole-3-carboxylic acid (4-chloro-3-trifluoromethyl-phenyl)-amide Compound #13

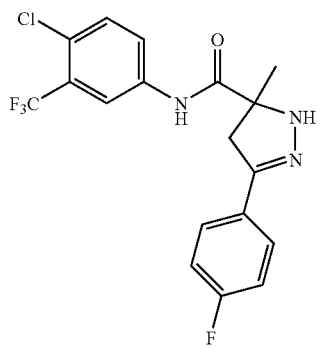

Following the procedure described in Example 29, the title compound was obtained as a white solid.

¹H NMR (CDCl₃) δ 7.80 (s, 1H), 7.45 (d, J=9.0 Hz, 1H), 6.80 (d, J=9.0 Hz, 1H), 3.60 (dd, J=30.0 Hz, 18.0 Hz, 2H), 1.50 (s, 3H), 1.20 (s, 3H).

MS (m/z): M+1 (288).

Example 72

5-(4-Acetylamino-phenyl)-3-methyl-3,4-dihydro-2H-pyrazole-3-carboxylic acid (4-chloro-3-trifluoromethyl-phenyl)-amide Compound #44

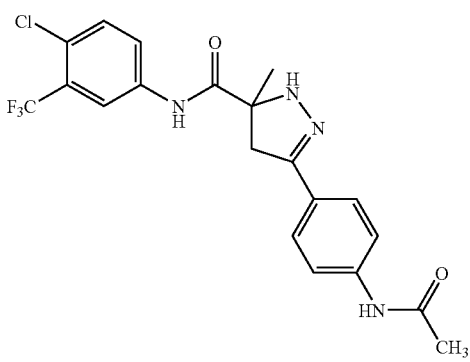

Following the procedure described in Example 29, the title compound was obtained as a white solid.

¹H NMR (CDCl₃) δ 9.50 (s, 1H), 8.00 (s, 1H), 7.90 (s, 1H), 7.75 (m, 1H), 7.50 (s, 4H), 7.45 (m, 1H), 5.70 (s, 1H), 3.25 (dd, J=5.4, 2.7 Hz, 2H), 2.15 (s, 3H), 1.60 (s, 3H). MS (m/z): MH+ (439).

Example 73

3-Methyl-5-[4-(2,2,2-trifluoro-acetylamino)-phenyl]-3,4-dihydro-2H-pyrazole-3-carboxylic acid (4-chloro-3-trifluoromethyl-phenyl)-amide Compound #46

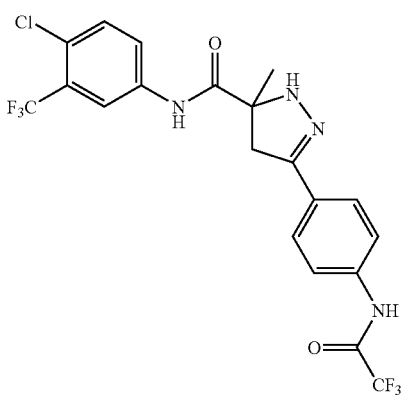

Following the procedure described in Example 29, the title compound was obtained as a white solid.

$^1$H NMR (CDCl$_3$) δ 9.50 (s, 1H), 8.80 (s, 1H), 8.00 (s, 1H), 7.75 (m, 1H), 7.65 (s, 4H), 7.45 (m, 1H), 5.80 (s, 1H), 3.20 (dd, J=5.4, 2.4 Hz, 2H), 1.60 (s, 3H). MS (m/z): MH+ (492).

Example 74

5-(4-Acetylamino-benzyl)-3-methyl-3,4-dihydro-2H-pyrazole-3-carboxylic acid (4-cyano-3-trifluoromethyl-phenyl)-amide Compound #43

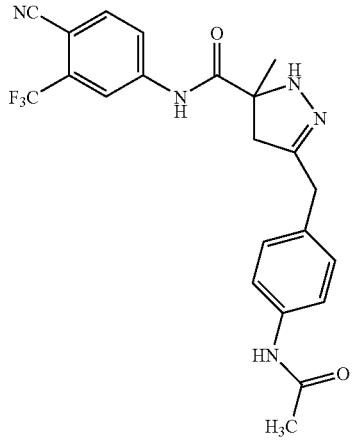

Following the procedure described in Example 29, the title compound was obtained as a white solid.

$^1$H NMR (CDCl$_3$) δ 9.80 (s, 1H), 8.10 (s, 1H), 8.00 (s, 1H), 7.95 (m, 1H), 7.75 (s, 1H), 7.55 (s, 4H), 5.75 (s, 1H), 3.30 (dd, J=5.4, 2.4 Hz, 2H), 2.20 (s, 2H), 1.60 (s, 3H). MS (m/z): MNa+ (468).

Example 75

Acetic acid 4-[5-(4-cyano-3-trifluoromethyl-phenyl-carbamoyl)-5-methyl-4,5-dihydro-1H-pyrazol-3-yl]-phenyl ester Compound #45

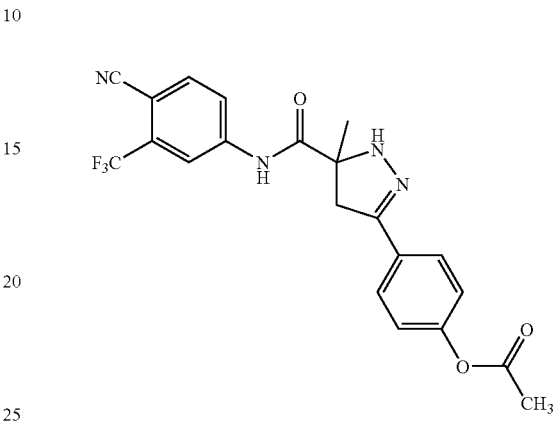

Following the procedure described in Example 29, the title compound was obtained as a white solid.

$^1$H NMR (CDCl$_3$) δ 9.80 (s, 1H), 8.10 (s, 1H), 7.95 (m, 1H), 7.80 (m, 1H), 7.55 (d, J=1.0 Hz, 2H), 6.85 (d, J=1.0 Hz, 2H), 5.60 (s, 1H), 3.30 (dd, J=5.4, 2.4 Hz, 2H), 2.0 (s, 3H), 1.60 (s, 3H). MS (m/z): MH+ (431).

Example 76

5-(3-Acetylamino-phenyl)-3-methyl-3,4-dihydro-2H-pyrazole-3-carboxylic acid (4-cyano-3-trifluoromethyl-phenyl)-amide Compound #41

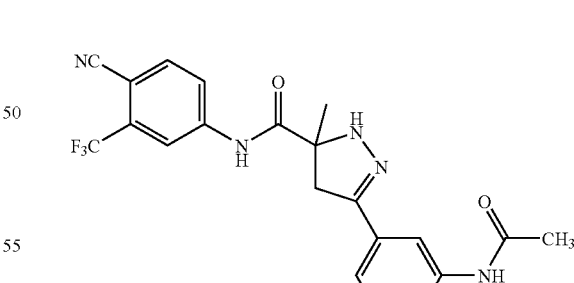

Following the procedure described in Example 29, the title compound was obtained as a white solid.

$^1$H NMR (CDCl$_3$) δ 9.75 (s, 1H), 8.15 (s, 1H), 8.00-7.75 (m, 4H), 7.40 (m, 1H), 7.25 (s, 1H), 5.80 (s, 1H), 3.25 (dd, J=5.4, 2.4 Hz, 2H), 2.20 (s, 3H), 1.60 (s, 3H). MS (m/z): MH+ (431).

Example 77

3-Methyl-5-trifluoromethyl-3,4-dihydro-2H-pyrazole-3-carboxylic acid (4-nitro-3-trifluoromethyl-phenyl)-amide Compound #74

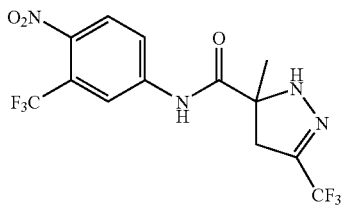

Following the procedure described in Example 29, the title compound was obtained as a white solid.
$^1$H NMR (CDCl$_3$) δ 9.30 (s, 1H), 8.10 (s, 1H), 8.00 (m, 2H), 6.10 (s, 1H), 3.15 (dd, J=6.0, 2.4 Hz, 2H), 1.66 (s, 3H).
MS (m/z): MH+ (385).

Example 78

5-tert-Butyl-3-methyl-3,4-dihydro-2H-pyrazole-3-carboxylic acid (4-cyano-3-trifluoromethyl-phenyl)-amide Compound #86

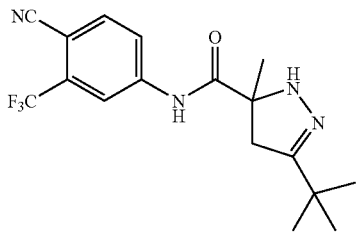

Following the procedure described in Example 29, the title compound was obtained as a white solid.
$^1$H NMR (CDCl$_3$) δ 9.78 (br, s, 1H), 8.12 (s, 1H), 7.92 (d, J=7.5 Hz, 1H), 7.78 (d, J=7.5 Hz, 1H), 5.25 (br, s, 1H), 2.95 (abq, J=12.5 Hz, 2H), 1.58 (s, 3H), 1.15 (s, 9H).
MS (m/z): MH+ (353), MH− (351).

Example 79

5-tert-Butyl-3-methyl-3,4-dihydro-2H-pyrazole-3-carboxylic acid (4-nitro-3-trifluoromethyl-phenyl)-amide Compound #89

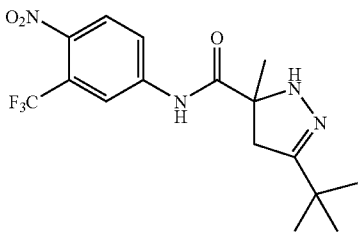

Following the procedure described in Example 29, the title compound was obtained as a white solid.
$^1$H NMR (CDCl$_3$) δ 8.01 (d, J=7.0 Hz, 1H), 7.62 (s, 1H), 7.05 (d, J=7.0 Hz, 1H), 6.10 (s, 1H), 5.48 (s, 1H), 3.25 (abq, J=12.5 Hz, 2H), 1.52 (s, 3H), 1.25 (s, 9H).
MS (m/z): MH+ (373), MH− (371).

Example 80

5-(4-Cyano-3-trifluoromethyl-phenylcarbamoyl)-5-methyl-4,5-dihydro-1H-pyrazole-3-carboxylic acid ethyl ester Compound #84

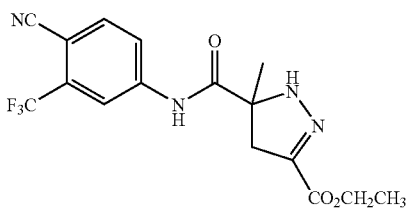

Following the procedure described in Example 31, the title compound was obtained as a white solid.
$^1$H NMR (CDCl$_3$) δ 99.18 (s, br, 1H), 8.11 (s, 1H), 7.98 (d, J=7.2 Hz, 1H), 7.81 (d, J=7.2 Hz, 1H), 6.25 (s, 1H), 4.32 (q, J=8.5 Hz, 2H), 3.25 (abq, J=12.5 Hz, 2H), 1.62 (s, 3H), 1.45 (t, J=8.5 Hz, 3H).
MS (m/z): MH+ (369), MH− (367).

Example 81

5-(4-Nitro-3-trifluoromethyl-phenylcarbamoyl)-5-methyl-4,5-dihydro-1H-pyrazole-3-carboxylic acid ethyl ester Compound #83

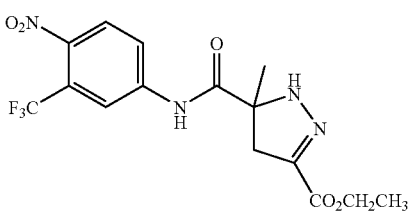

Following the procedure described in Example 31, the title compound was obtained as a white solid.
$^1$H NMR (CDCl$_3$) δ 9.22 (s, br, 1H), 8.11 (s, 1H), 8.02 (d, J=6.5 Hz, 1H), 8.00 (d, J=6.5 Hz, 1H), 6.38 (s, 1H), 4.32 (q, J=8.5 Hz, 2H), 3.25 (abq, J=12.5 Hz, 2H), 1.61 (s, 3H), 1.48 (t, J=8.5 Hz, 3H).
MS (m/z): MH+ (389), MNa+ (411).

Example 82

5-(4-Bromo-3-trifluoromethyl-phenylcarbamoyl)-5-methyl-4,5-dihydro-1H-pyrazole-3-carboxylic acid ethyl ester Compound #85

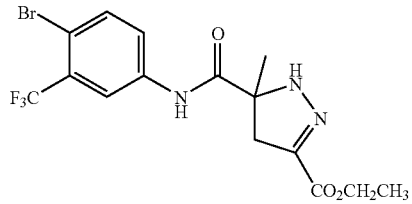

Following the procedure described in Example 31, the title compound was obtained as a white solid.

$^1$H NMR (CDCl$_3$) δ 8.95 (s, br, 1H), 7.98 (s, 1H), 7.65 (m, 2H), 6.35 (s, br, 1H), 4.33 (q, J=7.8 Hz, 2H), 3.15 (abq, J=10.5 z, 2H), 1.58 (s, 3H), 1.48 (t, J=7.8 Hz, 2H).

MS (m/z): MH+ (423)

Example 83

3-Methyl-5-[4-(2,2,2-trifluoro-acetylamino)-phenyl]-3,4-dihydro-2H-pyrazole-3-carboxylic acid (4-nitro-3-trifluoromethyl-phenyl)-amide Compound #37

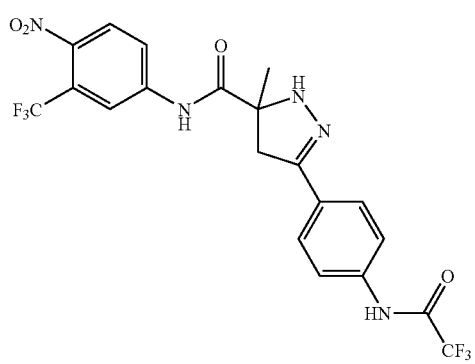

Following the procedure described in Example 29, the title compound was obtained as a white solid.

$^1$H NMR (C$_6$D$_6$) δ8.95 (s, 1H), 7.62 (s, 1H), 7.50 (d, J=7.8 Hz, 2H), 7.35 (d, J=7.0 Hz, 1H), 7.20 (d, J=7.5 Hz, 2H), 7.18 (d, J=7.0 Hz, 1H), 4.95 (s, 1H), 2.80 (abq, J=15.6 Hz, 2H), 1.62 (s, 3H).

MS (m/z): MH+ (504), MH− (502)

Example 84

5-(4-Acetylamino-phenyl)-3-methyl-3,4-dihydro-2H-pyrazole-3-carboxylic acid (3,4-dicyano-phenyl)-amide Compound #38

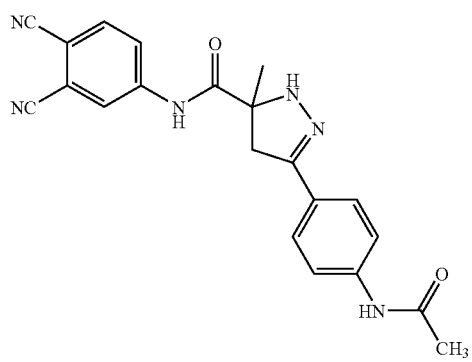

Following the procedure described in Example 29, the title compound was obtained as a white solid.

$^1$H NMR (CDCl$_3$) δ 9.79 (s, br, 1H), 8.25 (s, 1H), 7.88 (d, J=6.8 Hz, 1H), 7.72 (d, J=6.8 Hz, 1H), 7.55 (s, 4H), 5.68 (s, 1H), 3.35 (abq, J=12.5 z, 2H), 2.28 (s, 3H), 1.68 (s, 3H).

MS (m/z): MH+ (387).

Example 85

3-Methyl-3,4-dihydro-2H-pyrazole-3-carboxylic acid (3,4-dichloro-phenyl)-amide

Compound #48

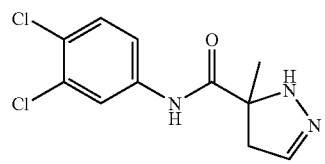

Following the procedure described in Example 31, the title compound was obtained as a white solid.

$^1$H NMR (CDCl$_3$) δ 9.20 (s, 1H), 7.88 (s, 1H), 7.45 (s, 2H), 6.82 (s, 1H), 3.05 (abq, J=12.5 Hz, 2H), 1.58 (s, 3H). MS (m/z): MH+ (273).

Example 86

5-Ethylsulfanyl methyl-3-methyl-3,4-dihydro-2H-pyrazole-3-carboxylic acid (4-cyano-3-trifluoromethyl-phenyl)-amide Compound #87

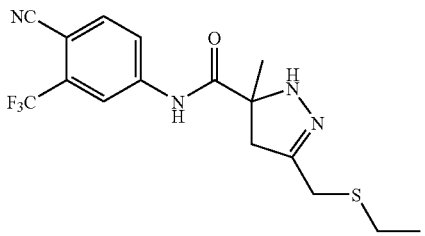

Following the procedure described in Example 29, the title compound was obtained as a white solid.

$^1$H NMR (CDCl$_3$) δ 9.15 (s, br, 1H), 7.95 (s, 1H), 7.75 (m, 2H), 7.55 (s, 1H), 4.35 (abq, J=10.5 Hz, 2H), 3.85 (abq, J=12.5 Hz, 2H), 2.65 (m, J=8.5 Hz, 2H), 1.42 (s, 3H), 1.32 (t, J=8.5 Hz, 3H).

MS (CI) m/z MH+ (371).

Example 87

5-(4-Cyano-3-trifluoromethyl-phenylcarbamoyl)-5-methyl-4,5-dihydro-1H-pyrazole-3-carboxylic acid tert-butyl ester Compound #90

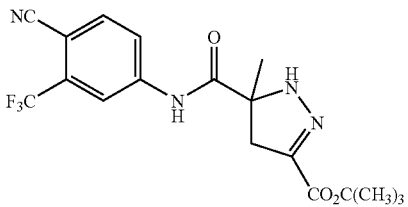

Following the procedure described in Example 31, the title compound was obtained as a white solid.

$^1$H NMR (CDCl$_3$) δ 9.32 (s, br, 1H), 8.12 (s, 1H), 7.95 (d, J=7.5 Hz, 1H), 7.75 (d, J=7.5 Hz, 1H), 6.45 (s, 1H), 3.15 (abq, J=10.5 Hz, 2H), 1.61 (s, 3H), 1.52 (s, 9H).

MS (m/z): MH+ (397).

Example 88

5-(4-Cyano-3-trifluoromethyl-phenylcarbamoyl)-5-methyl-4,5-dihydro-1H-pyrazole-3-carboxylic acid Compound #91

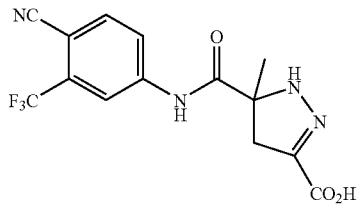

5-(4-Cyano-3-trifluoromethyl-phenylcarbamoyl)-5-methyl-4,5-dihydro-1H-pyrazole-3-carboxylic acid tert-butyl ester (450 mg, 1.135 mmoL) in trifluoroacetic acid (2 mL) and DCM (2 mL) was stirred for 6 hrs at room temperature. The reaction mixture was washed with water and brine. The organic layer was dried over anhydrous Na$_2$SO$_4$, filtered and concentrated to give the title product as a colorless oil.

$^1$H NMR (CDCl$_3$) δ 12.5 (s, br, 1H), 9.11 (s, 1H), 8.09 (s, 1H), 7.98 (d, J=7.5 Hz, 1H), 7.81 (d, J=7.5 Hz, 1H), 3.25 (abq, J=12.5 Hz, 2H), 1.61 (s, 3H).

MS (m/z): MH+ (341)

Example 89

5-Hydroxymethyl-3-methyl-3,4-dihydro-2H-pyrazole-3-carboxylic acid (4-cyano-3-trifluoromethyl-phenyl)-amide Compound #92

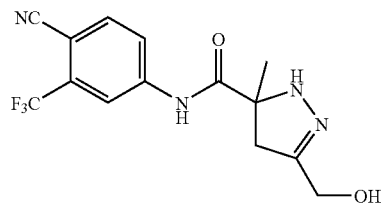

5-(4-Cyano-3-trifluoromethyl-phenylcarbamoyl)-5-methyl-4,5-dihydro-1H-pyrazole-3-carboxylic acid (150 mg, 0.441 mmoL) in THF (2 mL) was treated dropwise with borane-THF complex (882 μL, 0.882 mmoL) at −78° C. over 10 min. The resulting solution was stirred for another 10 min. and then quenched with MeOH. The solvent was removed and the residue was partitioned between water and DCM. The aqueous layer was extracted with DCM (3×). The combined organic layer was washed with brine, dried over anhydrous Na$_2$SO$_4$, filtered and concentrated in vacuo. The crude product was purified by silica gel using 2:1 hexanes:ethyl acetate as eluent to yield the title compound as a white solid.

$^1$H NMR (CDCl$_3$) δ 9.65 (s, 1H), 8.25 (s, 1H), 7.95 (d, J=7.8 Hz, 1H), 7.75 (d, J=7.8 Hz, 1H), 5.50 (s, 1H), 4.25 (abq, J=10.5 Hz, 2H), 2.95 (abq, J=12.5 Hz, 2H), 1.48 (s, 3H).

MS (m/z): MH+ (327).

Example 90

3-Methyl-5-pentafluoroethyl-3,4-dihydro-2H-pyrazole-3-carboxylic acid (4-cyano-3-trifluoromethyl-phenyl)-amide Compound #98

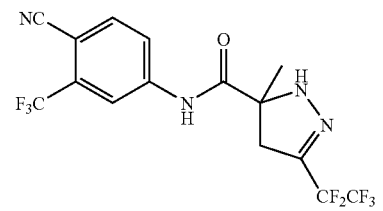

Following the procedure described in Example 31, the title compound was obtained as a white solid.

$^1$H NMR (MeOD) δ 8.21 (s, 1H), 8.10 (d, J=6.5 Hz, 1H), 7.88 (d, J=6.5 Hz, 1H), 3.30 (abq, J=12.5 Hz, 2H), 1.68 (s, 3H).

Example 91

3-Methyl-5-pentafluoroethyl-3,4-dihydro-2H-pyrazole-3-carboxylic acid (4-nitro-3-trifluoromethyl-phenyl)-amide Compound #99

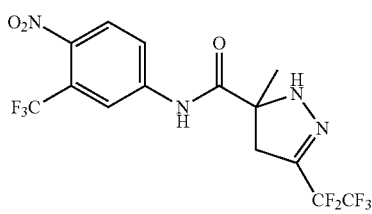

Following the procedure described in Example 31, the title compound was obtained as a white solid.

$^1$H NMR (CDCl$_3$) δ 9.21 (s, br, 1H), 8.12 (s, 1H), 8.02 (s, 2H), 6.05 (s, br, 1H), 3.18 (abq, J=13.5 Hz, 2H), 1.62 (s, 3H)
MS (m/z): MH− (413)

Example 92

3-Methyl-3,4-dihydro-2H-pyrazole-3-carboxylic acid (4-benzoyl-phenyl)-amide and

3-Methyl-5-trimethylsilanyl-pyrazolidine-3-carboxylic acid (4-benzoyl-phenyl)-amide Compound #16 and Compound #63

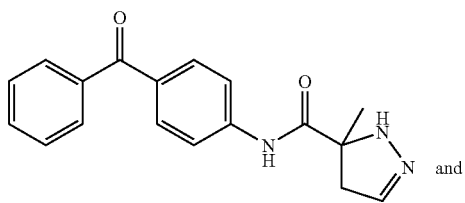

Following the procedure described in Example 31, the title compounds were obtained as white solids.

3-Methyl-3,4-dihydro-2H-pyrazole-3-carboxylic acid (4-benzoyl-phenyl)-amide $^1$H NMR (CDCl$_3$) δ 9.42 (s, br, 1H), 7.85 (d, J=8.5 Hz, 2H), 7.76 (d, J=7.8 Hz, 2H), 7.70 (d, J=8.5 Hz, 2H), 7.65 (t, J=7.8 Hz, 1H), 7.60 (t, J=8.5 Hz, 2H), 6.82 (s, 1H), 5.45 (s, 1H), 3.01 (abq, J=13.5 Hz, 2H), 1.55 (s, 3H).
MS (m/z): MH+ (308), MNa+ (330).

3-methyl-5-trimethylsilanyl-pyrazolidine-3-carboxylic acid (4-benzoyl-phenyl)-amide $^1$H NMR (CDCl$_3$) δ (1:1 isomers) 8.45 (s, 1H, isomer 1), 8.25 (s, 1H, isomer 2), 7.30~7.75 (m, 9H, both isomers), 4.40 (m, 1H, isomer 1), 4.32 (m, 1H, isomer 2), 2.48 (m, 1H, isomer 1), 2.10 (m, 1H, isomer 2), 1.72 (m, 1H, isomer 1), 1.32 (m, 1H, isomer 2), 1.55 (s, 3H, isomer 1), 1.50 (s, 3H, isomer 2), 0.15 (s, 9H, isomer 1), 0.10 (s, 9H, isomer 2).

Example 93

3-Methyl-3,4-dihydro-2H-pyrazole-3-carboxylic acid (4-cyano-phenyl)-amide and

3-methyl-5-trimethylsilanyl-4,5-dihydro-3H-pyrazole-3-carboxylic acid (4-cyano-phenyl)-amide Compound #21 and Compound #65

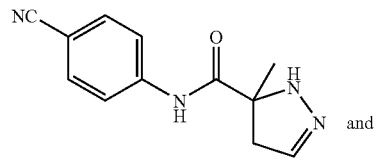

and

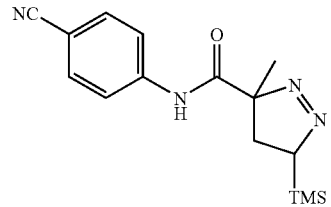

Following the procedure described in Example 31, the title compounds were obtained as white solids.

3-Methyl-3,4-dihydro-2H-pyrazole-3-carboxylic acid (4-cyano-phenyl)-amide $^1$H NMR (CDCl$_3$) δ 9.45 (s, br, 1H), 7.75 (d, J=7.8 Hz, 2H), 7.62 (d, J=7.8 Hz, 2H), 6.85 (s, 1H), 5.45 (s, br, 1H), 3.01 (abq, J=12.5 Hz, 2H), 1.55 (s, 3H).
MS (m/z): MH+ (229), MNa+ (251), MH− (227)

3-Methyl-5-trimethylsilanyl-4,5-dihydro-3H-pyrazole-3-carboxylic acid (4-cyano-phenyl)-amide $^1$H NMR (CDCl$_3$) δ (2:1 isomers) 9.35 (s, 1H, isomer 1), 8.51 (s, 1H, isomer 2), 7.51~7.70 (m, 4H, both isomers), 4.45 (m, 1H, isomer 1), 4.40 (m, 1H, isomer 2), 2.08 (m, 1H, both isomers), 1.72 (m, 1H, both isomers), 1.58 (s, 3H, isomer 1), 1.45 (s, 3H, isomer 2), 0.15 (s, 9H, isomer 1), 0.05 (s, 9H, isomer 2).

Example 94

3-Methyl-3,4-dihydro-2H-pyrazole-3-carboxylic acid 3-phenoxy-benzylamide and

3-Methyl-5-trimethylsilanyl-4,5-dihydro-3H-pyrazole-3-carboxylic acid 3-phenoxy-benzylamide Compound #22 and Compound #66

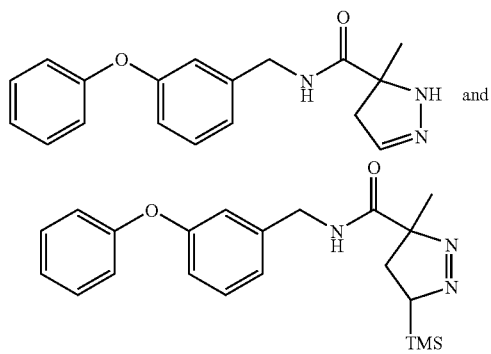

Following the procedure described in Example 31, the title compounds were obtained as white solids.

3-Methyl-3,4-dihydro-2H-pyrazole-3-carboxylic acid 3-phenoxy-benzylamide $^1$H NMR (CDCl$_3$) δ 7.55 (s, br, 1H), 7.32 (m, 2H), 7.25 (m, 2H), 7.12 (t, J=7.8 Hz, 1H), 6.98 (m, 4H), 6.72 (s, 1H), 5.25 (s, br, 1H), 4.40 (d, J=5.2 Hz, 2H), 2.88 (abq, J=12.5 Hz, 2H), 1.48 (s, 3H).
MS (m/z): MH+ (310), MNa+ (332), MH− (308)

3-Methyl-5-trimethylsilanyl-4,5-dihydro-3H-pyrazole-3-carboxylic acid 3-phenoxy-benzylamide $^1$H NMR (CDCl$_3$) 6 (1:1 isomers) 6.85~7.36 (m, 9H, both isomers), 6.75 (s, 1H, isomer 1), 6.51 (s, 1H, isomer 2), 4.51 (m, 2H, both isomers), 4.40 (m, 1H, isomer 1), 4.35 (m, 1H, isomer 2), 2.32 (m, 1H, isomer 1), 2.00 (m, 1H, isomer 2), 1.65 (m, 1H, isomer 1), 1.58 (s, 3H, isomer 1), 1.50 (s, 3H, isomer 2), 1.32 (m, 1H, isomer 2), 0.15 (s, 9H, isomer 1), 0.05 (s, 9H, isomer 2).

Example 95

3-Methyl-3,4-dihydro-2H-pyrazole-3-carboxylic acid 3-methanesulfonyl-benzylamide and 3-Methyl-5-trimethylsilanyl-4,5-dihydro-3H-pyrazole-3-carboxylic acid 3-methanesulfonyl-benzylamide Compound #26 and Compound #67

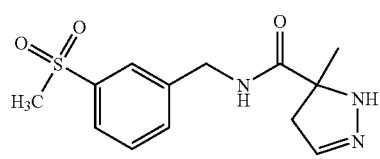

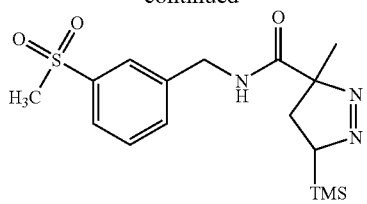

Following the procedure described in Example 31, the title compounds were obtained as white solids.

3-Methyl-3,4-dihydro-2H-pyrazole-3-carboxylic acid 3-methanesulfonyl-benzylamide $^1$H NMR (CDCl$_3$) δ 7.90 (d, J=7.5 Hz, 2H), 7.72 (br, s, 1H), 7.42 (d, J=7.5 Hz, 2H), 6.78 (s, 1H), 5.28 (s, 1H), 4.50 (d, J=4.8 Hz, 2H), 3.15 (s, 3H), 2.98 (abq, J=12.5 Hz, 2H), 1.48 (s, 3H).
MS (m/z): MH+ (296), MNa+ (318), MH− (294) 3-Methyl-5-trimethylsilanyl-4,5-dihydro-3H-pyrazole-3-carboxylic acid 3-methanesulfonyl-benzylamide:
$^1$H NMR (CDCl$_3$) 6 (1:1 isomers) 7.82 (m, 2H, both isomers), 7.40 (m, 2H, both isomers), 7.15 (s, 1H, isomer 1), 6.90 (s, 1H, isomer 2), 4.51 (m, 2H, both isomers), 4.40 (m, 1H, isomer 1), 4.32 (m, 1H, isomer 2), 2.32 (m, 1H, isomer 1), 1.92 (m, 1H, isomer 2), 1.62 (m, 1H, isomer 1), 1.58 (s, 3H, isomer 1), 1.50 (s, 3H, isomer 2), 1.28 (m, 1H, isomer 2), 0.15 (s, 9H, isomer 1), 0.05 (s, 9H, isomer 2).

Example 96

(R)-3-Methyl-5-trifluoromethyl-3,4-dihydro-2H-pyrazole-3-carboxylic acid (4-cyano-3-trifluoromethyl-phenyl)-amide and (S)-3-Methyl-5-trifluoromethyl-3,4-dihydro-2H-pyrazole-3-carboxylic acid (4-cyano-3-trifluoromethyl-phenyl)-amide Compound #35 and Compound #36

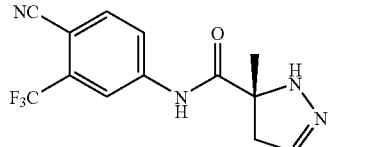

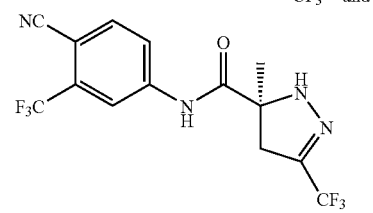

A racemic mixture of 3-methyl-5-trifluoromethyl-3,4-dihydro-2H-pyrazole-3-carboxylic acid (4-cyano-3-trifluoromethyl-phenyl)-amide (500 mg) was loaded onto a ChiralPak AD chiral HPLC column (50 mm I.D.×500 mm L) and eluted with 10% ethanol in heptane at the 70 mL/min flow rate. Two peaks were collected separately and were removed under vacuum to yield:

(R)-3-Methyl-5-trifluoromethyl-3,4-dihydro-2H-pyrazole-3-carboxylic acid (4-cyano-3-trifluoromethyl-phenyl)-amide as peak two.

MS (CI) m/z 365(M+H+)

and (S)-3-Methyl-5-trifluoromethyl-3,4-dihydro-2H-pyrazole-3-carboxylic acid (4-cyano-3-trifluoromethyl-phenyl)-amide as peak one.

MS (CI) m/z 365(M+H+)

Example 97

(R)-3-Ethyl-5-trifluoromethyl-3,4-dihydro-2H-pyrazole-3-carboxylic acid (4-cyano-3-trifluoromethyl-phenyl)-amide and (S)-3-Ethyl-5-trifluoromethyl-3,4-dihydro-2H-pyrazole-3-carboxylic acid (4-cyano-3-trifluoromethyl-phenyl)-amide Compound #81 and Compound #82

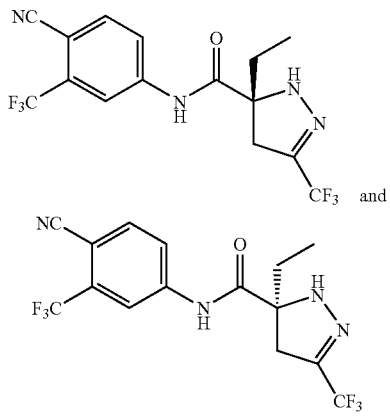

The racemic mixture of 3-ethyl-5-trifluoromethyl-3,4-dihydro-2H-pyrazole-3-carboxylic acid (4-cyano-3-trifluoromethyl-phenyl)-amide (500 mg) was loaded onto a ChiralPak AD chiral HPLC column (50 mm I.D.×500 mm L) and eluted with 10% ethanol in heptane at the 70 mL/min flow rate. Two peaks were collected separately and were removed under vacuum to yield:

(R)-3-ethyl-5-trifluoromethyl-3,4-dihydro-2H-pyrazole-3-carboxylic acid (4-cyano-3-trifluoromethyl-phenyl)-amide as peak two.

MS (CI) m/z 379(M+H+)

and (S)-3-ethyl-5-trifluoromethyl-3,4-dihydro-2H-pyrazole-3-carboxylic acid (4-cyano-3-trifluoromethyl-phenyl)-amide as peak one.

MS (CI) m/z 379(M+H+)

Example 98

3-Methyl-pyrazolidine-3-carboxylic acid (4-cyano-3-trifluoromethyl-phenyl)-amide Compound #100

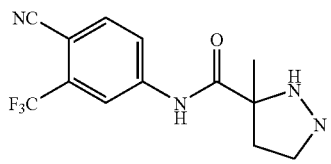

3-Methyl-3,4-dihydro-2H-pyrazole-3-carboxylic acid (4-cyano-3-trifluoromethyl-phenyl)-amide (1.5 g, 5.1 mmoL) in glacial acetic acid (5 mL) was treated with powder NaCNBH₃ (750 mg, 12.7 mmoL) at room temperature. The reaction mixture was stirred for 1 hr. The reaction mixture was then neutralized with saturated NaHCO₃ and extracted with ethyl acetate (3×). The combined organic layer was washed with water and brine, dried over Na₂SO₄, filtered and concentrated to yield the title compound as a colorless oil.

¹H NMR (CDCl₃) δ 9.89 (s, br, 1H), 8.11 (s, 1H), 8.02 (d, J=7.5 Hz, 1H), 7.77 (d, J=7.5 Hz, 1H), 3.28 (t, J=8.5 Hz, 2H), 2.65 m, 2H), 1.61 (s, 3H).

MS (CI) m/z MH+ (299), MH− (297).

Example 99

3-Methyl-1-(2,2,2-trifluoro-acetyl)-pyrazolidine-3-carboxylic acid (4-cyano-3-trifluoromethyl-phenyl)-amide Compound #101

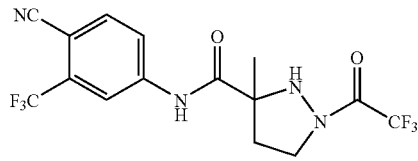

3-Methyl-pyrazolidine-3-carboxylic acid (4-cyano-3-trifluoromethyl-phenyl)-amide (350 mg, 0.84 mmoL) in DCM (2 mL) was treated with Et₃N (118 μL, 0.84 mmoL) and TFAA (117 μL, 0.84 mmoL) at 0° C. The reaction mixture was stirred for 30 min and then partitioned between saturated NaHCO₃ and DCM. The organic layer was washed with water and brine, dried over Na₂SO₄, filtered and concentrated to yield the title compound as a colorless oil, which was then purified by silica gel column using hexanes:ethyl acetate 1:1 as eluent to yield the title compound as a white solid.

¹H NMR (CDCl₃) δ 9.22 (s, br, 1H), 8.08 (s, 1H), 7.82 (s, 2H), 3.72 (m, 2H), 3.10 (m, 1H0, 2.05 (m, 1H), 1.65 (s, 3H).

MS (CI) m/z MNa+ (417), MH− (393).

Example 100

1-(4-Acetylamino-benzyl)-3-methyl-pyrazolidine-3-carboxylic acid (4-cyano-3-trifluoromethyl-phenyl)-amide Compound #102

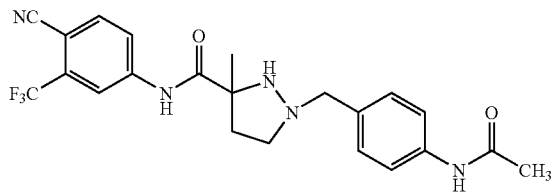

3-Methyl-pyrazolidine-3-carboxylic acid (4-cyano-3-trifluoromethyl-phenyl)-amide (410 mg, 1.38 mmoL) and (225 mg, 1.38 mmoL) in MeOH (5 mL) at room temperature was treated with NaCNBH$_3$ (216 mg, 3.44 mmoL). The reaction mixture was stirred at room temperature overnight. The solvent was removed and the residue was partitioned between ethyl acetate and water. The aqueous layer was extracted with ethyl acetate (3×). The combined organic layer was washed with water and brine, dried over Na$_2$SO$_4$, filtered and concentrated to yield the title compound as a colorless oil, which was then purified by silica gel column using hexanes:ethyl acetate 1:1 as eluent to yield the title compound as a white solid.

$^1$H NMR (CDCl$_3$) δ 8.05 (s, 1H), 7.85 (d, J=6.5 Hz, 1H), 7.62 (d, J=6.5 Hz, 1H), 7.52 (d, J=7.0 Hz, 2H), 7.25 (d, J=7.0 Hz, 2H), 3.75 (abq, J=12.5 Hz, 2H), 3.18 (m, 1H), 2.65 (m, 3H), 2.15 (s, 3H), 1.48 (s, 3H).

MS (m/z): MNa+ (468)

Example 101

2-Methyl-N-pyridin-4-yl-acrylamide

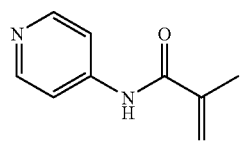

LiHMDS (1.0 N in THF, 23.6 mmoL, 24 mL) was added dropwise into pyridine (11.8 mmoL, 1.11 g) in THF (10 mL) at 0° C. After 10 min, 2-methyl-acryloyl chloride (11.8 mmoL, 1.43 mL) was added into the reaction at 0° C. The reaction was then slowly warmed to room temperature. The solvent was removed and the residue was partitioned between Et$_2$O and water. The Et$_2$O layer was washed with brine, dried over anhydrous Na$_2$SO$_4$, filtered and concentrated to yield a brown oil. The crude material (the brown oil) was then purified by column chromatography (silica gel, EtOAc as eluent) to yield the title compound as a reddish oil.

$^1$H NMR (CDCl$_3$) δ 8.45 (br, s, 1H), 8.22 (d, J=7.5 Hz, 2H), 7.45 (d, J=7.5 Hz, 2H), 5.68 (s, 1H), 5.26 (s, 1H), 1.89 (s, 3H).

Example 102

N-(6-Chloro-pyridin-3-yl)-2-methyl-acrylamide

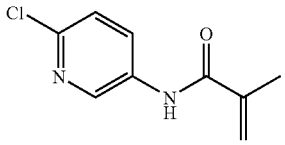

Following the procedure described in Example 1, the title compound was obtained as a grey solid.

$^1$H NMR (CDCl$_3$) δ 8.45 (s, 1H), 8.20 (d, J=7.5 Hz, 1H), 7.61 (s, br, 1H), 7.34 (d, J=7.5 Hz, 1H), 5.88 (s, 1H), 5.55 (s, 1H), 2.05 (s, 3H).

Example 103

N-(6-Cyano-pyridin-3-yl)-2-methyl-acrylamide

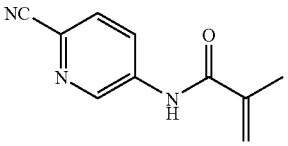

Following the procedure described in Example 1, the title compound was obtained as a grey solid.

$^1$H NMR (CDCl$_3$) δ 8.65 (s, 1H), 8.48 (d, J=8.5 Hz, 1H), 7.88 (s, br, 1H), 7.70 (d, J=8.5 Hz, 1H), 5.88 (s, 1H), 5.62 (s, 1H), 2.12 (s, 3H).

MS (m/z): MH+ (188).

Example 104

5-(4-Fluoro-phenyl)-3-methyl-3,4-dihydro-2H-pyrazole-3-carboxylic acid pyridin-4-ylamide Compound #93

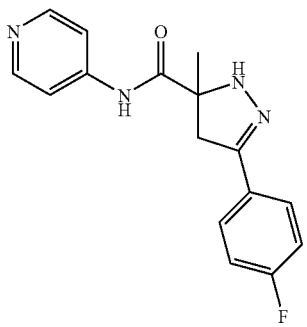

Following the procedure described in Example 29, the title compound was obtained as a pale solid.

$^1$H NMR (CDCl$_3$) δ 9.45 (br, s, 1H), 8.35 (d, J=7.5 Hz, 2H), 7.38 (d, J=7.5 Hz, 2H), 7.15 (d, J=6.5 Hz, 2H), 7.04 (d, J=6.5 Hz, 2H), 3.36~3.22 (Abq, J=12.5 Hz, 2H), 1.62 (s, 3H).

MS (m/z): MH+ (299)

Example 105

3-Methyl-3,4-dihydro-2H-pyrazole-3-carboxylic acid (6-chloro-pyridin-3-yl)-amide Compound #80

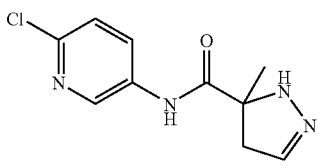

Following the procedure described in Example 31, the title compound was obtained as a white solid in pure form.

$^1$H NMR (CDCl$_3$) δ 9.05 (s, br, 1H), 8.25 (s, 1H), 7.95 (d, J=7.5 Hz, 1H), 7.10 (d, J=7.5 Hz, 1H), 7.05 (s, 1H), 5.55 (s, br, 1H), 2.72 (abq, J=12.5 Hz, 2H), 1.25 (s, 3H).

MS (m/z): MH+ (239)

Example 106

3-Methyl-5-trifluoromethyl-3,4-dihydro-2H-pyrazole-3-carboxylic acid (6-chloro-pyridin-3-yl)-amide Compound #88

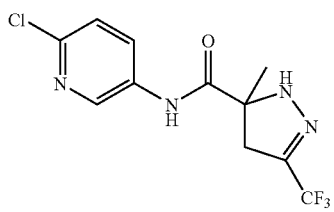

Following the procedure described in Example 29, the title compound was obtained as a white solid.

$^1$H NMR (CDCl$_3$) δ 8.90 (s, 1H), 8.55 (m, 1H), 8.15 (m, 1H), 7.30 (m, 1H), 6.10 (s, 1H), 3.15 (dd, J=6.0, 2.7 Hz, 2H), 1.60 (s, 3H).

MS (m/z): MH+ (307).

Example 107

3-Methyl-5-trifluoromethyl-3,4-dihydro-2H-pyrazole-3-carboxylic acid (6-cyano-pyridin-3-yl)-amide Compound #88

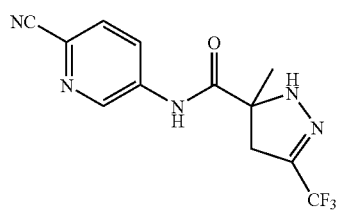

Following the procedure described in Example 29, the title compound was obtained as a white solid.

$^1$H NMR (CDCl$_3$) δ 9.21 (s, br, 1H), 8.75 (s, 1H), 8.38 (d, J=7.5 Hz, 1H), 7.70 (d, J=7.5 Hz, 1H), 6.05 (s, 1H), 3.20 (abq, J=11.5 Hz, 2H), 1.62 (s, 3H).

MS (m/z): MNa+ (320).

Example 108

3-(4-Acetylamino-phenyl)-2,5-dimethyl-isoxazolidine-5-carboxylic acid (4-cyano-3-trifluoromethyl-phenyl)-amide

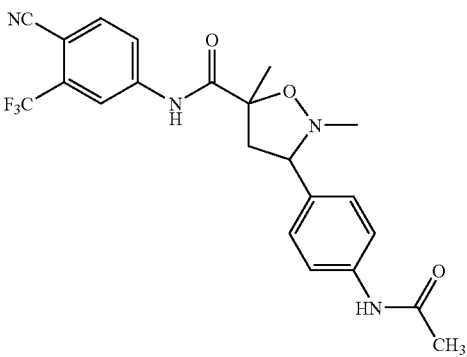

2-Methyl-N-(4-cyano-3-trifluoromethyl-phenyl)-acrylamide (193 mg, 0.76 mmoL) in xylene (5 mL) was treated with N-methyl-{4-(oxyimino-methyl)phenyl}acetamide (250 mg, 0.76 mmoL) (which may be prepared by known methods). The reaction mixture was then heated to 50° C. and stirred for 6 hrs. The solvent was removed and the residue was purified by silica gel column using 1:1 hexanes:ethyl acetate as eluent to yield the title compound as a white solid.

$^1$H NMR (CDCl$_3$) δ 9.42 (s, 1H), 8.12 (s, 1H), 7.98 (d, J=7.3 Hz, 1H), 7.81 (d, J=7.3 Hz, 1H), 7.55 (s, 1H), 7.49 (d, J=8.0 Hz, 2H), 7.22 (d, J=8.0 Hz, 2H), 3.62 (t, J=6.4 Hz, 1H), 2.75 (m, 1H), 2.68 (s, 3H), 2.61 (m, 1H), 2.18 (s, 3H), 1.62 (s, 3H).

MS (m/z): MH+ (447), MNa+ (469), MH− (445).

Example 109

3-(4-Acetylamino-phenyl)-2,5-dimethyl-isoxazolidine-5-carboxylic acid (4-nitro-3-trifluoromethyl-phenyl)-amide Compound #70

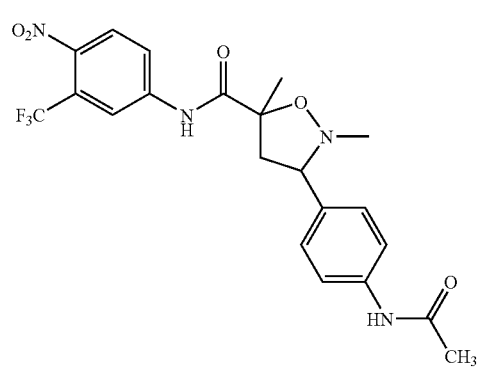

Following the procedure described in Example 108, the title compound was obtained as a white solid.

$^1$H NMR (CDCl$_3$) δ 9.45 (s, br, 1H), 8.12 (s, 1H), 8.01 (m, 2H), 7.45 (d, J=7.8 Hz, 2H), 7.38 (s, 1H), 7.18 (d, J=7.8 Hz, 2H), 3.61 (t, J=6.5 Hz, 1H), 2.81 (m, 1H), 2.68 (s, 3H), 2.61 (m, 1H), 2.18 (s, 3H), 1.62 (s, 3H).

MS (m/z): MH+ (467), MNa+ (489)

Example 110

2-Methyl-oxirane-2-carboxylic acid (4-cyano-3-trifluoromethyl-phenyl)-amide

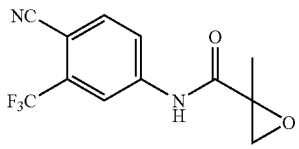

2-Methyl-N-(4-cyano-3-trifluoromethyl-phenyl)-acrylamide (1.35 g, 5.0 mmol) in $CH_2Cl_2$ (15 ml) was treated by TFA (3.0 ml) at 0° C. To the reaction mixture was then added $H_2O_2$ (30%, 1.0 ml, 10.0 mmol) dropwise. The reaction mixture was stirred overnight and quenched by $NaHCO_3$, then extracted by ethyl acetate. The organic layers were combined and dried over $Na_2SO_4$, concentrated and purified by silica gel column using hexanes:ethyl acetate 4:1 as eluent to yield the title compound as a white solid.

$^1$H NMR ($CDCl_3$) δ 8.40 (br. 1H), 8.10-7.80 (m, 3H), 5.85 (s, 1H), 5.60 (s, 1H), 2.00 (s, 3H).

MS (m/z): MNa+ (293).

Example 111

3-Amino-N-(4-cyano-3-trifluoromethyl-phenyl)-2-hydroxy-2-methyl-propionamide

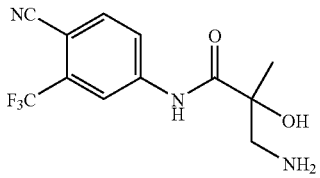

2-Methyl-oxirane-2-carboxylic acid (4-cyano-3-trifluoromethyl-phenyl)-amide (1.0 g, 3.48 mmoL) was dissolved in 7N $NH_3$/MeOH solution (10 mL) at room temperature. The reaction mixture was stirred overnight and the solvent was removed to yield the title compound as pale yellow solid.

$^1$H NMR ($CDCl_3$) δ 9.58 (s, br, 1H), 8.15 (s, 1H), 7.95 (d, J=7.8 Hz, 1H), 7.72 (d, J=7.8 Hz, 1H), 3.42 (d, J=9.8 Hz, 1H), 2.65 (d, J=9.8 Hz, 1H), 1.48 (s, 3H)

MS (m/z): MH+ (288)

Example 112

2,5-Dimethyl-4,5-dihydro-oxazole-5-carboxylic acid (4-cyano-3-trifluoromethyl-phenyl)-amide

Compound #103

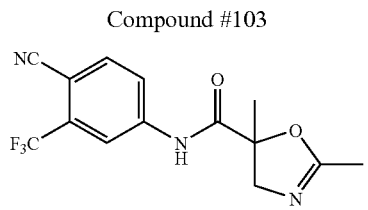

$BF_3$.Etherate (1.0 mmol) was added to a mixture of 2-methyl-oxirane-2carboxylic acid (4-cyano-3-trifluoromethyl-phenyl)-amide (135 mg, 0.5 mmol) in acetonitrile (2 mL) at 0° C. The reaction mixture was stirred at 0° C. for 1 h and then quenched with $NaHCO_3$, the organic layer was extracted with ethyl acetate, washed with brine and concentrated to yield a crude product. The crude product was purified on silica gel with ethyl acetate to yield the title compound as a solid.

$^1$H NMR ($CDCl_3$) δ 8.50 (s, 1H), 8.10 (s, 1H), 8.00 (d, J=9.0 Hz, 1H), 7.80 (d, J=9.0 Hz), 1H), 4.00 (dd, J=105Ha, 15Ha, 2H), 2.10 (s, 3H), 1.70 (s, 3H)

MS (m/z): MH+ (312), MNa+ (334).

Example 113

2-(4-Acetylamino-phenyl)-5-methyl-oxazolidine-5-carboxylic acid (4-cyano-3-trifluoromethyl-phenyl)-amide

Compound #72

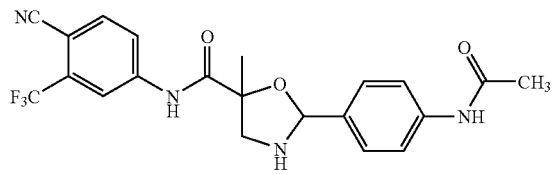

2-Methyl-oxirane-2-carboxylic acid (4-cyano-3-trifluoromethyl-phenyl)-amide (100 mg, 0.35 mmoL) and acetic acid 4-formyl-phenyl ester (57 mg, 0.35 mmoL) in MeOH (5 mL) was stirred at room temperature for 2 hr. Then, a catalytic amount of pTSA (~10 mg) was added and the reaction mixture was stirred overnight. The solvent was removed and the residue was purified by silica gel column using hexanes:ethyl acetate 2:1 as eluent to yield the title compound as a white solid.

$^1$H NMR ($CDCl_3$) δ 9.60 (s, br, 1H), 8.31 (s, br, 1H), 8.08 (s, 1H), 7.92 (d, J=6.8 Hz, 1H), 7.70 (d, J=7.5 Hz, 2H), 7.58 (d, J=7.5 Hz, 2H), 4.42 (br, s, 1H), 4.02 (abq, J=12.5 Hz, 2H), 2.18 (s, 3H), 1.55 (s, 3H).

MS (m/z): MH+ (433)

Example 114

2,5-Dimethyl-4,5-dihydro-oxazole-5-carboxylic acid (3,4-dichloro-phenyl)-amide

Compound #104

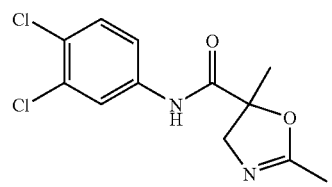

Following the procedure described in Example 112, the title compound was obtained as a white solid.

$^1$H NMR ($CDCl_3$) δ 7.80 (s, 1H), 7.45 (d, J=9.0 Hz, 1H), 6.80 (d, J=9.0 Hz, 1H), 3.60 (dd, J=30.0 Hz, 18.0 Hz, 2H), 1.50 (s, 3H), 1.20 (s, 3H).

MS (m/z): MH+ (332), MNa+ (354)

Example 115

2,5-Dimethyl-4,5-dihydro-oxazole-5-carboxylic acid (4-cyano-phenyl)-amide

Compound #105

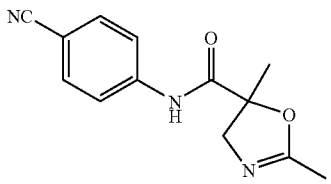

Following the procedure described in Example 112, the title compound was obtained as a white solid.

$^1$H NMR (CDCl$_3$) δ 8.15 (s, 1H), 7.80 (dd, J=52.0 Hz, 9.0 Hz, 4H), 3.50 (dd, J=60.0 Hz, 21.0 Hz, 2H), 1.90 (s, 3H), 1.40 (s, 3H)

MS (m/z): M+H$_2$O (262)

Example 116

4-acetamido-N-(ethyl)-benzenecarbohydrazonoyl chloride

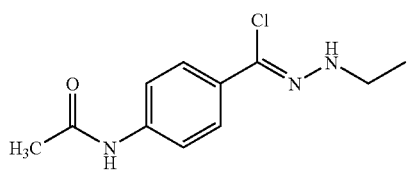

Following the procedure described in Example 21, starting from N-[4-(ethyl-hydrazonomethyl)-phenyl]-acetamide, the title compound was prepared as a white solid.

MS (m/z): MH+ (240).

Example 117

5-(4-Acetylamino-phenyl)-2-ethyl-3-methyl-3,4-dihydro-2H-pyrazole-3-carboxylic acid (4-cyano-3-trifluoromethyl-phenyl)-amide Compound #135

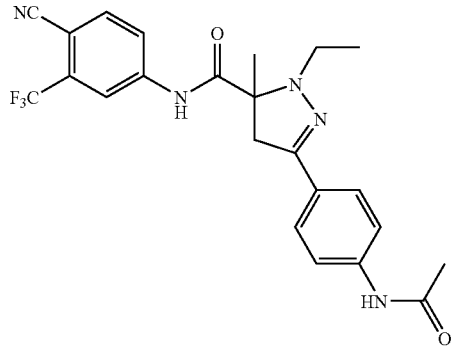

Following the procedure described in Example 23, starting from 4-acetamido-N-(ethyl)-benzenecarbohydrazonoyl chloride, the title compound was prepared as an off-white solid.

MS (m/z): MH+ (458).

Example 118

2-Ethyl-3,5-dimethyl-3,4-dihydro-2H-pyrazole-3-carboxylic acid (4-cyano-3-trifluoromethyl-phenyl)-amide Compound #146

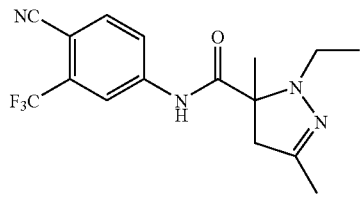

3,5-Dimethyl-3,4-dihydro-2H-pyrazole-3-carboxylic acid (4-cyano-3-trifluoromethyl-phenyl)-amide (1 mmoL) was reacted with a diazoethane/diethyl ether solution (10 mmoL) in dioxane for about 5 days. The reaction mixture was worked up by solvent evaporation and column chromatography separation. The title compound was isolated as a minor product, as a white solid.

$^1$H NMR (CDCl$_3$) δ 9.68 (s, 1H), 8.07 (s, 1H), 7.85 (d, J=8.0 Hz, 1H), 7.75 (d, J=8.0 Hz, 1H), 3.15 (m, 1H), 3.05 (abq, J=10.0 Hz, 1H), 2.80 (m, 1H), 2.71 (abq, J=10.0 Hz, 1H), 1.98 (s, 3H), 1.40 (s, 3H), 1.35 (t, J=9.5 hz, 3H)

MS (m/z): MH+ 339.

Example 119

N-(4-Cyano-3-trifluoromethyl-phenyl)-2-trifluoromethyl-acrylamide

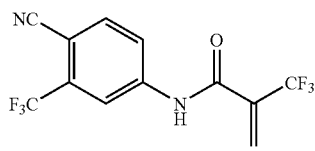

2-Trifluoromethyl-acrylic acid (36.0 mmoL) in thionyl chloride (2.86 mL) was refluxed for 30 min. Excess thionyl chloride was removed in vacuo to yield a residue. 4-Amino-2-trifluoromethyl-benzonitrile (36.0 mmoL) in diethyl ether (50 mL) was added dropwise to the residue at −40° C. The reaction mixture was slowly warmed to room temperature. The reaction mixture was then partitioned between diethyl ether and water. The diethyl ether layer was washed with saturated sodium bicarbonate, then brine, dried over anhydrous Na$_2$SO$_4$, filtered and concentrated to yield a brown oil. The crude material (the brown oil) was then purified by column chromatography (silica gel, using ethyl acetate as eluent) to yield the title compound as yellow solid.

$^1$H NMR (CDCl$_3$) δ 8.25 (br, s, 1H), 7.60 (d, J=8.0 Hz, 1H), 6.95 (s, 1H), 6.75 (d, J=8.0 Hz, 1H), 6.25 (s, 1H), 5.98 (s, 1H).

Example 120

3,5-Bis-trifluoromethyl-3,4-dihydro-2H-pyrazole-3-carboxylic acid (4-cyano-3-trifluoromethyl-phenyl)-amide Compound #112

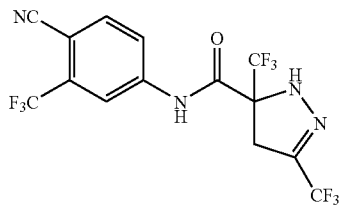

Following the procedure described in Example 29, starting from N-(4-cyano-3-trifluoromethyl-phenyl)-2-trifluoromethyl-acrylamide and 4-methyl-2-[(1E)-2,2,2-trifluoroethylidene]benznenesulfonyl hydrazone, the title compound was prepared as a yellow solid.

$^1$H NMR (CDCl$_3$) δ9.18 (s, 1H), 8.11 (s, 1H), 8.05 (d, J=8.0 Hz, 1H), 7.82 (D, J=8.0 Hz, 1H), 7.05 (s, 1H), 3.62 (abq, J=9.0 Hz, 1H), 3.08 (abq, J=9.0 Hz, 1H)

MS (m/z): MH$^+$ 419.

Example 121

5-(4-Cyano-3-trifluoromethyl-phenylcarbamoyl)-5-trifluoromethyl-4,5-dihydro-1H-pyrazole-3-carboxylic acid ethyl ester Compound #113

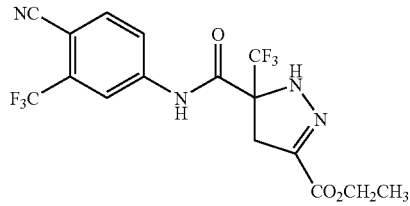

Following the procedure described in Example 31 starting from N-(4-cyano-3-trifluoromethyl-phenyl)-2-trifluoromethyl-acrylamide and ethyl diazoacetate, the title compound was prepared as a yellow solid.

$^1$H NMR (CDCl$_3$) δ 9.28 (s, 1H), 8.10 (s, 1H), 8.08 (d, J=8.0 Hz, 1H), 7.82 (d, J=7.8 Hz, 1H), 7.70 (s, 1H), 4.32 (q, J=6.8 Hz, 2H), 3.72 (abq, J=8.5 Hz, 1H), 3.60 (abq, J=8.5 Hz, 1H), 1.35 (t, J=8.5 Hz, 3H)

MS (m/z): MH$^+$ 423.

Example 122

5-Methyl-3-trifluoromethyl-4,5-dihydro-3H-pyrazole-3-carboxylic acid (4-cyano-3-trifluoromethyl-phenyl)-amide Compound #114

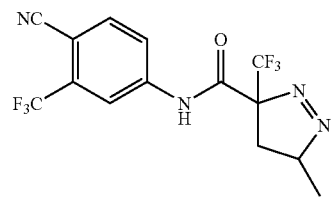

and 5-Methyl-3-trifluoromethyl-3,4-dihydro-2H-pyrazole-3-carboxylic acid (4-cyano-3-trifluoromethyl-phenyl)-amide Compound #116

Following the procedure described in Example 47, starting from N-(4-cyano-3-trifluoromethyl-phenyl)-2-trifluoromethyl-acrylamide, the title compounds were prepared as off-white solids.

5-Methyl-3-trifluoromethyl-4,5-dihydro-3H-pyrazole-3-carboxylic acid (4-cyano-3-trifluoromethyl-phenyl)-amide $^1$H NMR (CDCl$_3$) δ diastereomer 1, 9.01 (s, 1H), 8.15 (s, 1H), 8.01 (d, J=7.5 Hz, 1H), 7.80 (d, J=7.5 Hz, 1H), 4.85 (m, 1H), 3.15 (m, 1H), 2.40 (m, 1H), 1.55 (d, J=9.5 Hz, 3H); diastereomer 2, 8.55 (s, 1H), 8.05 (s, 1H), 7.90 (d, J=8.0 Hz, 1H), 7.65 (d, J=8.0 Hz, 1H), 4.70 (m, 1H), 2.75 (m, 1H), 1.80 (m, 1H), 1.65 (d, J=10.0 Hz, 3H).

5-Methyl-3-trifluoromethyl-3,4-dihydro-2H-pyrazole-3-carboxylic acid (4-cyano-3-trifluoromethyl-phenyl)-amide $^1$H NMR (CDCl$_3$) δ 9.75 (br, s, 1H), 8.15 (s, 1H), 7.98 (d, J=6.5 Hz, 1H), 7.80 (d, J=7.5 Hz, 1H), 6.25 (s, 1H), 3.45 (abq, J=8.5 Hz, 1H), 3.25 (abq, J=8.5 Hz, 1H), 2.12 (s, 3H)

MS (m/z): MH$^+$ 365.

Example 123

N-(4-Cyano-3-trifluoromethyl-phenyl)-2,2,2-trifluoro-N-(2-methyl-acryloyl)-acetamide

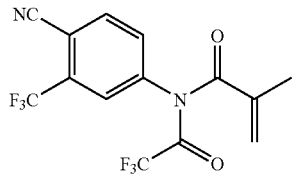

N-(4-Cyano-3-trifluoromethyl-phenyl)-2-methyl-acrylamide (4.4 mmoL) in DCM (15 mL) was reacted with pyridine (6 mL) followed by trifluoroacetic anhydride (4.4 mmoL) at 0° C. The reaction mixture was slowly warmed to room temperature. The reaction mixture was partitioned between DCM and water. The DCM layer was washed with saturated sodium bicarbonate, then brine, dried over anhydrous Na$_2$SO$_4$, filtered and concentrated to yield a yellow oil. The crude material (the yellow oil) was purified by column chromatography (silica gel, using ethyl acetate as eluent) to yield the title compound as a yellow solid.

$^1$H NMR (CDCl$_3$) δ8.15 (s, 1H), 8.05 (d, J=8.5 Hz, 1H), 7.85 (d, J=8.5 Hz, 1H), 6.25 (s, 1H), 5.81 (s, 1H), 5.65 (s, 1H), 2.05 (s, 3H). MS (m/z): MH$^+$ 351.

Example 124

3-Methyl-5-trifluoromethyl-3,4-dihydro-2H-pyrazole-3-carboxylic acid (4-cyano-3-trifluoromethyl-phenyl)-(2,2,2-trifluoro-acetyl)-amide Compound #115

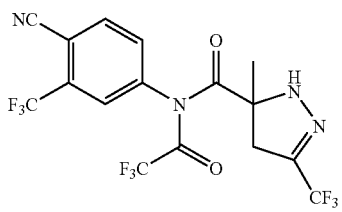

Following the procedure described in Example 29, starting from N-(4-cyano-3-trifluoromethyl-phenyl)-2,2,2-trifluoro-N-(2-methyl-acryloyl)-acetamide and 4-methyl-2-[(1E)-2,2,2-trifluoroethylidene]benznenesulfonyl hydrazone, the title compound was prepared as a yellow solid.

$^1$H NMR (CDCl$_3$) δ8.10 (s, 1H), 7.95 (d, J=7.5 Hz, 1H), 7.60 (d, J=7.5 Hz, 1H), 3.75 (d, J=10.5 Hz, 1H), 3.21 (d, J=10.5 Hz, 1H), 1.85 (s, 3H)

MS (m/z): MNa+ 483

Example 125

3-Methyl-5-trifluoromethyl-3,4-dihydro-2H-pyrazole-3-carboxylic acid (4-bromo-3-trifluoromethyl-phenyl)-amide Compound #119

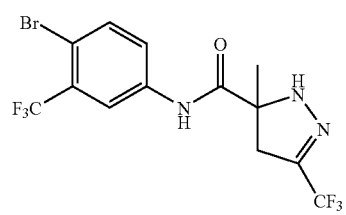

Following the procedure described in Example 29, starting from N-(4-bromo-3-trifluoromethyl-phenyl)-2-methyl-acrylamide and 4-methyl-2-[(1E)-2,2,2-trifluoroethylidene]benznenesulfonyl hydrazone, the title compound was prepared as a yellow solid.

$^1$H NMR (CDCl$_3$) δ 8.95 (s, 1H), 7.96 (s, 1H), 7.65 (s, 2H), 5.86 (s, 1H), 3.28 (abq, J=9.8 Hz, 1H), 3.10 (abq, J=9.8 Hz, 1H), 1.60 (s, 3H)

MS (m/z): MH$^+$ 419.

Example 126

2-Ethyl-3-methyl-5-trifluoromethyl-3,4-dihydro-2H-pyrazole-3-carboxylic acid (4-cyano-3-trifluoromethyl-phenyl)-amide Compound #120

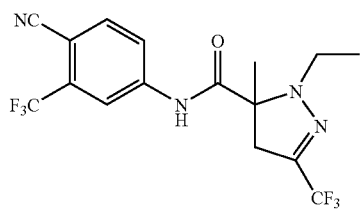

and N-(4-Cyano-3-trifluoromethyl-phenyl)-3-methyl-5-trifluoromethyl-4,5-dihydro-3H-pyrazole-3-carboximidic acid ethyl ester Compound #200

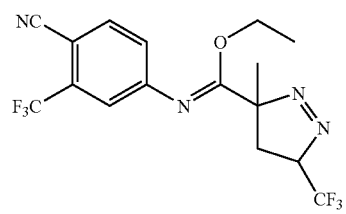

3-Methyl-5-trifluoromethyl-3,4-dihydro-2H-pyrazole-3-carboxylic acid (4-cyano-3-trifluoromethyl-phenyl)-amide (400 mg, 1.1 mmol) and Na$_2$HPO$_4$ (1.0 g, 7 mmol) in CH$_2$Cl$_2$ (10 ml) was treated with BF$_4$.O(CH$_2$CH$_3$)$_3$ (1M in CH$_2$Cl$_2$, 5.0 ml) at 0° C. The reaction mixture was warmed to room temperature, stirred overnight and then quenched with NaHCO$_3$. CH$_2$Cl$_2$ was added to extract the product and the organic layer was then washed with brine and dried over Na$_2$SO$_4$. Upon the purification on silica gel (CH$_2$Cl$_2$:ethyl acetate: 10:1), the title compounds were obtained as white solids.

2-Ethyl-3-methyl-5-trifluoromethyl-3,4-dihydro-2H-pyrazole-3-carboxylic acid (4-cyano-3-trifluoromethyl-phenyl)-amide $^1$H NMR (CDCl$_3$) δ 9.10 (br, 1H), 8.10 (s, 1H), 7.95 (m, 1H), 7.80 (m, 1H), 3.40-3.00 (m, 4H), 1.50 (s, 3H), 1.35 (m, 3H)
MS (m/z): MH$^+$ 393

N-(4-Cyano-3-trifluoromethyl-phenyl)-3-methyl-5-trifluoromethyl-4,5-dihydro-3H-pyrazole-3-carboximidic acid ethyl ester $^1$H NMR (CDCl$_3$) δ 7.85 (m, 1H), 7.65 (s, 1H), 7.50 (s, 1H), 5.30 (m, 1H), 4.40 (m, 1H), 3.90 (m, 1H), 2.95 (m, 1H), 2.40 (m, 1H), 1.55 (m, 3H), 1.50 (s, 3H)
MS (m/z): MH$^+$ 393

Example 127

2-Ethyl-3(R)-methyl-5-trifluoromethyl-3,4-dihydro-2H-pyrazole-3-carboxylic acid (4-cyano-3-trifluoromethyl-phenyl)-amide Compound #125

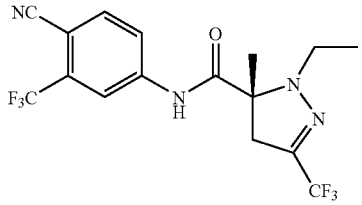

and N-(4-Cyano-3-trifluoromethyl-phenyl)-3(R)-methyl-5-trifluoromethyl-4,5-dihydro-3H-pyrazole-3-carboximidic acid ethyl ester Compound #202

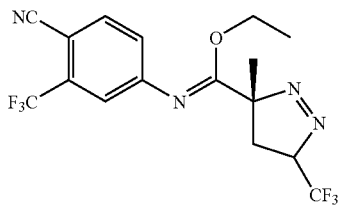

Following the procedure described in Example 126, starting from 3(R)-methyl-5-trifluoromethyl-3,4-dihydro-2H-pyrazole-3-carboxylic acid (4-cyano-3-trifluoromethyl-phenyl)-amide, the title compounds were prepared as off-white solids.

NMR and MS data of the title compounds were the same as described in Example 126.

Example 128

2-Ethyl-3(S)-methyl-5-trifluoromethyl-3,4-dihydro-2H-pyrazole-3-carboxylic acid (4-cyano-3-trifluoromethyl-phenyl)-amide Compound #122

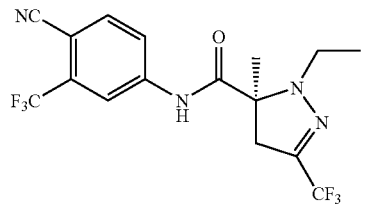

and N-(4-Cyano-3-trifluoromethyl-phenyl)-3(S)-methyl-5-trifluoromethyl-4,5-dihydro-3H-pyrazole-3-carboximidic acid ethyl ester Compound #201

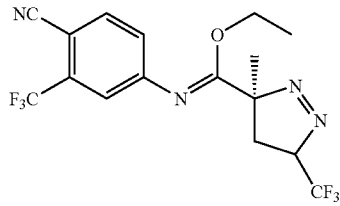

Following the procedure described in Example 126, starting from 3(S)-methyl-5-trifluoromethyl-3,4-dihydro-2H-pyrazole-3-carboxylic acid (4-cyano-3-trifluoromethyl-phenyl)-amide, the title compounds were prepared as off-white solids.

NMR and MS data of the title compounds were the same as described in Example 126.

Example 129

2,3-Dimethyl-5-trifluoromethyl-3,4-dihydro-2H-pyrazole-3-carboxylic acid (4-cyano-3-trifluoromethyl-phenyl)-amide Compound #123

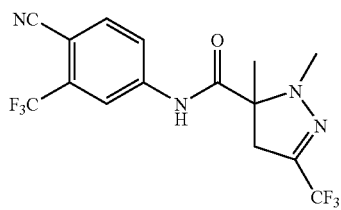

and N-(4-Cyano-3-trifluoromethyl-phenyl)-2,3-dimethyl-5-trifluoromethyl-3,4-dihydro-2H-pyrazole-3-carboximidic acid methyl ester Compound #203

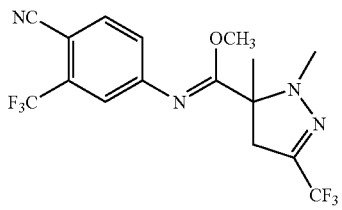

3-methyl-5-trifluoromethyl-3,4-dihydro-2H-pyrazole-3-carboxylic acid (4-cyano-3-trifluoromethyl-phenyl)-amide (2.5 mmoL) in DCM (25 mL) at 0° C. was treated with diethylpropyl amine (10 mmoL) followed by methyl triflate (2.5 mmoL). The reaction mixture was gradually warmed to room temperature and then stirred overnight. The reaction mixture was partitioned between DCM and water. The DCM layer was washed with saturated sodium bicarbonate, brine, then dried over anhydrous $Na_2SO_4$, filtered and concentrated to yield a yellow oil, which was then purified by column chromatography (silica gel, using ethyl acetate as eluent) to yield the title compounds as off-white solids.

2,3-Dimethyl-5-trifluoromethyl-3,4-dihydro-2H-pyrazole-3-carboxylic acid (4-cyano-3-trifluoromethyl-phenyl)-amide $^1$H NMR (CDCl$_3$) δ 9.02 (s, 1H), 8.11 (s, 1H), 7.98 (d, J=7.5 Hz, 1H), 7.82 (d, J=7.5 Hz, 1H), 3.32 (abq, J=9.5 Hz, 1H), 3.02 (abq, J=9.5 Hz, 1H), 3.01 (s, 3H), 1.52 (s, 3H) MS (m/z): MH$^+$ 379.

N-(4-Cyano-3-trifluoromethyl-phenyl)-2,3-dimethyl-5-trifluoromethyl-3,4-dihydro-2H-pyrazole-3-carboximidic acid methyl ester $^1$H NMR (CDCl$_3$) δ 8.21 (s, 1H), 8.05 (d, J=8.0 Hz, 1H), 7.90 (d, J=8.0 Hz, 1H), 4.36 (s, 3H), 3.52 (s, 3H), 3.36 (d, J=12.5 Hz, 1H), 3.10 (d, J=12.5 Hz, 1H), 1.52 (s, 3H) MS (m/z): MH$^+$ 393.

Example 130

5-Chloro-3-methyl-5-trifluoromethyl-4,5-dihydro-3H-pyrazole-3-carboxylic acid (4-cyano-3-trifluoromethyl-phenyl)-amide Compound #124

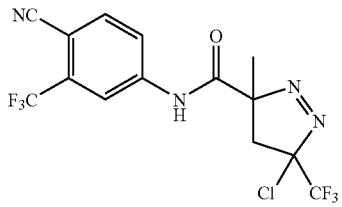

3-Methyl-5-trifluoromethyl-3,4-dihydro-2H-pyrazole-3-carboxylic acid (4-cyano-3-trifluoromethyl-phenyl)-amide (1.1 mmoL) in toluene (5 mL) was treated with PCl$_5$ (1.2 mmoL) at 100° C. for 2 hrs. The solvent was removed and the residue was purified by column chromatography using hexanes and ethyl acetate as eluent to yield the title compound as a white solid (3:2 diastereomers).

Major Diastereomer:

$^1$H NMR (CDCl$_3$) δ8.32 (s, 1H), 8.10 (s, 1H), 7.95 (d, J=7.5 Hz, 1H), 7.85 (d, J=7.5 Hz, 1H), 3.05 (abq, J=9.8 Hz, 1H), 2.25 (abq, J=9.8 Hz, 1H), 1.90 (s, 3H).

Minor Diastereomer $^1$H NMR (CDCl$_3$) δ 8.62 (s, 1H), 8.11 (s, 1H), 7.96 (d, J=7.5 Hz, 1H), 7.87 (d, J=7.5 Hz, 1H), 2.90 (abq, J=9.8 Hz, 1H), 2.32 (abq, J=9.8 Hz, 1H), 1.88 (s, 3H).

MS, MH+, 399.

Example 131

N-(4-Cyano-2-iodo-5-trifluoromethyl-phenyl)-2-methyl-acrylamide

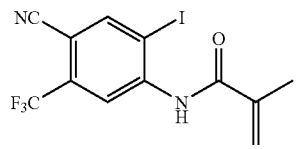

Following the procedure described in Example 1, starting from 4-amino-5-iodo-2-trifluoromethyl-benzonitrile (known compound), the title compound was prepared as off-white solid.

$^1$H NMR (CDCl$_3$) δ 9.00 (s, 1H), 8.30 (br, 1H), 8.20 (s, 1H), 6.00 (s, 1H), 5.65 (s, 1H), 2.15 (s, 3H)

MS (m/z): MH$^-$ 379

Example 132

3-Methyl-5-trifluoromethyl-3,4-dihydro-2H-pyrazole-3-carboxylic acid (4-cyano-2-iodo-5-trifluoromethyl-phenyl)-amide Compound #126

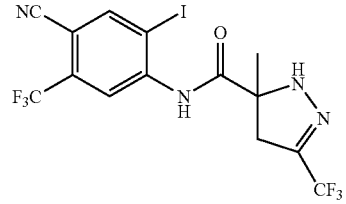

Following the procedure described in Example 29, starting from N-(4-cyano-2-iodo-5-trifluoromethyl-phenyl)-2-methyl-acrylamide, the title compound was prepared as an off-white solid.

$^1$H NMR (CDCl$_3$) δ 9.80 (s, 1H), 9.10 (s, 1H), 8.20 (s, 1H), 6.00 (s, 1H), 3.25 and 3.10 (abq, J=14.5 Hz, 2H), 1.65 (s, 3H)

MS (m/z): MH$^+$ 491.

Example 133

N-(4-Cyano-2-ethyl-3-trifluoromethyl-phenyl)-2-methyl-acrylamide

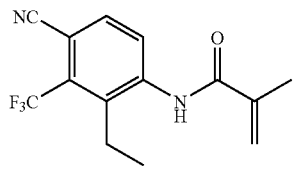

Following the procedure described in Example 1, starting from 4-amino-2-ethyl-2-trifluoromethyl-benzonitrile (known compound), the title compound was prepared as an off-white solid.

$^1$H NMR (CDCl$_3$) δ 8.60 (d, J=8.5 Hz, 1H), 7.80 (s, 1H), 7.72 (d, J=8.5 Hz, H), 5.88 (s, 1H), 5.63 (s, 1H), 2.85 (q, J=9.0 Hz, 2H), 2.12 (s, 3H), 1.40 (t, J=9.0 Hz, 3H)

MS (m/z): MH$^+$ 283.

Example 134

3-Methyl-5-trifluoromethyl-3,4-dihydro-2H-pyrazole-3-carboxylic acid (4-cyano-2-ethyl-3-trifluoromethyl-phenyl)-amide Compound #127

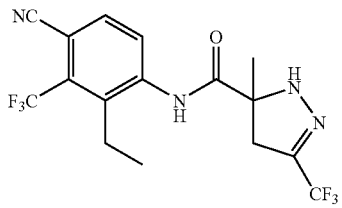

Following the procedure described in Example 29, starting from N-(4-cyano-2-ethyl-3-trifluoromethyl-phenyl)-2-methyl-acrylamide, the title compound was prepared as an off-white solid.

$^1$H NMR (MeOD) δ 9.50 (s, 1H), 8.60 (d, J=1.8 Hz, 1H), 7.70 (d, J=1.8 Hz, 1H), 5.90 (s, 1H), 3.30 and 3.05 (abq, J=12.0 Hz, 2H), 2.80 (m, 2H), 1.65 (s, 3H), 1.20 (m, 3H)

MS (m/z): MH$^+$ 393

Example 135

4-Amino-5-ethyl-2-trifluoromethyl-benzonitrile

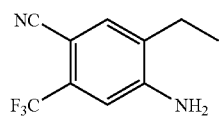

4-Amino-5-iodo-2-trifluoromethyl-benzonitrile (936 mg, 3.0 mmol), CuI (I) (57 mg, 0.3 mmol), PdCl$_2$(PPh$_3$)$_2$ (105.3 mg, 0.15 mmol), triethylamine (1.01 g, 10 mmol) and ethynyl-trimethyl-silane (450 mg, 4.5 mmol) were mixed in THF (30 ml). The reaction mixture was stirred at room temperature overnight. Tetrabutylammonium fluoride (1.0 M in THF, 3.0 ml, 3.0 mmol) was added to the reaction mixture, which was then stirred at room temperature for 20 mins. The reaction mixture was quenched by addition of H$_2$O and extracted with ethyl acetate. The organic layers were combined and washed with brine, dried over Na$_2$SO$_4$ and concentrated to yield crude product 4-amino-5-ethynyl-2-trifluoromethyl-benzonitrile.

The crude product was mixed with Pd/C (0.3 g) in methanol (50 ml) with H$_2$ (40 psi). The reaction was shaken on a Parr shaker at room temperature overnight. Upon separation on silica gel (100% CH$_2$Cl$_2$), the tile compound was obtained in as a colorless liquid.

$^1$H NMR (CDCl$_3$) δ 7.50 (s, 1H), 7.00 (s, 1H), 4.50 (br, 2H), 2.50 (m, 2H), 1.30 (m, 3H)

MS (m/z): MH$^+$ 214

Example 136

N-(4-Cyano-2-ethyl-5-trifluoromethyl-phenyl)-2-methyl-acrylamide

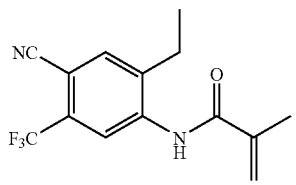

Following the procedure described in Example 1, starting from 4-amino-6-ethyl-2-trifluoromethyl-benzonitrile, the title compound was prepared as an off-white solid.

$^1$H NMR (CDCl$_3$) δ 8.80 (s, 1H), 7.70 (br, 1H), 7.65 (s, 1H), 5.90 (s, 1H), 5.60 (s, 1H), 3.70 (m, 2H), 2.10 (s, 3H), 1.30 (m, 3H)

MS (m/z): MH$^-$ 283

Example 137

3-Methyl-5-trifluoromethyl-3,4-dihydro-2H-pyrazole-3-carboxylic acid (4-cyano-2-ethyl-5-trifluoromethyl-phenyl)-amide Compound #128

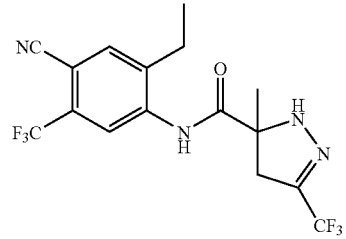

Following the procedure described in Example 29, starting from N-(4-cyano-6-ethyl-3-trifluoromethyl-phenyl)-2-methyl-acrylamide, the title compound was prepared as an off-white solid.

$^1$H NMR (CDCl$_3$) δ 9.30 (s, 1H), 8.80 (s, 1H), 7.55 (s, 1H), 5.90 (s, 1H), 3.25 and 3.10 (abq, J=14.0 Hz, 2H), 2.70 (m, 2H), 1.65 (s, 3H), 1.30 (m, 3H)

MS (m/z): MH$^+$ 393

Example 138

4-Amino-6-trifluoromethyl-isophthalonitrile

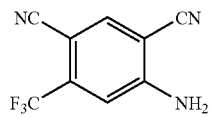

4-Amino-5-iodo-2-trifluoromethyl-benzonitrile (1.5 mmoL), CuCN (1.7 mmoL) in NMP (10 mL) was heated at 150° C. for 4 hrs. The reaction mixture was passed through a pad of Celite. The reaction mixture was then partitioned between ethyl acetate and water. The organic layer was washed with water, then brine, dried over anhydrous $Na_2SO_4$, filtered and concentrated to yield the title compound as a brown solid.

$^1$H NMR ($CDCl_3$) δ 7.82 (s, 1H), 7.15 (s, 1H), 5.45 (br, s, 2H)

MS (m/z): $MH^+$ 212

Example 139

N-(2,4-Dicyano-5-trifluoromethyl-phenyl)-2-methyl-acrylamide

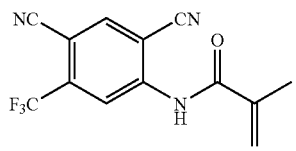

Following the procedure described in Example 1, starting from 4-amino-6-trifluoromethyl-isophthalonitrile, the title compound was prepared as an off-white solid.

$^1$H NMR ($CDCl_3$) δ 9.15 (s, 1H), 8.45 (br, s, 1H), 8.08 (s, 1H), 6.05 (s, 1H), 5.75 (s, 1H), 2.12 (s, 3H)

MS (m/z): $MH^+$ 280

Example 140

3-Methyl-5-trifluoromethyl-3,4-dihydro-2H-pyrazole-3-carboxylic acid (2,4-dicyano-5-trifluoromethyl-phenyl)-amide Compound #129

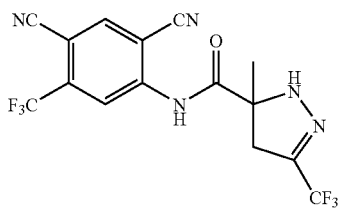

Following the procedure described in Example 29, starting from N-(2,4-dicyano-5-trifluoromethyl-phenyl)-2-methyl-acrylamide, the title compound was prepared as an off-white solid.

$^1$H NMR ($CDCl_3$) δ 10.10 (s, 1H), 9.10 (s, 1H), 8.10 (s, 1H), 6.45 (s, 1H), 3.30 and 3.10 (abq, J=14.0 Hz, 2H), 1.65 (s, 3H)

MS (m/z): $MH^+$ 390

Example 141

4-Amino-5-ethylsulfanyl-2-trifluoromethyl-benzonitrile

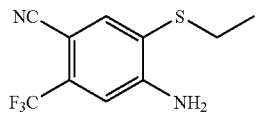

4-Amino-5-iodo-2-trifluoromethyl-benzonitrile (6.24 g, 20.0 mmol), CuI (I) (380 mg, 2.0 mmol), $K_2CO_3$ (6.52 g, 40.0 mmol) and ethylthiol (1.25 g, 20.0 mmol) were mixed in ethanol (50 ml). The reaction mixture was refluxed overnight and then the solvent was removed under vacuum. Upon separation on silica gel (100% DCM), the tile compound was obtained as a colorless liquid.

$^1$H NMR ($CDCl_3$) δ 7.70 (s, 1H), 7.00 (s, 1H), 5.10 (br, 2H), 2.85 (m, 2H), 1.25 (m, 3H)

MS (m/z): $MH_2O^+$ 264

Example 142

N-(4-Cyano-2-ethylsulfanyl-5-trifluoromethyl-phenyl)-2-methyl-acrylamide

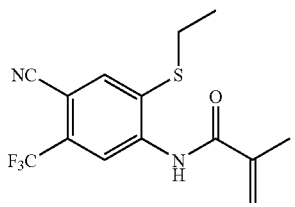

Following the procedure described in Example 1, starting from 4-amino-5-ethylsulfanyl-2-trifluoromethyl-benzonitrile, the title compound was prepared as an off-white solid.

$^1$H NMR ($CDCl_3$) δ 9.10 (br, s, 1H), 9.05 (s, 1H), 7.88 (s, 1H), 5.98 (s, 1H), 5.60 (s, 1H), 2.95 (q, J=9.5 Hz, 2H), 2.12 (s, 3H), 1.32 (t, J=9.5 Hz, 3H)

MS (m/z): $MH^+$ 315

Example 143

3-Methyl-5-trifluoromethyl-3,4-dihydro-2H-pyrazole-3-carboxylic acid (4-cyano-2-ethylsulfanyl-5-trifluoromethyl-phenyl)-amide Compound #140

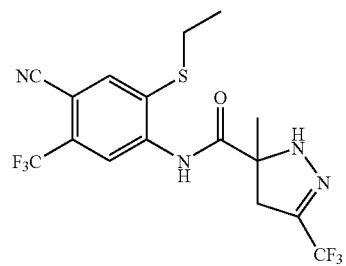

Following the procedure described in Example 29, starting from N-(4-cyano-2-ethylsulfanyl-5-trifluoromethyl-phenyl)-2-methyl-acrylamide, the title compound was prepared as an off-white solid.

$^1$H NMR (CDCl$_3$) δ 8.30 (br, 1H), 7.35 (m, 1H), 7.10 (s, 1H), 6.80 (m, 1H), 5.10 (br, 1H), 3.25 and 3.10 (abq, J=11.0 Hz, 2H), 1.60 (s, 3H)

MS (m/z): MH$^+$ 365

Example 144

3-Methyl-5-trifluoromethyl-3,4-dihydro-2H-pyrazole-3-carboxylic acid (4-cyano-2-ethanesulfonyl-5-trifluoromethyl-phenyl)-amide Compound #142

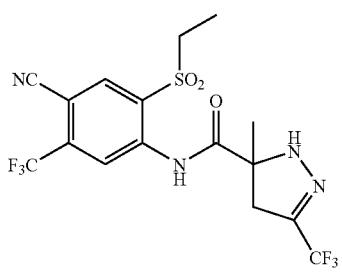

3-Methyl-5-trifluoromethyl-3,4-dihydro-2H-pyrazole-3-carboxylic acid (4-cyano-2-ethylsulfanyl-5-trifluoromethyl-phenyl)-amide (150 mg, 0.35 mmol) in ethyl acetate was treated with Oxone® (2.0 g, pH=7-8, adjusted with saturated NaHCO$_3$ and tetrabuylammonium hydrogensulfate (30 mg). The reaction mixture was stirred at room temperature overnight and then quenched with saturated NaHCO$_3$. The crude product was extracted with ethyl acetate twice, washed with brine and dried with Na$_2$SO$_4$. Upon purification on silica gel (CH$_2$Cl$_2$:EtOAc: 3:1), the title compound was obtained as a white solid.

$^1$H NMR (CDCl$_3$) δ 9.20 (s, 1H), 8.30 (s, 1H), 6.05 (s, 1H), 3.25 and 3.10 (abq, J=12.0 Hz, 2H), 3.15 (m, 2H), 1.65 (s, 3H), 1.30 (m, 3H). MS (m/z)

MH$^+$ 457

Example 145

4-Amino-5-tert-butylsulfanyl-2-trifluoromethyl-benzonitrile

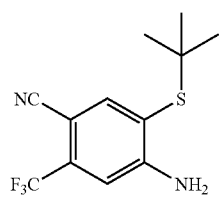

Following the procedure described in Example 141, starting from t-butyl thiol, the title compound was prepared as a brown solid.

$^1$H NMR (CDCl$_3$) δ 7.75 (s, 1H), 7.00 (s, 1H), 5.45 (br, 2H), 1.30 (s, 9H)

MS (m/z): MH$_2$O 292

Example 146

N-(2-tert-Butylsulfanyl-4-cyano-5-trifluoromethyl-phenyl)-2-methyl-acrylamide

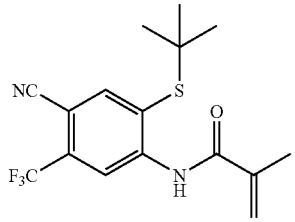

Following the procedure described in Example 1, starting from 4-amino-5-tert-butylsulfanyl-2-trifluoromethyl-benzonitrile, the title compound was prepared as an off-white solid.

$^1$H NMR (CDCl$_3$) δ 9.65 (s, 1H), 9.15 (s, 1H), 7.95 (s, 1H), 6.00 (s, 1H), 5.65 (s, 1H), 2.10 (s, 3H), 1.35 (s, 9H)

MS (m/z): MH$^-$ 341

Example 147

3-Methyl-5-trifluoromethyl-3,4-dihydro-2H-pyrazole-3-carboxylic acid (2-tert-butylsulfanyl-4-cyano-5-trifluoromethyl-phenyl)-amide Compound #143

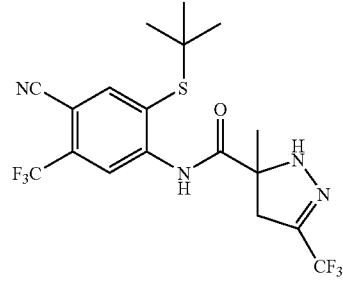

Following the procedure described in Example 29, starting from N-(2-tert-butylsulfanyl-4-cyano-5-trifluoromethyl-phenyl)-2-methyl-acrylamide, the title compound was prepared as an off-white solid.

$^1$H NMR (CDCl$_3$) δ10.75 (s, 1H), 9.10 (s, 1H), 7.95 (s, 1H), 6.00 (s, 1H), 3.20 and 3.05 (abq, J=11.0 Hz, 2H), 1.65 (s, 3H), 1.30 (s, 9H)

MS (m/z): MH$^-$ 452

Example 148

4-Amino-5-methoxy-2-trifluoromethyl-benzonitrile

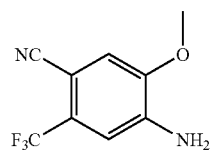

4-Amino-5-iodo-2-trifluoromethyl-benzonitrile (312 mg, 1.0 mmol), CuI (I) (20 mg, 0.1 mmol), Cs$_2$CO$_3$ (652 mg, 2.0 mmol) and 1,10-phenanthroline (36 mg, 0.2 mmol) were mixed in methanol (20 ml). The reaction mixture was refluxed overnight and then the solvent was removed under vacuum. Upon separation on silica gel (100% $CH_2Cl_2$), the tile compound was obtained as a colorless liquid.

$^1$H NMR ($CDCl_3$) δ 7.05 (s, 1H), 6.90 (s, 1H), 4.50 (br, 2H), 3.90 (s, 3H)

MS (m/z): $MH^+$ 216

Example 149

N-(4-Cyano-2-methoxy-5-trifluoromethyl-phenyl)-2-methyl-acrylamide

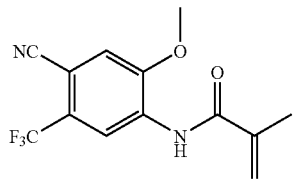

Following the procedure described in Example 1, starting from 4-amino-5-methoxy-2-trifluoromethyl-benzonitrile, the title compound was prepared as an off-white solid.

$^1$H NMR ($CDCl_3$) δ 9.00 (s, 1H), 8.40 (s, 1H), 7.26 (s, 1H), 5.90 (s, 1H), 5.60 (s, 1H), 4.00 (s, 3H), 2.10 (s, 3H)

Example 150

3-Methyl-5-trifluoromethyl-3,4-dihydro-2H-pyrazole-3-carboxylic acid (4-cyano-2-methoxy-5-trifluoromethyl-phenyl)-amide Compound #141

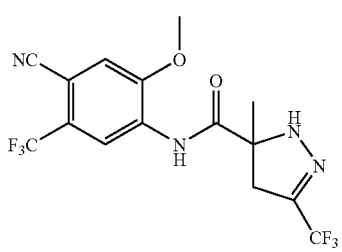

Following the procedure described in Example 29, starting from N-(4-cyano-2-methoxy-5-trifluoromethyl-phenyl)-2-methyl-acrylamide, the title compound was prepared as an off-white solid.

$^1$H NMR ($CDCl_3$) δ 9.65 (br, 1H), 8.90 (s, 1H), 7.25 (s, 1H), 5.90 (s, 1H), 4.00 (s, 3H), 3.25 and 3.05 (abq, J=10.0 Hz, 2H), 1.60 (s, 3H)

MS (m/z): $MH^+$ 395

Example 151

4-Amino-5-chloro-2-trifluoromethyl-benzonitrile

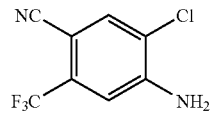

and 4-Amino-3,5-dichloro-2-trifluoromethyl-benzonitrile

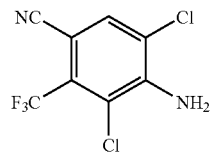

4-Amino-2-trifluoromethyl-benzonitrile (10.5 mmoL), NCS (15.5 mmoL) in MeOH (50 mL) at 0° C. was stirred for 2 hrs. The solvent was removed and the residue was partitioned between ethyl acetate and water. The organic layer was washed with sodium thiosulfate, water and brine, then dried over anhydrous $Na_2SO_4$, filtered and concentrated to yield crude material, which was then purified by column chromatography using hexanes and ethyl acetate to yield the title compounds as brown solids.

4-Amino-5-chloro-2-trifluoromethyl-benzonitrile

H NMR ($CDCl_3$) δ 7.65 (s, 1H), 7.02 (s, 1H), 4.90 (br, s, 2H)

MS (m/z): $MH^+$ 221.

4-Amino-3,5-dichloro-2-trifluoromethyl-benzonitrile $^1$H NMR ($CDCl_3$) δ 7.61 (s, 1H), 5.32 (br, s, 2H)

MS (m/z): $MH^+$ 256.

Example 152

N-(2-Chloro-4-cyano-5-trifluoromethyl-phenyl)-2-methyl-acrylamide

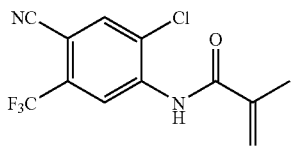

Following the procedure described in Example 1, starting from 4-amino-5-chloro-2-trifluoromethyl-benzonitrile, the title compound was prepared as an off-white solid.

$^1$H NMR ($CDCl_3$) δ 7.95 (s, 1H), 7.52 (s, 1H), 5.80 (br, s, 1H), 5.65 (s, 1H), 5.60 (s, 1H)

MS (m/z): $MH^+$ 289

Example 153

3-Methyl-5-trifluoromethyl-3,4-dihydro-2H-pyrazole-3-carboxylic acid (2-chloro-4-cyano-5-trifluoromethyl-phenyl)-amide Compound #130

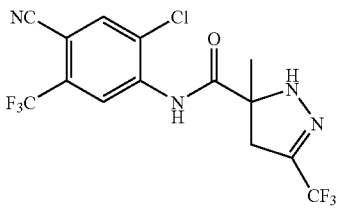

Following the procedure described in Example 29, starting from N-(2-chloro-4-cyano-5-trifluoromethyl-phenyl)-2-methyl-acrylamide, the title compound was prepared as an off-white solid.

$^1$H NMR (CDCl$_3$) δ 9.88 (br, s, 1H), 9.05 (s, 1H), 7.90 (s, 1H), 3.31 (abq, J=10.5 Hz, 1H), 3.15 (abq, J=11.0 Hz, 1H), 1.68 (s, 3H)

MS (m/z): MH$^+$ 399

Example 154

N-(2,6-Dichloro-4-cyano-3-trifluoromethyl-phenyl)-2-methyl-acrylamide

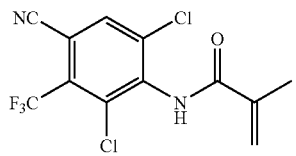

Following the procedure described in Example 1, starting from 4-amino-3,5-dichloro-2-trifluoromethyl-benzonitrile, the title compound was prepared as an off-white solid.

$^1$H NMR (CDCl$_3$) δ 7.88 (s, 1H), 7.50 (s, 1H), 6.02 (s, 1H), 5.68 (s, 1H), 2.11 (s, 3H)

MS (m/z): MH$^+$ 324

Example 155

3-Methyl-5-trifluoromethyl-4,5-dihydro-3H-pyrazole-3-carboxylic acid (2,6-dichloro-4-cyano-3-trifluoromethyl-phenyl)-amide Compound #137

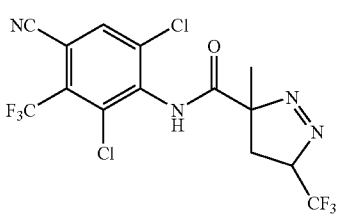

and 3-Methyl-5-trifluoromethyl-3,4-dihydro-2H-pyrazole-3-carboxylic acid (2,6-dichloro-4-cyano-3-trifluoromethyl-phenyl)-amide Compound #139

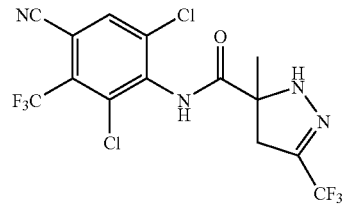

and 3-Methyl-5-trifluoromethyl-3,4-dihydro-2H-pyrazole-3-carboxylic acid (2,6-dichloro-4-cyano-3-trifluoromethyl-phenyl)-(2,2,2-trifluoro-ethyl)-amide Compound #138

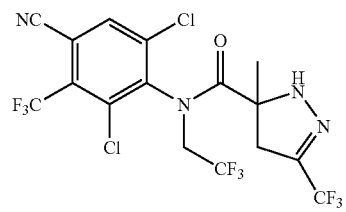

Following the procedure described in Example 29, starting from N-(2,6-dichloro-4-cyano-3-trifluoromethyl-phenyl)-2-methyl-acrylamide, the title compounds were prepared as off-white solids.

3-Methyl-5-trifluoromethyl-4,5-dihydro-3H-pyrazole-3-carboxylic acid (2,6-dichloro-4-cyano-3-trifluoromethyl-phenyl)-amide $^1$H NMR (CDCl$_3$) δ 8.82 (s, 1H), 7.71 (s, 1H), 3.70 (m, 1H), 3.60 (m, 1H), 2.85 (m, 1H), 1.35 (s, 3H)

MS (m/z): MH$^+$ 434.

3-Methyl-5-trifluoromethyl-3,4-dihydro-2H-pyrazole-3-carboxylic acid (2,6-dichloro-4-cyano-3-trifluoromethyl-phenyl)-amide $^1$H NMR (CDCl$_3$) δ 9.08 (s, 1H), 7.50 (s, 1H), 5.72 (s, 1H), 3.25 (abq, J=10.5 Hz, 1H), 2.85 (abq, J=10.5 Hz, 1H), 1.58 (s, 3H)

MS (m/z): MH$^+$ 434.

3-Methyl-5-trifluoromethyl-3,4-dihydro-2H-pyrazole-3-carboxylic acid (2,6-dichloro-4-cyano-3-trifluoromethyl-phenyl)-(2,2,2-trifluoro-ethyl)-amide $^1$H NMR (CDCl$_3$) δ 7.88 (s, 1H), 5.62 (m, 1H), 3.75 (m, 2H), 3.58 (abq, J=12.5 Hz, 1H), 2.92 (abq, J=12.5 Hz, 1H), 1.68 (s, 3H)

MS (m/z): MH$^+$ 516

Example 156

3-Methyl-2-(2,2,2-trifluoro-acetyl)-5-trifluoromethyl-3,4-dihydro-2H-pyrazole-3-carboxylic acid (4-cyano-3-trifluoromethyl-phenyl)-amide Compound #131

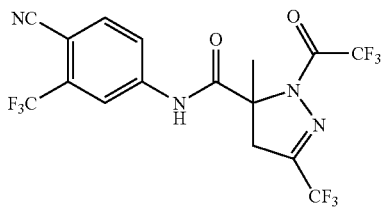

3-Methyl-5-trifluoromethyl-3,4-dihydro-2H-pyrazole-3-carboxylic acid (4-cyano-3-trifluoromethyl-phenyl)-amide (1.5 mmoL) in DCM (~20 mL) was reacted with pyridine (2.0 mmoL) followed by trifluoroacetic anhydride (1.5 mmoL) which was added dropwise at 0° C. The reaction mixture was then stirred for 2 hrs. The solvent was removed and the residue was partitioned between DCM and water. The organic layer was washed with saturated sodium bicarbonate, water and then brine, dried over anhydrous $Na_2SO_4$, filtered and concentrated to yield crude material, which was then purified by column chromatography using hexanes and ethyl acetate to yield the title compound as an off-white solid.

$^1$H NMR (CDCl$_3$) δ 9.72 (s, 1H), 8.08 (s, 1H), 7.88 (d, J=8.5 Hz, 1H), 7.80 (d, J=8.5 Hz, 1H), 4.35 (abq, J=12.5 Hz, 1H), 3.10 (abq, J=12.5 Hz, 1H), 2.01 (s, 3H)

MS (m/z): MH$^+$ 461

Example 157

2-Ethyl-3-methyl-5-trifluoromethyl-3,4-dihydro-2H-pyrazole-3-carboxylic acid (4-cyano-3-trifluoromethyl-phenyl)-methyl-amide Compound #123

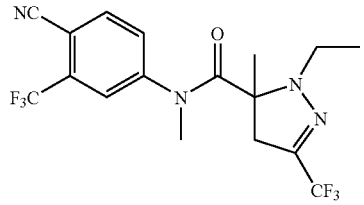

2-Ethyl-3-methyl-5-trifluoromethyl-3,4-dihydro-2H-pyrazole-3-carboxylic acid (4-cyano-3-trifluoromethyl-phenyl)-amide (1.1 mmoL) in DMF (10 mL) was treated with NaH (60%, 1.2 mmoL) followed by CH$_3$I (1.1 mmoL) at 0° C. The reaction mixture was stirred for 1 hr and then warmed to room temperature. The reaction mixture was then partitioned between diethyl ether and water. The organic layer was washed with saturated sodium bicarbonate, water and then brine, dried over anhydrous $Na_2SO_4$, filtered and concentrated to yield crude material, which was then purified by column chromatography using hexanes and ethyl acetate to yield the title compound as an off-white solid.

$^1$H NMR (CDCl$_3$) δ 7.80 (m, 1H), 7.60 (s, 1H), 7.45 (m, 1H), 3.40 (s, 3H), 3.35 and 2.90 (abq, J=14.0 Hz, 2H), 3.20 (m, 1H), 3.00 (m, 1H), 1.50 (s, 3H), 1.15 (t, J=3.0 Hz, 3H)

MS (m/z): MH$^+$ 390

Example 158

3,5-Dimethyl-4,5-dihydro-isoxazole-5-carboxylic acid (4-cyano-3-trifluoromethyl-phenyl)-amide Compound #134

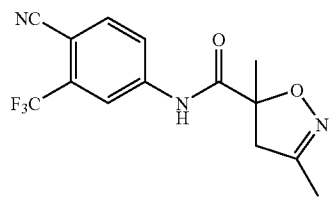

Following the procedure described in Example 27, starting from acetaldehyde oxime, the title compound was prepared as an off-white solid.

$^1$H NMR (CDCl$_3$) δ 8.65 (s, 1H), 7.95 (s, 1H), 7.40 (m, 2H), 3.40 and 2.95 (abq, J=14.0 Hz, 2H), 2.00 (s, 3H), 1.70 (s, 3H)

MS (m/z): MH$^+$ 390

Example 159

3-Methyl-5-trifluoromethyl-3,4-dihydro-2H-pyrazole-3-carbothioic acid (4-cyano-3-trifluoromethyl-phenyl)-amide Compound #118

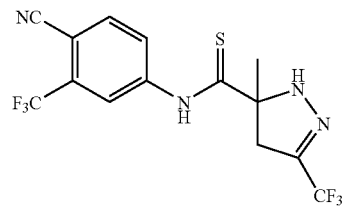

3-Methyl-5-trifluoromethyl-3,4-dihydro-2H-pyrazole-3-carboxylic acid (4-cyano-3-trifluoromethyl-phenyl)-amide (15 mmoL) and Lawesson's agent (15 mmoL) in toluene (100 mL) was refluxed for 6 hrs until the solution turned clear. The reaction mixture was then cooled and some precipitate was observed. The solid was removed by filtration and the filtrate was concentrated to yield crude product as a green oil. The green oil was purified by silica gel column chromatography using DCM and ethyl acetate as eluent to yield the title compound as a green solid.

$^1$H NMR (CDCl$_3$) δ 11.05 (s, 1H), 8.45 (s, 1H), 8.30 (d, J=8.5 Hz, 1H), 7.82 (d, J=8.5 Hz, 1H), 5.95 (br, s, 1H), 3.40 (abq, J=9.5 Hz, 1H), 3.21 (abq, J=9.5 Hz, 1H), 1.85 (s, 3H)

MS (m/z): MH$^+$ 381

Example 160

N-(4-Cyano-3-trifluoromethyl-phenyl)-3-methyl-5-trifluoromethyl-3,4-dihydro-2H-pyrazole-3-carboximidothioic acid ethyl ester Compound #204

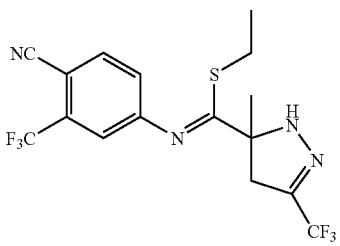

3-Methyl-5-trifluoromethyl-3,4-dihydro-2H-pyrazole-3-carbothioic acid (4-cyano-3-trifluoromethyl-phenyl)-amide (10 mmoL), $K_2CO_3$ (15 mmoL) in acetone was treated with $CH_3CH_2I$ (10 mmoL) at room temperature. The reaction mixture was heated gently and then stirred at 50° C. for 1 hr. The solid was filtrated and the filtrate was concentrated to yield crude product as a brown oil, which was then purified by silica gel column chromatography using hexanes and ethyl acetate as eluent to yield the title compound as a colorless oil.

$^1$H NMR (CDCl$_3$) δ7.80 (d, J=7.8 Hz, 1H), 7.28 (s, 1H), 7.15 (d, J=7.9 Hz, 1H), 6.50 (s, 1H), 3.51 (abq, J=12.5 Hz, 1H), 2.88 (abq, J=12.5 Hz, 1H), 2.35 (q, J=8.5 Hz, 2H), 1.08 (t, J=8.5 Hz, 3H)

MS (m/z): MH$^+$ 409

Example 161

N-(4-Cyano-3-trifluoromethyl-phenyl)-N'-ethyl-3-methyl-5-trifluoromethyl-3,4-dihydro-2H-pyrazole-3-carboxamidine or its tautomer N-(4-Cyano-3-trifluoromethyl-phenyl)-N'-ethyl-3-methyl-5-trifluoromethyl-3,4-dihydro-2H-pyrazole-3-carboxamidine Compound #205 or its Tautomer

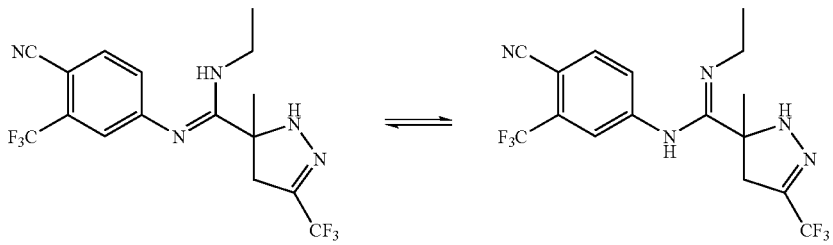

N-(4-Cyano-3-trifluoromethyl-phenyl)-3-methyl-5-trifluoromethyl-3,4-dihydro-2H-pyrazole-3-carboximidothioic acid ethyl ester (2 mmoL) in dioxane (15 mL) was treated with ethyl amine/THF solution (~3 mmoL) and $K_2CO_3$ (2 mmoL) at 70° C. The reaction mixture was then stirred 4 hr. The solid was removed by filtration. The filtrate was concentrated to yield crude product, which was then purified by silica gel column chromatography using hexanes and ethyl acetate as eluent to yield the title compound as a white solid.

$^1$H NMR (CDCl$_3$) δ 7.62 (d, J=7.5 Hz, 1H), 7.10 (s, 1H), 6.95 (d, J=7.5 Hz, 1H), 6.15 (s, 1H), 5.78 (s, 1H), 3.20 (abq, J=9.5 Hz, 1H), 2.95 (abq, J=9.5 Hz, 1H), 2.85 (q, J=8.0 Hz, 2H), 1.48 (s, 3H), 1.30 (t, J=8.0 Hz, 3H)

MS (m/z): MH$^+$ 392

Example 162

N-(4-Cyano-3-trifluoromethyl-phenyl)-N'-hydroxy-3-methyl-5-trifluoromethyl-3,4-dihydro-2H-pyrazole-3-carboxamidine or its tautomer N-(4-Cyano-3-trifluoromethyl-phenyl)-N'-hydroxy-3-methyl-5-trifluoromethyl-3,4-dihydro-2H-pyrazole-3-carboxamidine Compound #206 or its Tautomer

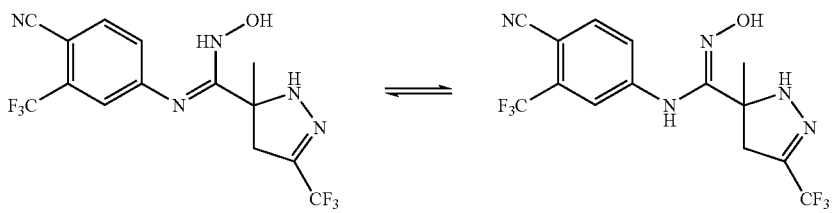

N-(4-Cyano-3-trifluoromethyl-phenyl)-3-methyl-5-trifluoromethyl-3,4-dihydro-2H-pyrazole-3-carboximidothioic acid ethyl ester (1 mmoL) in DMF (5 mL) was treated with N-hydroxamine hydrochloride salt (1 mmoL) and $K_2CO_3$ (2 mmoL) at room temperature. The reaction mixture was then stirred for 4 hr. The solid was removed by filtration. The filtrate was partitioned between ethyl acetate and water. The organic layer was dried over anhydrous sodium sulfate, filtrated and concentrated to yield crude product, which was then purified by silica gel column chromatography using hexanes and ethyl acetate as eluent to yield the title compound as a white solid.

$^1$H NMR (CDCl$_3$) δ 8.20 (s, 1H), 7.62 (d, J=7.5 Hz, 1H), 7.05 (s, 1H), 6.85 (d, J=7.5 Hz, 1H), 5.92 (s, 1H), 3.25 (abq, J=8.8 Hz, 1H), 2.82 (abq, J=8.8 Hz, 1H), 1.50 (s, 3H)

MS (m/z): MH$^+$ 380

Example 163

N-(4-Cyano-3-trifluoromethyl-phenyl)-N'-methoxy-3-methyl-5-trifluoromethyl-3,4-dihydro-2H-pyrazole-3-carboxamidine or its tautomer N-(4-Cyano-3-trifluoromethyl-phenyl)-N'-methoxy-3-methyl-5-trifluoromethyl-3,4-dihydro-2H-pyrazole-3-carboxamidine Compound #210 or its Tautomer

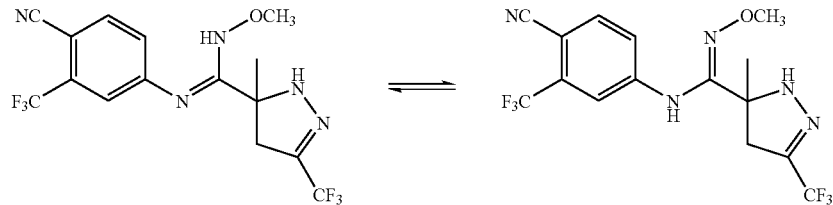

Following the procedure described in Example 162, starting from O-methyl-hydroxylamine and N-(4-Cyano-3-trifluoromethyl-phenyl)-3-methyl-5-trifluoromethyl-3,4-dihydro-2H-pyrazole-3-carboximidothioic acid ethyl ester, the title compound was prepared as an off-white solid.

$^1$H NMR (CDCl$_3$) δ 7.72 (d, J=6.5 Hz, 1H), 7.22 (s, 1H), 7.11 (d, J=6.5 Hz, 1H), 6.12 (s, 1H), 3.60 (s, 3H), 3.50 (abq, J=8.5 Hz, 1H), 2.95 (abq, J=8.5 Hz, 1H), 1.58 (s, 3H)

MS (m/z): MH$^+$ 394

Example 164

N-(4-Cyano-3-trifluoromethyl-phenyl)-3-methyl-5-trifluoromethyl-3,4-dihydro-2H-pyrazole-3-carboxamidine or its tautomer N-(4-Cyano-3-trifluoromethyl-phenyl)-3-methyl-5-trifluoromethyl-3,4-dihydro-2H-pyrazole-3-carboxamidine Compound #207 or its Tautomer and N-(4-Cyano-3-trifluoromethyl-phenyl)-3-methyl-5-trifluoromethyl-3,4-dihydro-2H-pyrazole-3-carboximidic acid methyl ester Compound #212

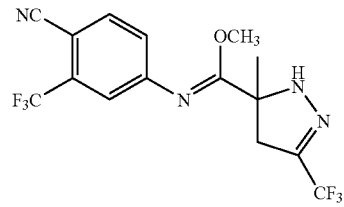

N-(4-Cyano-3-trifluoromethyl-phenyl)-3-methyl-5-trifluoromethyl-3,4-dihydro-2H-pyrazole-3-carboximidothioic acid ethyl ester (1.2 mmoL) in dioxane (10 mL) was treated with ammonia in MeOH (7N solution, ~10 mL) in a sealed tube. The reaction mixture was heated to 100° C. for 4 hrs. The solvent was removed and the residue was purified by silica gel column chromatography using ethyl acetate and methanol as eluent to yield the title compounds as white solids.

N-(4-Cyano-3-trifluoromethyl-phenyl)-3-methyl-5-trifluoromethyl-3,4-dihydro-2H-pyrazole-3-carboxamidine $^1$H NMR (CDCl$_3$) δ 9.50 (br, s, 1H), 8.11 (s, 1H), 7.95 (d, J=7.5 Hz, 1H), 7.78 (d, J=7.5 Hz, 1H), 5.63 (s, 1H), 3.05 (abq, J=10.5 Hz, 1H), 2.95 (abq, J=10.5 Hz, 1H), 1.58 (s, 3H)

MS (m/z): MH$^+$ 364.

N-(4-Cyano-3-trifluoromethyl-phenyl)-3-methyl-5-trifluoromethyl-3,4-dihydro-2H-pyrazole-3-carboximidic acid methyl ester MS (m/z): MH$^+$ 379.

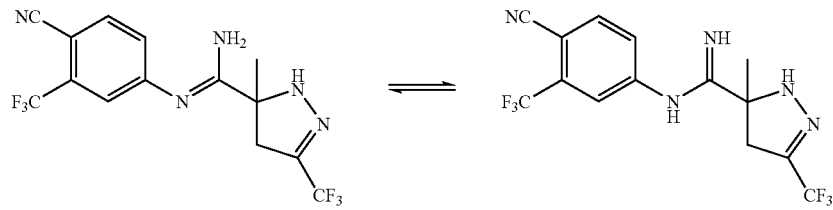

Example 165

N-(4-Cyano-3-trifluoromethyl-phenyl)-3,N'-dimethyl-5-trifluoromethyl-3,4-dihydro-2H-pyrazole-3-carboxamidine or its tautomer N-(4-Cyano-3-trifluoromethyl-phenyl)-3,N'-dimethyl-5-trifluoromethyl-3,4-dihydro-2H-pyrazole-3-carboxamidine Compound #211 or its Tautomer

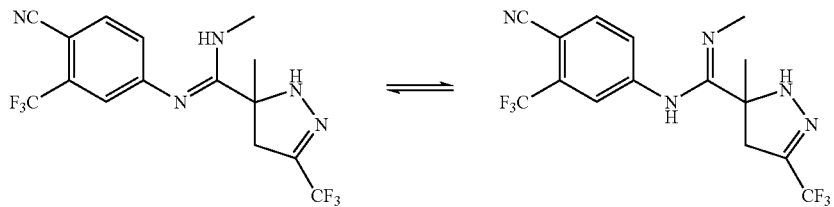

Following the procedure described in Example 164, starting from methyl amine and N-(4-cyano-3-trifluoromethyl-phenyl)-3-methyl-5-trifluoromethyl-3,4-dihydro-2H-pyrazole-3-carboximidothioic acid ethyl ester, the title compound was prepared as an off-white solid.

$^1$H NMR (CDCl$_3$) δ 7.60 (d, J=8.5 Hz, 1H), 7.00 (s, 1H), 6.90 (d, J=8.5 Hz, 1H), 6.05 (s, 1H), 5.60 (s, 1H), 3.15 (abq, J=10.5 Hz, 1H), 2.85 (abq, J=10.5 Hz, 1H), 2.90 (s, 3H), 1.45 (s, 3H)

MS (m/z): MH$^+$ 378

Example 166

N'-(4-Cyano-3-trifluoromethyl-phenyl)-N,N-diethyl-3-methyl-5-trifluoromethyl-3,4-dihydro-2H-pyrazole-3-carboxamidine Compound #208

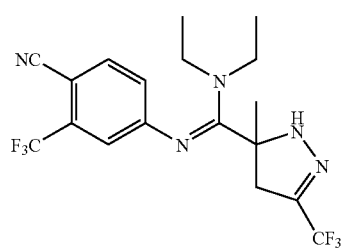

Following the procedure described in Example 164, starting from diethyl amine and N-(4-cyano-3-trifluoromethyl-phenyl)-3-methyl-5-trifluoromethyl-3,4-dihydro-2H-pyrazole-3-carboximidothioic acid ethyl ester, the title compound was prepared as an off-white solid.

$^1$H NMR (CDCl$_3$) δ 7.72 (d, J=7.5 Hz, 1H), 7.21 (s, 1H), 7.10 (d, J=7.5 Hz, 1H), 6.31 (s, 1H), 3.70 (q, J=5.5 Hz, 1H), 3.55 (abq, J=10.5 Hz, 1H), 3.45 (q, J=5.5 Hz, 1H), 3.05 (abq, J=10.5 Hz, 1H), 1.55 (s, 3H), 1.20 (t, J=8.5 Hz, 6H)

MS (m/z): MH$^+$ 420

Example 167

4-{[(3-Methyl-5-trifluoromethyl-3,4-dihydro-2H-pyrazol-3-yl)-pyrrolidin-1-yl-methylene]-amino}-2-trifluoromethyl-benzonitrile Compound #209

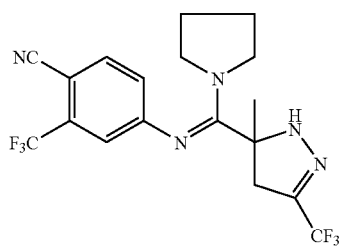

Following the procedure described in Example 164, starting from pyrrolidine and N-(4-cyano-3-trifluoromethyl-phenyl)-3-methyl-5-trifluoromethyl-3,4-dihydro-2H-pyrazole-3-carboximidothioic acid ethyl ester, the title compound was prepared as an off-white solid.

$^1$H NMR (CDCl$_3$) δ 7.71 (d, J=7.0 Hz, 1H), 7.22 (s, 1H), 7.08 (d, J=7.0 Hz, 1H), 3.77 (t, J=6.0 Hz, 1H), 3.62 (t, J=6.0 Hz, 1H), 3.60 (abq, J=9.5 Hz, 1H), 3.05 (abq, J=9.5 Hz, 1H), 1.95~1.70 (m, 4H), 1.58 (s, 3H)

MS (m/z): MH$^+$ 418

Example 169

N-[(4-Cyano-3-trifluoromethyl-phenylimino)-(3-methyl-5-trifluoromethyl-3,4-dihydro-2H-pyrazol-3-yl)-methyl]-methanesulfonamide or its tautomer N-[(4-Cyano-3-trifluoromethyl-phenylamino)-(3-methyl-5-trifluoromethyl-3,4-dihydro-2H-pyrazol-3-yl)-methylene]-methanesulfonamide Compound #214 or its Tautomer

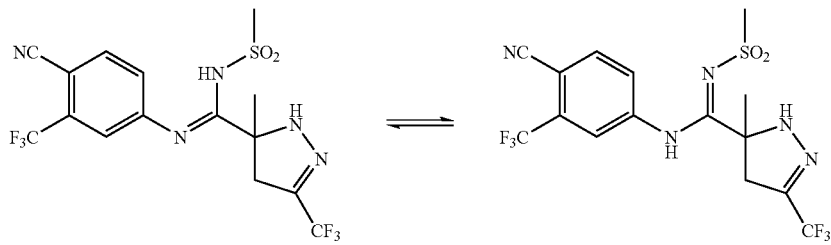

Following the procedure described in Example 164, starting from methylsulfonamide and N-(4-cyano-3-trifluoromethyl-phenyl)-3-methyl-5-trifluoromethyl-3,4-dihydro-2H-pyrazole-3-carboximidothioic acid ethyl ester, the title compound was prepared as an off-white solid.

$^1$H NMR (CDCl$_3$) δ 7.85 (br, s, 1H), 7.75 (d, J=7.5 Hz, 1H), 7.58 (s, 1H), 7.20 (d, J=7.5 Hz, 1H), 7.05 (br, s, 1H), 3.62 (abq, J=10.5 Hz, 1H), 3.32 (abq, J=10.5 Hz, 1H), 1.61 9s, 3H)

MS (m/z): MH$^+$ 442

Example 169

5-Nitro-2-[(3-methyl-3,4-dihydro-2H-pyrazole-3-carbonyl)-amino]-benzoic acid methyl ester Compound #147

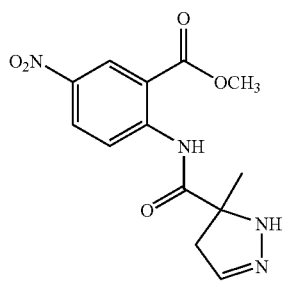

Following the procedure described in Example 29, starting from 5-nitro-2-(2-methyl-acryloylamino)-benzoic acid methyl ester, the title compound was prepared as an off-white solid.

$^1$H NMR (CDCl$_3$) δ 8.95 (d, J=7.5 Hz, 1H), 8.90 (s, 1H), 8.48 (d, J=7.5 Hz, 1H), 6.80 (s, 1H), 5.61 (s, 1H), 4.01 (s, 3H), 3.10 (abq, J=10.5 Hz, 1H), 2.90 (abq, J=10.5 Hz, 1H), 1.55 (s, 3H)

MS (m/z): MH$^+$ 307

Example 170

3-Methyl-5-trifluoromethyl-3,4-dihydro-2H-pyrazole-3-carbothioic acid (3,4-dichloro-phenyl)-amide Compound #136

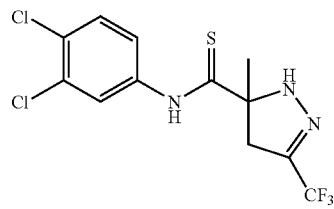

Following the procedure described in Example 159, starting from 3-methyl-5-trifluoromethyl-3,4-dihydro-2H-pyrazole-3-carboxylic acid (3,4-dichloro-phenyl)-amide, the title compound was prepared as a green oil.

$^1$H NMR (CDCl$_3$) δ10.70 (s, 1H), 8.10 (s, 1H), 7.65 (m, 1H), 7.45 (m, 1H), 5.80 (s, 1H), 3.30 and 3.15 (abq, J=13.0 Hz, 2H), 1.80 (s, 3H)

MS (m/z): MH$^+$ 357

Example 171

N-(3,4-Dichloro-phenyl)-3-methyl-5-trifluoromethyl-3,4-dihydro-2H-pyrazole-3-carboximidothioic acid ethyl ester Compound #213

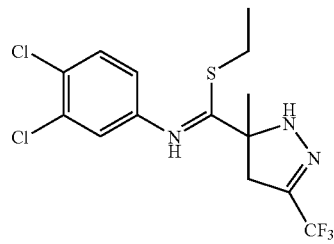

Following the procedure described in Example 160, starting from 3-methyl-5-trifluoromethyl-3,4-dihydro-2H-pyrazole-3-carbothioic acid (3,4-dichloro-phenyl)-amide, the title compound was prepared as a colorless oil.

$^1$H NMR (CDCl$_3$) δ 7.40 (m, 1H), 7.00 (s, 1H), 6.80 (m, 1H), 6.60 (br, 1H), 5.30 (s, 1H), 3.50 and 2.80 (abq, J=14.0 Hz, 2H), 2.30 (m, 2H), 1.60 (s, 3H), 1.00 (m, 3H)

MS (m/z): MH$^+$ 385

Example 172

3(R)-Methyl-5-trifluoromethyl-3,4-dihydro-2H-pyrazole-3-carbothioic acid (4-cyano-3-trifluoromethyl-phenyl)-amide Compound #144

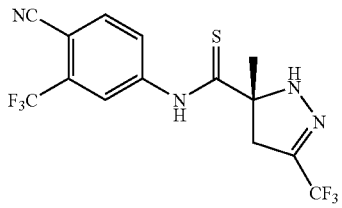

Following the procedure described in Example 159, starting from 3(R)-methyl-5-trifluoromethyl-3,4-dihydro-2H-pyrazole-3-carboxylic acid (3-trifluoromethyl-4-cyano-phenyl)-amide, the title compound was prepared as a green oil.

NMR and MS data are the same as described in Example 159.

Example 173

N-(4-Cyano-3-trifluoromethyl-phenyl)-3(R)-methyl-5-trifluoromethyl-3,4-dihydro-2H-pyrazole-3-carboximidothioic acid ethyl ester Compound #215

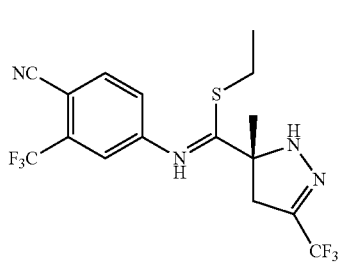

Following the procedure described in Example 160, starting from 3(R)-methyl-5-trifluoromethyl-3,4-dihydro-2H-pyrazole-3-carbothioic acid (4-cyano-3-trifluoromethyl-phenyl)-amide, the title compound was prepared as a colorless oil.

NMR and MS data are the same as described in Example 160.

Example 174

3(S)-Methyl-5-trifluoromethyl-3,4-dihydro-2H-pyrazole-3-carbothioic acid (4-cyano-3-trifluoromethyl-phenyl)-amide Compound #145

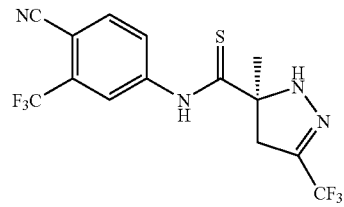

Following the procedure described in Example 159, starting from 3(S)-methyl-5-trifluoromethyl-3,4-dihydro-2H-pyrazole-3-carboxylic acid (3-trifluoromethyl-4-cyano-phenyl)-amide, the title compound was prepared as a green oil.

NMR and MS data are the same as described in Example 159.

Example 175

N-(4-Cyano-3-trifluoromethyl-phenyl)-3(S)-methyl-5-trifluoromethyl-3,4-dihydro-2H-pyrazole-3-carboximidothioic acid ethyl ester Compound #216

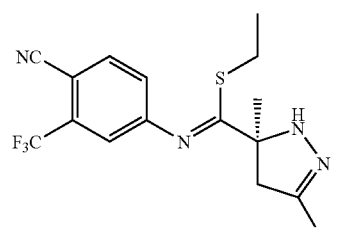

Following the procedure described in Example 160, starting from 3-(S)-methyl-5-trifluoromethyl-3,4-dihydro-2H-pyrazole-3-carbothioic acid (4-cyano-3-trifluoromethyl-phenyl)-amide, the title compound was prepared as a colorless oil.

NMR and MS data are the same as described in Example 160.

Example 176

N-(4-Cyano-3-trifluoromethyl-phenyl)-2-ethyl-3(S)-methyl-5-trifluoromethyl-3,4-dihydro-2H-pyrazole-3-carboximidothioic acid ethyl ester Compound #218

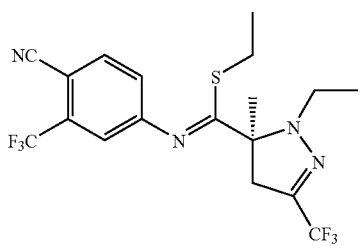

Following the procedure described in Example 126, starting from N-(4-cyano-3-trifluoromethyl-phenyl)-3(S)-methyl-5-trifluoromethyl-3,4-dihydro-2H-pyrazole-3-carboximidothioic acid ethyl ester, the title compound was prepared as a colorless oil.

$^1$H NMR (CDCl$_3$) δ 7.75 (d, J=7.5 Hz, 1H), 7.20 (s, 1H), 7.08 (D, j=7.5 Hz, 1H), 3.50 (m, 2H), 3.28 (abq, J=12.5 Hz, 1H), 2.85 (abq, J=12.5 hz, 1H), 2.48 (m, 2H), 1.50 (s, 3H), 1.35 (t, J=9.5 Hz, 3H), 1.28 (t, J=9.5 Hz, 3H)

MS (m/z): MH$^+$ 437

Example 177

N-(4-Cyano-3-trifluoromethyl-phenyl)-N'-cyano-2-ethyl-3(S)-methyl-5-trifluoromethyl-3,4-dihydro-2H-pyrazole-3-carboxamidine or its tautomer N'-cyano-N-[4-cyano-3-(trifluoromethyl)phenyl]-1-ethyl-4,5-dihydro-5(S)-methyl-3-(trifluoromethyl)-H-pyrazole-5-carboximidamide Compound #217 or its Tautomer

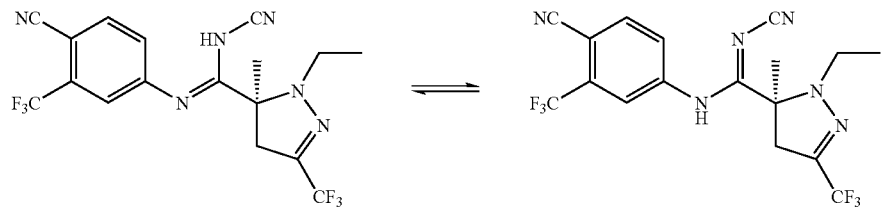

N-(4-Cyano-3-trifluoromethyl-phenyl)-2-ethyl-3-(S)-methyl-5-trifluoromethyl-3,4-dihydro-2H-pyrazole-3-carboximidothioic acid ethyl ester (0.7 mmoL) in dioxane (5 mL) was treated with K$_2$CO$_3$ (1.4 mmoL) and NH$_2$CN (1.0 mmoL) at 80° C. for 2 hr. The reaction mixture was then filtrated through a pad of Celite. The filtrate was concentrated and purified by silica gel column chromatography using hexanes and ethyl acetate as eluent to yield the title compound as a white solid.

$^1$H NMR (CDCl$_3$) δ 9.25 (br, s, 1H), 8.05 (s, 1H), 8.01 (d, J=7.5 Hz, 1H), 7.85 (d, J=7.5 Hz, 1H), 3.40 (abq, J=11.5 Hz, 2H), 3.28 (m, 1H), 3.05 (m, 1H), 1.90 (s, 3H), 1.55 (t, J=85 Hz, 3H)

MS (m/z): MH$^+$ 417

Example 178

4-Methyl-2-trifluoromethyl-4,5-dihydro-oxazole-4-carboxylic acid (4-cyano-3-trifluoromethyl-phenyl)-amide Compound #110

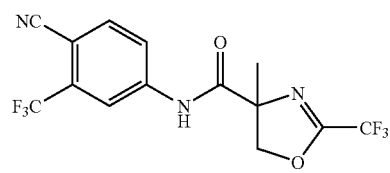

3-Hydroxy-2-methyl-2-(2,2,2-trifluoro-acetylamino)-propionic acid (3.2 mmoL) in DMA (10 mL) was treated dropwise with thionyl chloride (4.5 mmoL) at 0° C. for 30 min. To the resulting solution was added 4-amino-2-trifluoromethyl-benzonitrile (3.2 mmoL) in DMA (5 mL) followed by TEA (5 mmoL). The reaction mixture was slowly warmed to room temperature and stirred overnight. The reaction mixture was then partitioned between ethyl acetate and water. The organic layer was washed with saturated sodium bicarbonate, then brine, dried over anhydrous sodium sulfate, filtrated and concentrated to yield crude product, which was then purified by silica gel column chromatography using hexanes and ethyl acetate as eluent to yield the title compound as a white solid.

$^1$H NMR (CDCl$_3$) δ 8.62 (s, 1H), 8.05 (s, 1H), 8.13 (d, J=6.8 Hz, 1H), 7.32 (d, J=6.8 Hz, 1H), 4.65 (abq, J=8.5 Hz, 1H), 4.45 (abq, J=8.5 Hz, 1H), 1.55 (s, 3H)

Example 179

4-Methyl-2-oxo-oxazolidine-4-carboxylic acid (4-cyano-3-trifluoromethyl-phenyl)-amide Compound #111

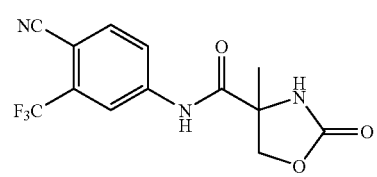

Following the procedure described in Example 178, starting from 2-tert-butoxycarbonylamino-3-hydroxy-2-methyl-propionic acid (prepared by literature known method), the title compound was prepared as a white solid.

$^1$H NMR (CDCl$_3$) δ 8.31 (br, s, 1H), 8.05 (s, 1H), 7.95 (d, J=8.5 Hz, 1H), 7.72 (d, J=8.5 Hz, 1H), 6.01 (s, 1H), 4.65 (d, J=8.0 Hz, 1H), 4.23 (d, J=8.0 Hz, 1H), 1.68 (s, 3H)

MS (m/z): MH$^+$ 314

Example 180

Ventral Prostate and Levator Ani Weight In Vivo Assay

Mature (150 to 200 g) castrated male Sprague Dawley rats (Charles River) were treated once daily for 14 days with test compound (usually administered by oral gavage at up to the desired dosage, up to 30 mg/kg in a volume of 1 mL, in 30% cyclodextrin or 0.5% methylcellulose vehicle), or with testosterone propionate (administered subcutaneously by injection at the nape of the neck at 5 mg/kg, in a volume of 0.1 mL in sesame oil), or with vehicle (1 mL of 30% cyclodextrin or 0.5% methylcellulose, given orally). On the fifteenth day, the rats were euthanized by asphyxiation in carbon dioxide. Ventral prostates and levator ani muscles were removed and their wet weights determined.

Test compound activity was determined as the percent stimulation of tissue weight, with the vehicle-treated control group set to zero percent and the testosterone alone-treated control group set to 100%. A compound was designated as agonist active if it produced greater than or equal to 20% stimulation of levator ani at 30 mg/kg.

Representative compounds of the present invention were tested according to the procedure described, with results as listed in Table 10 below. For the compounds listed in Table 10 as "inactive", one skilled in the art will recognize that said compounds may or may not have shown an effect on prostate and/or vesical weight, rather they are listed herein as "inactive" as they did not meet the specified criteria defined above. A designation of "toxic" indicates that the compound exhibited toxicity in the rats tested.

TABLE 10

| ID # | % Prostate Stimulation | % levator ani Stimulation |
|---|---|---|
| 8 | active | active |
| 9 | inactive | inactive |
| 11 | inactive | inactive |
| 15 | inactive | inactive |
| 17 | inactive | inactive |
| 27 | inactive | inactive |
| 30 | inactive | active |
| 33 | inactive | active |
| 34 | inactive | inactive |
| 35 | active | active |
| 36 | inactive | active |
| 37 | inactive | active |
| 38 | inactive | inactive |
| 39 | inactive | inactive |
| 40 | inactive | inactive |
| 41 | inactive | inactive |
| 43 | inactive | active |
| 44 | inactive | inactive |
| 45 | inactive | inactive |
| 46 | inactive | inactive |
| 47 | inactive | inactive |
| 48 | inactive | inactive |
| 73 | inactive | inactive |
| 74 | active | active |
| 75 | inactive | inactive |
| 76 | inactive | inactive |
| 77 | inactive | inactive |
| 78 | inactive | inactive |
| 79 | inactive | inactive |
| 83 | inactive | inactive |
| 84 | inactive | inactive |
| 85 | inactive | active |
| 86 | inactive | active |
| 87 | active | active |
| 89 | inactive | inactive |
| 90 | inactive | inactive |
| 91 | inactive | inactive |
| 92 | inactive | inactive |
| 98 | active | active |
| 99 | active | active |
| 100 | inactive | active |
| 102 | inactive | inactive |
| 107 | inactive | inactive |
| 110 | active | inactive |
| 111 | inactive | inactive |
| 112 | inactive | active |
| 113 | inactive | inactive |
| 114 | inactive | inactive |
| 115 | inactive | inactive |
| 116 | active | active |
| 118 | toxic | toxic |
| 119 | inactive | active |
| 120 | active | active |
| 123 | inactive | active |
| 124 | active | active |
| 125 | active | active |
| 126 | active | active |
| 127 | active | active |
| 128 | inactive | inactive |
| 129 | inactive | inactive |
| 130 | active | active |
| 133 | inactive | active |
| 134 | inactive | inactive |
| 138 | inactive | inactive |
| 139 | inactive | inactive |
| 140 | inactive | active |
| 142 | inactive | inactive |
| 202 | active | active |
| 205 | inactive | active |
| 206 | active | active |
| 207 | active | active |
| 208 | active | active |
| 209 | inactive | inactive |
| 210 | inactive | active |
| 211 | inactive | inactive |
| 212 | active | active |
| 214 | inactive | inactive |
| 215 | inactive | inactive |
| 217 | inactive | inactive |
| 218 | active | active |

Example 181

Ventral Prostate and Seminal Vesicle Weight In Vivo Assay

Immature (approximately 50 g) castrated male Sprague Dawley rats (Charles River) were treated once daily for five days with test compound (usually given orally at 40 mg/kg in a volume of 0.3 mL, in 30% cyclodextrin or 0.5% methylcellulose vehicle) and with testosterone propionate (given subcutaneously by injection at the nape of the neck at 2 mg/kg, in a volume of 0.1 mL in sesame oil). On the sixth day, the rats were euthanized by asphyxiation in carbon dioxide. Ventral prosatates and seminal vesicles were removed and their wet weights determined. Test compound activity was determined as the percent inhibition of testosterone-enhanced tissue weights, with a vehicle-treated control group set to zero percent and a testosterone alone-treated control group set to 100%.

A test compound was said to be "active" if the non weight adjusted prostate weight was ≦40 mg or the % Inhibition prostate weight, body weight adjusted was ≧60% @ 2 mg/day dosage. ID$_{50}$'s, if determined, of ≦20 mg/day also indicated an active compound.

Representative compounds of the present invention were tested according to the procedure described, with results as listed in Table 11 below. For the compounds listed in Table 11 as "inactive", one skilled in the art will recognize that said compounds may or may not have shown an effect on prostate and/or vesical weight, rather they are listed herein as "inactive" as they did not meet the specified criteria defined above.

TABLE 11

| ID # | Inhibition of prostate (non-weight prostate weight, mg) | Inhibition of seminal vesicle (non-weight seminal vesicle weight, mg) |
|---|---|---|
| 1 | active | active |
| 2 | active | active |
| 3 | active | active |
| 4 | active | active |
| 5 | active | active |
| 6 | active | active |
| 7 | active | inactive |
| 8 | active | inactive |
| 9 | active | inactive |
| 10 | active | active |
| 11 | inactive | inactive |
| 12 | inactive | inactive |
| 13 | active | active |
| 14 | active | active |
| 15 | inactive | inactive |
| 24 | inactive | inactive |
| 25 | active | active |
| 42 | active | active |
| 49 | active | active |
| 112 | inactive | inactive |
| 113 | inactive | inactive |
| 120 | active | active |
| 124 | inactive | inactive |
| 127 | active | active |
| 128 | active | active |
| 129 | inactive | inactive |
| 133 | inactive | active |
| 138 | inactive | inactive |
| 139 | active | active |
| 140 | inactive | inactive |
| 141 | inactive | inactive |
| 142 | inactive | active |
| 143 | inactive | inactive |
| 205 | active | active |
| 214 | inactive | inactive |

Example 182

As a specific embodiment of an oral composition, 100 mg of the compound prepared as in Example 95 is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A method of treating benign prostatic hyperplasia comprising administering to a subject in need thereof a therapeutically effective amount of the compound of Formula I

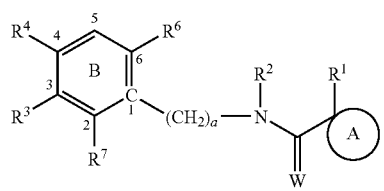

Formula I wherein
W is selected from the group consisting of O, S and NR$^F$;
wherein R$^F$ is selected from the group consisting of hydrogen, hydroxy, cyano, C$_{1-4}$alkyl, C$_{1-4}$alkoxy and —SO$_2$—C$_{1-4}$alkyl;
R$^1$ is selected from the group consisting of C$_{1-4}$-alkyl and halogenated C$_{1-4}$-alkyl;
R$^2$ is selected from the group consisting of hydrogen, C$_{1-4}$-alkyl, halogenated C$_{1-4}$alkyl, —C(O)O—C$_{1-4}$-alkyl, —C(O)—C$_{1-4}$-alkyl and —C(O)-(halogenated C$_{1-4}$-alkyl);
a is an integer from 0 to 1;

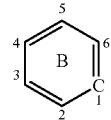

is pyridyl;
R$^3$ is absent or selected from the group consisting of hydrogen, halogen, C$_{1-4}$-alkyl, halogenated C$_{1-4}$alkyl, cyano, nitro, amino, C$_{1-4}$alkylamino, di(C$_{1-4}$alkyl)amino, —O—C$_{1-4}$alkyl, —S(O)$_{0-2}$—C$_{1-4}$-alkyl, —NR$^A$—C(O)—C$_{1-4}$-alkyl, benzyl, —O-phenyl, —C(O)-phenyl and —S(O)$_{0-2}$-phenyl; wherein R$^A$ is selected from hydrogen or C$_{1-4}$alkyl;
R$^4$ absent or is selected from the group consisting of hydrogen, halogen, C$_{1-4}$-alkyl, halogenated C$_{1-4}$alkyl, cyano, nitro, amino, C$_{1-4}$alkylamino, di(C$_{1-4}$alkyl)amino, —O—C$_{1-4}$alkyl, —S(O)$_{0-2}$—C$_{1-4}$alkyl, —NR$^B$—C(O)—C$_{1-4}$alkyl, benzyl, —O-phenyl, —C(O)-phenyl and —S(O)$_{0-2}$-phenyl; wherein R$^B$ is selected from hydrogen or C$_{1-4}$alkyl;
R$^6$ and R$^7$ are each independently absent or selected from the group consisting of hydrogen, halogen, C$_{1-4}$-alkyl, C$_{2-4}$-alkenyl, C$_{1-4}$-alkoxy, cyano, —C(O)—C$_{1-4}$-alkyl and —S(O)$_{0-2}$—C$_{1-4}$alkyl;
provided that R$^3$ is absent when a nitrogen atom is present at the 3-position of

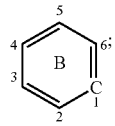

provided further that R$^4$ is absent when a nitrogen atom is present at the 4-position of

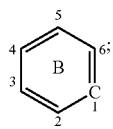

provided further that $R^6$ is absent when a nitrogen atom is present at the 6-position of

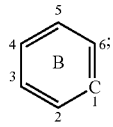

provided further that $R^7$ is absent when a nitrogen atom is present at the 2-position of

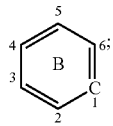

is selected from the group consisting of

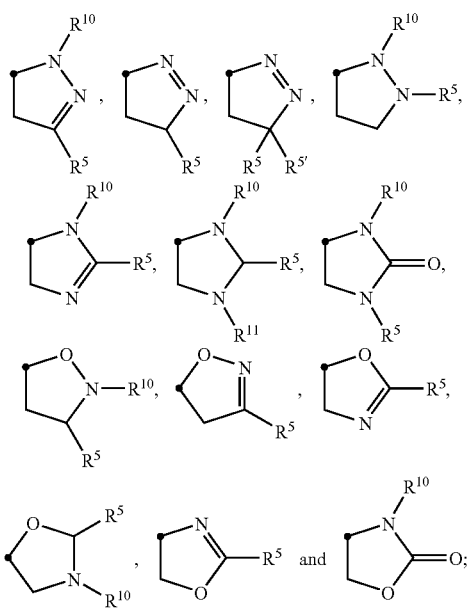

wherein $R^{5'}$ is selected from the group consisting of halogen and $C_{1-4}$alkyl; and wherein $R^{10}$ and $R^{11}$ are each independently selected from hydrogen, $C_{1-4}$alkyl, benzyl or —C(O)—CF$_3$;
$R^5$ is selected from the group consisting of hydrogen, carboxy, alkyl, halogenated $C_{1-4}$alkyl, hydroxy substituted $C_{1-4}$alkyl, cycloalkyl, aryl, aralkyl, heteroaryl, heteroaryl-alkyl-, heterocycloalkyl, heterocycloalkyl-alkyl-, —C(O)— alkyl, —C(O)-(halogenated $C_{1-4}$alkyl), —C(O)O—$C_{1-4}$alkyl, —C(O)O-aryl, —$C_{1-4}$alkyl-S(O)$_{0-2}$—$C_{1-4}$alkyl, t-butyl-dimethyl-silyl and trimethylsilyl;
wherein the aryl, cycloalkyl, heteroaryl or heterocycloalkyl, whether alone or as part of a substituent group is optionally substituted with one or more substituents independently selected from the group consisting of halogen, hydroxy, $C_{1-4}$alkyl, $C_{1-4}$alkoxy, halogenated $C_{1-4}$alkyl, halogenated $C_{1-4}$alkoxy, cyano, nitro, amino, $C_{1-4}$alkylamino, di($C_{1-4}$alkyl)amino, —NR$^C$—C(O)—$C_{1-4}$alkyl, NR$^C$—C(O)-(halogenated $C_{1-4}$alkyl), —C(O)O—$C_{1-4}$alkyl, —S(O)$_{0-2}$—$C_{1-4}$alkyl, —SO$_2$—NR$^C$R$^D$, trimethyl-silyl and t-butyl-dimethyl-silyloxy; wherein R$^C$ and R$^D$ are each independently selected from hydrogen or $C_{1-4}$alkyl;
or a pharmaceutically acceptable salt thereof.

2. A method of treating benign prostatic hyperplasia comprising administering to a subject in need thereof a therapeutically effective amount of a composition of comprising a pharmaceutically acceptable carrier and a compound of Formula I

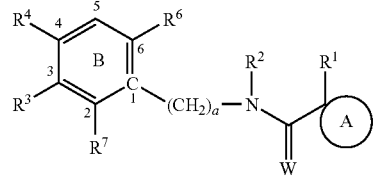

Formula I wherein
W is selected from the group consisting of O, S and NR$^F$;
wherein R$^F$ is selected from the group consisting of hydrogen, hydroxy, cyano, $C_{1-4}$alkyl, $C_{1-4}$alkoxy and —SO$_2$—$C_{1-4}$alkyl;
$R^1$ is selected from the group consisting of $C_{1-4}$-alkyl and halogenated $C_{1-4}$alkyl;
$R^2$ is selected from the group consisting of hydrogen, $C_{1-4}$alkyl, halogenated $C_{1-4}$alkyl, —C(O)O—$C_{1-4}$alkyl, —C(O)—$C_{1-4}$alkyl and —C(O)-(halogenated $C_{1-4}$alkyl);
a is an integer from 0 to 1;

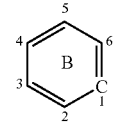

is pyridyl;
$R^3$ is absent or selected from the group consisting of hydrogen, halogen, $C_{1-4}$alkyl, halogenated $C_{1-4}$alkyl, cyano, nitro, amino, $C_{1-4}$alkylamino, di($C_{1-4}$alkyl)amino, —O—$C_{1-4}$alkyl, —S(O)$_{0-2}$—$C_{1-4}$alkyl, —NR$^A$—C(O)—$C_{1-4}$alkyl, benzyl, —O-phenyl, —C(O)-phenyl and —S(O)$_{0-2}$-phenyl; wherein R$^A$ is selected from hydrogen or $C_{1-4}$alkyl;
$R^4$ absent or is selected from the group consisting of hydrogen, halogen, $C_{1-4}$alkyl, halogenated $C_{1-4}$alkyl, cyano, nitro, amino, $C_{1-4}$alkylamino, di($C_{1-4}$alkyl)amino, —O—$C_{1-4}$alkyl, —$S(O)_{0-2}$—$C_{1-4}$alkyl, —$NR^B$—C(O)—$C_{1-4}$alkyl, benzyl, —O-phenyl, —C(O)-phenyl and —$S(O)_{0-2}$-phenyl; wherein $R^B$ is selected from hydrogen or $C_{1-4}$alkyl;

$R^6$ and $R^7$ are each independently absent or selected from the group consisting of hydrogen, halogen, $C_{1-4}$alkyl, $C_{2-4}$alkenyl, $C_{1-4}$alkoxy, cyano, —C(O)—$C_{1-4}$alkyl and —$S(O)_{0-2}$—$C_{1-4}$alkyl;

provided that $R^3$ is absent when a nitrogen atom is present at the 3-position of

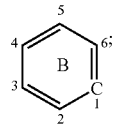

provided further that $R^4$ is absent when a nitrogen atom is present at the 4-position of

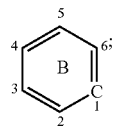

provided further that $R^6$ is absent when a nitrogen atom is present at the 6-position of

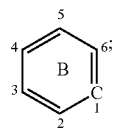

provided further that $R^7$ is absent when a nitrogen atom is present at the 2-position of

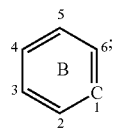

A is selected from the group consisting of

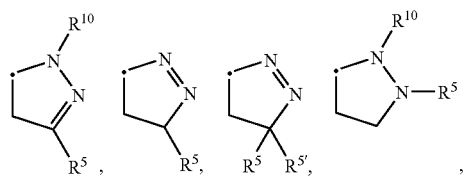

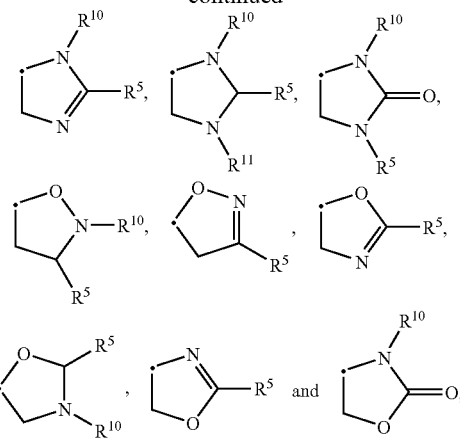

wherein $R^{5'}$ is selected from the group consisting of halogen and $C_{1-4}$alkyl; and wherein $R^{10}$ and $R^{11}$ are each independently selected from hydrogen, $C_{1-4}$alkyl, benzyl or —C(O)—$CF_3$;

$R^5$ is selected from the group consisting of hydrogen, carboxy, alkyl, halogenated $C_{1-4}$alkyl, hydroxy substituted $C_{1-4}$alkyl, cycloalkyl, aryl, aralkyl, heteroaryl, heteroarylalkyl-, heterocycloalkyl, heterocycloalkyl-alkyl-, —C(O)—alkyl, —C(O)-(halogenated $C_{1-4}$alkyl), —C(O)O—$C_{1-4}$alkyl, —C(O)O-aryl, —$C_{1-4}$alkyl-$S(O)_{0-2}$—$C_{1-4}$alkyl, t-butyl-dimethyl-silyl and trimethylsilyl;

wherein the aryl, cycloalkyl, heteroaryl or heterocycloalkyl, whether alone or as part of a substituent group is optionally substituted with one or more substituents independently selected from the group consisting of halogen, hydroxy, $C_{1-4}$alkyl, $C_{1-4}$-alkoxy, halogenated $C_{1-4}$alkyl, halogenated $C_{1-4}$alkoxy, cyano, nitro, amino, $C_{1-4}$alkylamino, di($C_{1-4}$ alkyl)amino, —$NR^C$—C(O)—$C_{1-4}$alkyl, $NR^C$—C(O)-(halogenated $C_{1-4}$alkyl), —C(O)O—$C_{1-4}$alkyl, —$S(O)_{0-2}$—$C_{1-4}$alkyl, —$SO_2$—$NR^C R^D$, trimethyl-silyl and t-butyl-dimethyl-silyloxy;

wherein $R^C$ and $R^D$ are each independently selected from hydrogen or $C_{1-4}$alkyl;

or a pharmaceutically acceptable salt thereof.

3. The method of claim 1, wherein the compound of formula (I)

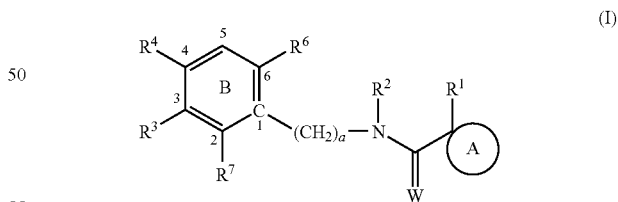

is

W is selected from the group consisting of O, S and $NR^F$; wherein $R^F$ is selected from the group consisting of hydrogen, hydroxy, $C_{1-4}$alkyl, $C_{1-4}$alkoxy, cyano and —$SO_2$—$C_{1-4}$alkyl;

$R^1$ is selected from the group consisting of $C_{1-4}$alkyl and halogenated $C_{1-4}$alkyl;

$R^2$ is selected from the group consisting of hydrogen, $C_{1-4}$alkyl, halogenated $C_{1-4}$alkyl, —C(O)O—$C_{1-4}$alkyl, —C(O)—$C_{1-4}$ alkyl and —C(O)-(halogenated $C_{1-4}$alkyl);

a is an integer from 0 to 1;

$R^3$ is selected from the group consisting of hydrogen, halogen, $C_{1-4}$ alkyl, halogenated $C_{1-4}$ alkyl, cyano, nitro, amino benzyl, —O-phenyl, —C(O)-phenyl, —S(O)$_{0-2}$—$C_{1-4}$ alkyl, $C_{1-4}$ alkylamino, di $C_{1-4}$ alkylamino, —O—$C_{1-4}$ alkyl, —NR$^A$—C(O)—$C_{1-4}$ alkyl and —S(O)$_{0-2}$-phenyl, wherein $R^A$ is either hydrogen or $C_{1-4}$ alkyl;

$R^4$ is selected from the group consisting of hydrogen, halogen, $C_{1-4}$ alkyl, halogenated $C_{1-4}$ alkyl, cyano, nitro, amino, benzyl, —O-phenyl, —C(O)-phenyl, —S(O)$_{0-2}$—$C_{1-4}$ alkyl, $C_{1-4}$ alkylamino, di $C_{1-4}$ alkylamino, —O—$C_{1-4}$ alkyl, —NR$^B$—C(O)—$C_{1-4}$ alkyl and —S(O)$_{0-2}$-phenyl, wherein $R^B$ is either hydrogen or $C_{1-4}$ alkyl;

provided that at least one of $R^3$ or $R^4$ is other than hydrogen;

$R^6$ and $R^7$ are each independently selected from the group consisting of hydrogen, halogen, $C_{1-4}$alkyl, $C_{2-4}$ alkenyl, $C_{1-4}$alkoxy, cyano, —C(O)O—$C_{1-4}$alkyl and —S(O)$_{0-2}$—$C_{1-4}$alkyl;

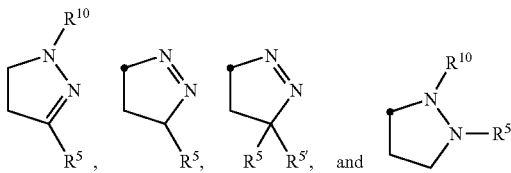

is selected from the group consisting of wherein $R^{5'}$ is selected from the group consisting of halogen and $C_{1-4}$alkyl; and wherein $R^{10}$ is selected from hydrogen, $C_{1-4}$alkyl, benzyl or —C(O)—CF$_3$;

$R^5$ is selected from the group consisting of hydrogen, carboxy, alkyl, halogenated $C_{1-4}$alkyl, hydroxy substituted $C_{1-4}$alkyl, cycloalkyl, aryl, aralkyl, —C(O)—$C_{1-4}$alkyl, —C(O)-(halogenated $C_{1-4}$alkyl), —C(O)O—$C_{1-4}$alkyl, —C(O)O-aryl, —$C_{1-4}$alkyl-S(O)$_{0-2}$—$C_{1-4}$alkyl, t-butyl-dimethyl-silyl and trimethylsilyl;

wherein the aryl, whether alone or as part of a substituent group is optionally substituted with one or more substituents independently selected from the group consisting of halogen, hydroxy, $C_{1-4}$alkyl, $C_{1-4}$alkoxy, halogenated $C_{1-4}$alkyl, cyano, nitro, —NR$^C$—C(O)—$C_{1-4}$alkyl, NR$^C$—C(O)-(halogenated $C_{1-4}$alkyl), —C(O)O—$C_{1-4}$alkyl, trimethyl-silyl and t-butyl-dimethyl-silyloxy; wherein R$^C$ and R$^D$ are each independently selected from hydrogen or $C_{1-4}$alkyl;

or a pharmaceutically acceptable salt thereof.

4. The method of claim 3, wherein the compound further comprises

W is selected from the group consisting of O, S and NR$^F$; wherein $R^F$ is selected from the group consisting of hydrogen, hydroxy, $C_{1-4}$alkyl, $C_{1-2}$alkoxy, cyano and —SO$_2$—$C_{1-2}$alkyl;

$R^1$ is selected from the group consisting of $C_{1-4}$alkyl and halogenated $C_{1-2}$alkyl;

$R^2$ is selected from the group consisting of hydrogen, $C_{1-4}$alkyl, halogenated $C_{1-2}$alkyl and —C(O)-(halogenated $C_{1-2}$alkyl);

a is an integer from 0 to 1;

$R^3$ is selected from the group consisting of hydrogen, halogen, halogenated $C_{1-4}$alkyl and cyano;

$R^4$ is selected from the group consisting of halogen, cyano, nitro, benzyl, —O-phenyl, —C(O)-phenyl, —S(O)$_{0-2}$—$C_{1-4}$alkyl and —S(O)$_{0-2}$-phenyl;

$R^6$ and $R^7$ are each independently selected from the group consisting of hydrogen, halogen, $C_{1-2}$alkyl, $C_{1-2}$alkoxy, cyano, —C(O)O—$C_{1-2}$alkyl, —S—$C_{1-4}$alkyl and —SO$_2$—$C_{1-4}$alkyl;

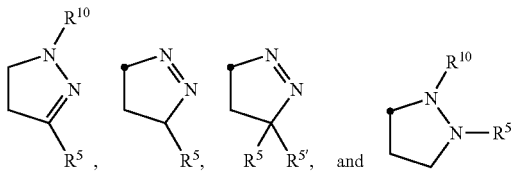

is selected from the group consisting of wherein $R^{5'}$ is halogen; and wherein $R^{10}$ is selected from hydrogen, $C_{1-4}$alkyl, benzyl or —C(O)—CF$_3$;

$R^5$ is selected from the group consisting of hydrogen, carboxy, $C_{1-4}$alkyl, halogenated $C_{1-4}$alkyl, —$C_{1-4}$alkyl-OH, cycloalkyl, aryl, aralkyl, $C_{1-4}$alkyl-S—$C_{1-4}$alkyl, —C(O)O—$C_{1-4}$alkyl, —C(O)-(halogenated $C_{1-4}$alkyl) and trimethylsilyl;

wherein the aryl, whether alone or as part of a substituent group is optionally substituted with one or more substituents independently selected from hydroxy, halogen, $C_{1-4}$alkyl, —O—$C_{1-4}$alkyl, —C(O)O—$C_{1-4}$alkyl, —NH—C(O)—$C_{1-4}$alkyl, —NH—C(O)-(halogenated $C_{1-4}$alkyl) or t-butyl-dimethyl-silyloxy;

or a pharmaceutically acceptable salt thereof.

5. The method as in claim 4, wherein

W is selected from the group consisting of O, S and NR$^F$; wherein $R^F$ is selected from the group consisting of hydrogen, hydroxy, methyl, ethyl, methoxy, cyano and —SO$_2$-methyl;

$R^1$ is selected from the group consisting of methyl, (S)-methyl, (R)-methyl, ethyl, n-propyl and trifluoromethyl;

$R^2$ is selected from the group consisting of hydrogen, methyl, trifluoroethyl and —C(O)—CF$_3$;

a is an integer from 0 to 1;

$R^3$ is selected from the group consisting of hydrogen, chloro, trifluoromethyl and cyano;

$R^4$ is selected from the group consisting of chloro, bromo, cyano, nitro, benzyl, —O-phenyl, —S-phenyl, —C(O)-phenyl, —SO$_2$-methyl and —SO$_2$-phenyl;

$R^6$ is selected from the group consisting of hydrogen, chloro, iodo, ethyl, methoxy, cyano, —C(O)O-methyl, —S-ethyl, —S-t-butyl and —SO$_2$-ethyl;

$R^7$ is selected from the group consisting of hydrogen, chloro and ethyl;

is selected from the group consisting of

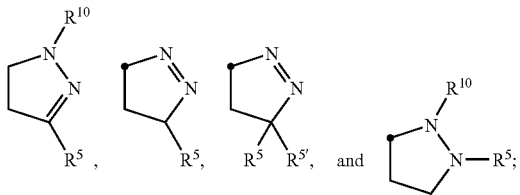

wherein $R^{5'}$ is chloro; and wherein $R^{10}$ is selected from hydrogen, methyl, ethyl, benzyl or —C(O)—CF$_3$;

$R^5$ is selected from the group consisting of hydrogen, carboxy, methyl, ethyl, n-propyl, isopropyl, isobutyl, t-butyl, trifluoromethyl, 2,2,2-trifluoro-ethyl, 1,1,2,2,2-pentafluoro-ethyl, hydroxy-methyl-, 2-hydroxy-phenyl, 4-fluorophenyl, 3,4-difluorophenyl, 2,3,4,5,6-pentafluorophenyl, 4-ethylphenyl, 4-methoxy-phenyl, 2-hydroxy-3-fluoro-phenyl, 2-fluoro-3-hydroxy-phenyl, 3-methyl-4-fluoro-phenyl, cyclopentyl, cyclohexyl, 4-methoxy-carbonyl-phenyl, 3-methyl-carbonyl-amino-phenyl, 4-methyl-carbonyl-amino-phenyl, 4-(trifluoromethyl-carbonyl-amino)-phenyl, 2-(t-butyl-dimethyl-silyloxy)-3-fluoro-phenyl, t-butyl-dimethyl-silyloxy-phenyl, 4-methyl-carbonyl-amino-benzyl, 4-methyl-carbonyl-amino-phenyl, 2-furyl, 2-thienyl, 3-pyridyl, 2-tetrahydrofuryl, methyl-thio-ethyl-, ethyl-thio-ethyl-, ethoxy-carbonyl-, t-butoxy-carbonyl-, trifluoromethyl-carbonyl- and trimethylsilyl;

or a pharmaceutically acceptable salt thereof.

6. The method as in claim 4, wherein

W is selected from the group consisting of O, S and NR$^F$; wherein R$^F$ is selected from the group consisting of hydrogen, hydroxy, cyano, C$_{1-4}$alkyl, C$_{1-2}$alkoxy and —SO$_2$—C$_{1-2}$alkyl;

$R^1$ is selected from the group consisting of C$_{1-4}$alkyl and halogenated C$_{1-4}$alkyl;

$R^2$ is selected from the group consisting of hydrogen, C$_{1-4}$alkyl, halogenated C$_{1-2}$alkyl and —C(O)-(halogenated C$_{1-2}$alkyl);

a is an integer from 0 to 1;

$R^3$ is selected from the group consisting of hydrogen, halogen, halogenated C$_{1-4}$alkyl and cyano;

$R^4$ is selected from the group consisting of halogen, cyano, nitro, benzyl, —O-phenyl, —C(O)-phenyl, —S(O)$_{0-2}$—C$_{1-4}$alkyl and —S(O)$_{0-2}$-phenyl;

$R^6$ and $R^7$ are each independently selected from the group consisting of hydrogen, halogen, C$_{1-2}$alkyl, C$_{1-2}$alkoxy, cyano, —C(O)O—C$_{1-2}$alkyl, —S—C$_{1-4}$alkyl and —SO$_2$—C$_{1-4}$alkyl;

(A)

is selected from the group consisting of

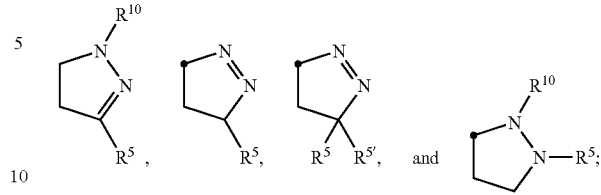

wherein $R^{5'}$ is halogen; and wherein $R^{10}$ is selected from the group consisting of hydrogen, C$_{1-4}$alkyl, benzyl and —C(O)—CF$_3$;

$R^5$ is selected from the group consisting of hydrogen, carboxy, C$_{1-4}$alkyl, halogenated C$_{1-4}$alkyl, —C$_{1-4}$alkyl-OH, cycloalkyl, aryl, aralkyl, —C$_{1-4}$alkyl-S—C$_{1-4}$alkyl, —C(O)O—C$_{1-4}$alkyl, —C(O)-(halogenated C$_{1-4}$alkyl) and trimethylsilyl;

wherein the aryl, whether alone or as part of a substituent group is optionally substituted with one or more substituents independently selected from hydroxy, halogen, C$_{1-4}$alkyl, —O—C$_{1-4}$alkyl, —C(O)O—C$_{1-4}$alkyl, —NH—C(O)—C$_{1-4}$alkyl, —NH—C(O)-(halogenated C$_{1-4}$alkyl) or t-butyl-dimethyl-silyloxy;

or a pharmaceutically acceptable salt thereof.

7. The method as in claim 6, wherein

W is selected from the group consisting of O, S and NR$^F$; wherein R$^F$ is selected from the group consisting of hydrogen, methyl, ethyl, methoxy, cyano and —SO$_2$-methyl;

$R^1$ is selected from the group consisting of methyl, (S)-methyl, (R)-methyl, ethyl, n-propyl and trifluoromethyl;

$R^2$ is selected from the group consisting of hydrogen, methyl, trifluoromethyl and —C(O)—CF$_3$;

a is an integer from 0 to 1;

$R^3$ is selected from the group consisting of hydrogen, chloro, trifluoromethyl and cyano;

$R^4$ is selected from the group consisting of chloro, bromo, cyano, nitro, benzyl, —O-phenyl, —S-phenyl, —C(O)-phenyl, —SO$_2$-methyl and —SO$_2$-phenyl;

$R^6$ is selected from the group consisting of hydrogen, chloro, iodo, ethyl, methoxy, cyano, —C(O)O-methyl, —S-ethyl, —S-t-butyl and —SO$_2$-ethyl;

$R^7$ is selected from the group consisting of hydrogen, chloro and ethyl;

(A)

is selected from the group consisting of

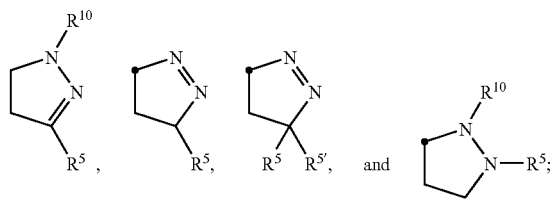

wherein $R^{5'}$ is chloro; and wherein $R^{10}$ is selected from hydrogen, methyl, ethyl, benzyl or —C(O)—CF$_3$;

$R^5$ is selected from the group consisting of hydrogen, carboxy, methyl, ethyl, n-propyl, isopropyl, isobutyl, t-butyl, trifluoromethyl, 2,2,2-trifluoro-ethyl, 1,1,2,2,2-pentafluoro-ethyl, hydroxy-methyl-, 2-hydroxy-phenyl, 4-fluorophenyl, 3,4-difluorophenyl, 2,3,4,5,6-pentafluorophenyl, 4-ethylphenyl, 4-methoxy-phenyl, 2-hydroxy-3-fluoro-phenyl, 2-fluoro-3-hydroxy-phenyl, 3-methyl-4-fluoro-phenyl, cyclopentyl, cyclohexyl, 4-methoxy-carbonyl-phenyl, 3-methyl-carbonyl-amino-phenyl, 4-methyl-carbonyl-amino-phenyl, 4-(trifluoromethyl-carbonyl-amino)-phenyl, 2-(t-butyl-dimethyl-silyloxy)-3-fluoro-phenyl, t-butyl-dimethyl-silyloxy-phenyl, 4-methyl-carbonyl-amino-benzyl, 4-methyl-carbonyl-amino-phenyl, 2-furyl, 2-thienyl, 3-pyridyl, 2-tetrahydrofuryl, methyl-thio-ethyl-, ethyl-thio-ethyl-, ethoxy-carbonyl-, t-butoxy-carbonyl-, trifluoromethyl-carbonyl- and trimethylsilyl;

or a pharmaceutically acceptable salt thereof.

8. The method as in claim 5, wherein

W is selected from the group consisting of O, NH, N(OH), N(ethyl) and N(methoxy);

$R^1$ is selected from the group consisting of methyl, (R)-methyl, (S)-methyl, ethyl and trifluoromethyl;

$R^2$ is selected from the group consisting of hydrogen and methyl;

a is an integer from 0 to 1;

$R^3$ is selected from the group consisting of hydrogen and trifluoromethyl;

$R^4$ is selected from the group consisting of bromo, cyano, nitro and —$SO_2$-phenyl;

$R^6$ is selected from the group consisting of hydrogen, iodo, chloro and —S-ethyl;

$R^7$ is selected from the group consisting of hydrogen and ethyl;

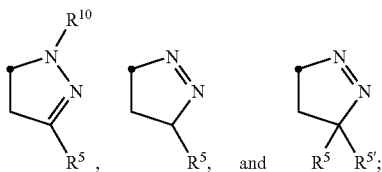

is selected from the group consisting of wherein $R^{5'}$ is chloro; and wherein $R^{10}$ is selected from the group consisting of hydrogen, methyl and ethyl;

$R^5$ is selected from the group consisting of methyl, trifluoromethyl, 1,1,2,2,2-pentafluoro-ethyl, —C(O)O-ethyl, 4-methyl-carbonyl-amino-phenyl, 4-trifluoromethyl-carbonyl-amino-phenyl and 4-methyl-carbonyl-amino-benzyl;

or a pharmaceutically acceptable salt thereof.

9. The method as in claim 5, wherein

W is selected from the group consisting of O and N(ethyl);

$R^1$ is methyl;

$R^2$ is selected from the group consisting of hydrogen and methyl;

a is an integer from 0 to 1;

$R^3$ is trifluoromethyl;

$R^4$ is selected from the group consisting of chloro, cyano and nitro;

$R^6$ is selected from the group consisting of hydrogen, chloro, ethyl and —$SO_2$-ethyl;

$R^7$ is selected from the group consisting of hydrogen, chloro and ethyl;

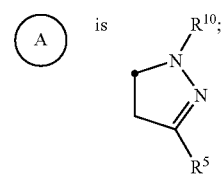

wherein $R^{10}$ is selected from the group consisting of hydrogen and ethyl;

$R^5$ is selected from the group consisting of hydrogen, n-propyl, isopropyl, trifluoromethyl, 4-fluorophenyl, 3,4-difluorophenyl, 2,3,4,5,6-pentafluorophenyl, 4-methoxyphenyl, 4-ethylphenyl, cyclohexyl, 2-furyl and 2-thienyl;

or a pharmaceutically acceptable salt thereof.

10. A method of claim 3 comprising administering to a subject in need thereof a therapeutically effective amount of a composition comprising a pharmaceutically acceptable carrier and a compound of Formula (I).

* * * * *